(12) United States Patent
Joosten et al.

(10) Patent No.: US 10,629,817 B2
(45) Date of Patent: Apr. 21, 2020

(54) MATERIALS FOR ORGANIC ELECTROLUMINESCENT DEVICES

(71) Applicant: Merck Patent GmbH, Darmstadt (DE)

(72) Inventors: Dominik Joosten, Frankfurt am Main (DE); Florian Maier-Flaig, Weinheim (DE); Anna Hayer, Darmstadt (DE); Holger Heil, Frankfurt am Main (DE)

(73) Assignee: Merck Patent GmbH (DE)

( * ) Notice: Subject to any disclaimer, the term of this patent is extended or adjusted under 35 U.S.C. 154(b) by 0 days.

(21) Appl. No.: 15/575,179

(22) PCT Filed: Apr. 27, 2016

(86) PCT No.: PCT/EP2016/000672
§ 371 (c)(1),
(2) Date: Nov. 17, 2017

(87) PCT Pub. No.: WO2016/184540
PCT Pub. Date: Nov. 24, 2016

(65) Prior Publication Data
US 2018/0145260 A1 May 24, 2018

(30) Foreign Application Priority Data
May 18, 2015 (EP) .................... 15001477

(51) Int. Cl.
*H01L 51/00* (2006.01)
*C07C 13/567* (2006.01)
*C07C 13/72* (2006.01)
*C09K 11/06* (2006.01)
*C07C 13/62* (2006.01)
*H01L 51/50* (2006.01)

(52) U.S. Cl.
CPC ........ *H01L 51/0052* (2013.01); *C07C 13/567* (2013.01); *C07C 13/62* (2013.01); *C07C 13/72* (2013.01); *C09K 11/06* (2013.01); *H01L 51/0054* (2013.01); *H01L 51/0055* (2013.01); *H01L 51/0056* (2013.01); *H01L 51/0058* (2013.01); *C07C 2601/14* (2017.05); *C07C 2602/08* (2017.05); *C07C 2602/10* (2017.05); *C07C 2603/18* (2017.05); *C07C 2603/40* (2017.05); *C07C 2603/52* (2017.05); *C07C 2603/97* (2017.05); *C09K 2211/1007* (2013.01); *C09K 2211/1011* (2013.01); *H01L 51/5012* (2013.01); *H01L 51/5016* (2013.01); *H01L 51/5056* (2013.01); *H01L 51/5072* (2013.01); *H01L 51/5096* (2013.01); *Y02E 10/549* (2013.01)

(58) Field of Classification Search
CPC . C07C 2601/14; C07C 2603/18; C07C 13/62; C07C 13/567; C07C 13/72; C07C 2602/10; C07C 2603/40; C07C 2603/52; C07C 2603/97; C07C 2602/08; Y02E 10/549; C09K 2211/1007; C09K 2211/1011; C09K 11/06; H01L 51/5012; H01L 51/5096; H01L 51/5072; H01L 51/5056; H01L 51/5016; H01L 51/0052; H01L 51/5024; H01L 51/0054; H01L 51/0055; H01L 51/0056; H01L 51/0058
USPC ........................................................ 252/500
See application file for complete search history.

(56) References Cited

U.S. PATENT DOCUMENTS

| | | | |
|---|---|---|---|
| 9,187,456 B2 | 11/2015 | Franz et al. | |
| 10,355,217 B2* | 7/2019 | Pfister | |
| 2011/0037027 A1* | 2/2011 | Stoessel | C07C 13/567 252/301.16 |
| 2011/0187266 A1 | 8/2011 | Fukushima et al. | |
| 2011/0253994 A1 | 10/2011 | Kim et al. | |
| 2011/0303908 A1 | 12/2011 | Min et al. | |
| 2012/0056171 A1 | 3/2012 | Kim et al. | |
| 2012/0061714 A1 | 3/2012 | Osaka et al. | |
| 2012/0080667 A1 | 4/2012 | Nowatari et al. | |
| 2012/0228554 A1* | 9/2012 | Franz | C07D 251/16 252/500 |
| 2013/0221335 A1 | 8/2013 | Suzuki et al. | |
| 2015/0179940 A1* | 6/2015 | Mujica-Fernaud | H01L 51/0052 252/519.21 |
| 2015/0207075 A1* | 7/2015 | Mujica-Fernaud | C09K 11/06 252/500 |
| 2015/0287937 A1 | 10/2015 | Che et al. | |
| 2016/0301005 A1* | 10/2016 | Pfister | C09K 11/06 |

FOREIGN PATENT DOCUMENTS

| | | |
|---|---|---|
| CN | 103194215 B | 7/2013 |
| CN | 104037339 A | 9/2014 |
| DE | 102009053644 A1 | 5/2011 |
| EP | 1993154 A1 | 11/2008 |
| JP | 2004300314 A | 10/2004 |
| JP | 2011082238 A | 4/2011 |

(Continued)

OTHER PUBLICATIONS

Cas reg. No. 2047361-36-2, Dec. 12, 2016. (Year: 2016).*
International Search Report for PCT/EP2016/000672 dated Jul. 20, 2016.
Written Opinion of the International Searching Authority for PCT/EP2016/000672 dated Jul. 20, 2016.

(Continued)

*Primary Examiner* — Douglas J McGinty
(74) *Attorney, Agent, or Firm* — Faegre Drinker Biddle & Reath LLP

(57) ABSTRACT

The present invention relates to the fluorene derivatives and to organic electronic devices in which these Compounds are used as matrix material in the emitting layer and/or as hole transport material and/or as electron blocker or exciton blocker material and/or as electron transport material.

21 Claims, No Drawings

(56) References Cited

FOREIGN PATENT DOCUMENTS

| KR | 20150106668 A | 9/2015 | |
|---|---|---|---|
| WO | WO-2008147110 A2 | 12/2008 | |
| WO | WO-2015046955 A1 | 4/2015 | |
| WO | WO-2016013867 A1 | 1/2016 | |
| WO | WO-2018041769 A1 * | 3/2018 | ......... H01L 51/0085 |

OTHER PUBLICATIONS

Kugler, T., et al., "Charge transfer salt, electronic device, and method of forming the same", Chemical Abstracts Service, Database Accession No. 1373355-31-7, dated May 10, 2012.

* cited by examiner

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2016/000672, filed Apr. 27, 2016, which claims benefit of European Application No. 15001477.77, filed May 18, 2015, both of which are incorporated herein by reference in their entirety.

The present invention relates to materials for organic semiconductors and to the use thereof in organic electronic devices.

Organic semiconductors are being developed for a number of different kinds of electronic application. The structure of organic electroluminescent devices (OLEDs) in which these organic semiconductors are used as functional materials is described, for example, in U.S. Pat. Nos. 4,539,507, 5,151,629, EP 0676461 and WO 98/27136. However, still further improvements are desirable for the use of these devices for high-quality and long-life displays. For instance, there is currently still a need for improvement especially in the lifetime and efficiency of solution-processed or at least partly solution-processed organic electroluminescent devices. An additional requirement is for the compounds to have sufficiently high solubility in standard organic solvents for processing from solution. More particularly, for use at elevated temperature, a high glass transition temperature is essential for the achievement of long lifetimes. Generally, further improvements in lifetime, efficiency and/or voltage are desirable. There is therefore still a need for improved materials, for example host materials for fluorescent and phosphorescent emitters, but further improvements are also desirable in the case of charge transport materials, i.e. hole and electron transport materials, and charge blocker materials. Specifically the properties of these materials are frequently limiting factors for the lifetime and efficiency of the organic electroluminescent device.

As closest prior art, WO 2009/124627 and WO 2011/060859 may be cited. WO 2009/124627 discloses 9,9-diphenylfluorene derivatives preferably substituted by two aryl groups on each of the two phenyl groups. The only structures explicitly disclosed are those each substituted in the 3' and 5' positions of the phenyl groups, i.e. in the two meta positions to the bond to the fluorene. There is no disclosure of structures substituted at only one of the meta positions. WO 2011/060859 discloses 9,9-diphenylfluorene derivatives preferably having at least one triazine structure. There is no explicit disclosure of structures substituted only in the 3' position and not comprising any triazine group. No significance is ascribed to substitution only in the 3' position.

It has been found that, surprisingly, 9,9-diphenylfluorene derivatives each substituted in the 3' position on at least one phenyl group, preferably on both phenyl groups, are of very good suitability for use in organic electroluminescent devices and lead to distinct improvements over the prior art therein. The present invention therefore provides these compounds and for the use thereof in organic electronic devices. According to the substitution on the phenyl groups, the compounds of the invention are especially suitable as hole transport materials, electron or exciton blocker materials, matrix materials for fluorescent or phosphorescent compounds, hole blocker materials and electron transport materials. Materials of the invention enable an increase in the efficiency and/or an increase in the lifetime of the organic electronic device compared to materials according to the prior art. Moreover, these compounds have high thermal stability. Generally, these materials are of very good suitability for use in organic electronic devices, since they have a high glass transition temperature. In addition, these compounds have a high solubility in organic solvents and are therefore of good suitability for processing from solution.

For the sake of clarity, the structure and numbering of 9,9-diphenylfluorene is shown below:

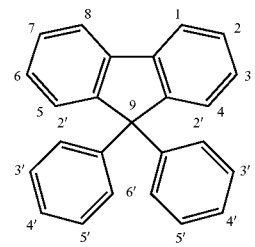 [SMILES: c1ccc(C2(c3ccccc3)c3ccccc3-c3ccccc32)cc1]

The invention thus provides compounds comprising at least one structure of the formula (I)

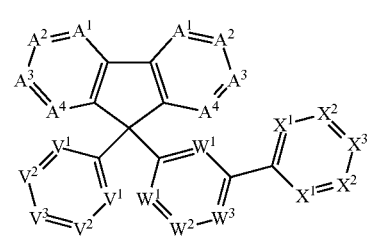

Formula (I)

where the symbols used are as follows:

$A^1$, $A^2$, $A^3$, $A^4$ is the same or different at each instance and is N or $CR^1$, preferably $CR^1$, with the proviso that not more than two of the $A^1$, $A^2$, $A^3$, $A^4$ groups in one cycle are N;

$V^1$, $V^2$, $V^3$ is the same or different at each instance and is N or $CR^2$, preferably $CR^2$, with the proviso that not more than two of the $V^1$, $V^2$, $V^3$ groups in one cycle are N;

$W^1$, $W^2$, $W^3$ is the same or different at each instance and is N or $CR^3$, preferably $CR^3$, with the proviso that not more than two of the $W^1$, $W^2$, $W^3$ groups in one cycle are N;

$X^1$, $X^2$, $X^3$ is the same or different at each instance and is N or $CR^4$, preferably $CR^4$, with the proviso that not more than two of the $X^1$, $X^2$, $X^3$ groups in one cycle are N;

$R^1$, $R^2$, $R^3$, $R^4$ is the same or different at each instance and is H, D, F, Cl, Br, I, $B(OR^5)_2$, CHO, $C(=O)R^5$, $CR^5=C(R^5)_2$, CN, $C(=O)OR^5$, $C(=O)N(R^5)_2$, $Si(R^5)_3$, $N(R^5)_2$, $NO_2$, $P(=O)(R^5)_2$, $OSO_2R^5$, $OR^5$, $S(=O)R^5$, $S(=O)_2R^5$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^5$ radicals, where one or more nonadjacent $CH_2$ groups may be replaced by $-R^5C=CR^5-$, $-C\equiv C-$, $Si(R^5)_2$, $Ge(R^5)_2$, $Sn(R^5)_2$, $C=O$, $C=S$, $C=Se$, $C=NR^5$, $-C(=O)O-$, $-C(=O)NR^5-$, $NR^5$, $P(=O)(R^5)$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^5$ radicals, or an aryloxy or heteroaryloxy group which has 5 to 40 aromatic ring atoms and may be substituted by one or more $R^5$ radicals, or a combination of these systems; at the same time, it is also possible for two or more adjacent $R^1$ substituents together to form a mono- or polycyclic, aliphatic or aromatic ring system; at the same time, it is also possible for two or more adjacent $R^2$ substituents together to form a mono- or polycyclic, aliphatic or aromatic ring system; at the same time, it is also possible for two or more adjacent $R^3$ substituents together to form a mono- or polycyclic, aliphatic or aromatic ring system; at the same time, it is also possible for two or more adjacent $R^4$ substituents together to form a mono- or polycyclic, aliphatic or aromatic ring system;

$R^5$ is the same or different at each instance and is H, D, F, Cl, Br, I, $B(OR^6)_2$, CHO, $C(=O)R^6$, $CR^6=C(R^6)_2$, CN, $C(=O)OR^6$, $C(=O)N(R^6)_2$, $Si(R^6)_3$, $N(R^6)_2$, $NO_2$, $P(=O)(R^6)_2$, $OSO_2R^6$, $OR^6$, $S(=O)R^6$, $S(=O)_2R^6$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^6$ radicals, where one or more nonadjacent $CH_2$ groups may be replaced by $-R^6C=CR^6-$, $-C\equiv C-$, $Si(R^6)_2$, $Ge(R^6)_2$, $Sn(R^6)_2$, $C=O$, $C=S$, $C=Se$, $C=NR^6$, $-C(=O)O-$, $-C(=O)NR^6-$, $NR^6$, $P(=O)(R^6)$, $-O-$, $-S-$, SO or $SO_2$ and where one or more hydrogen atoms may be replaced by D, F, Cl, Br, I, CN or $NO_2$, or an aromatic or heteroaromatic ring system which has 5 to 40 aromatic ring atoms and may be substituted in each case by one or more $R^6$ radicals, or an aryloxy or heteroaryloxy group which has 5 to 40 aromatic ring atoms and may be substituted by one or more $R^6$ radicals, or a combination of these systems; at the same time, it is also possible for two or more adjacent $R^5$ substituents together to form a mono- or polycyclic, aliphatic or aromatic ring system;

$R^6$ is the same or different at each instance and is H, D, F or an aliphatic, aromatic and/or heteroaromatic hydrocarbyl radical having 1 to 20 carbon atoms, in which hydrogen atoms may also be replaced by F; at the same time, it is also possible for two or more adjacent $R^6$ substituents together to form a mono- or polycyclic, aliphatic or aromatic ring system;

with the proviso that the $W^1$ and $V^1$ radicals are not bridged to one another;

the $R^2$ radicals in the $V^1$, $V^2$, $V^3$ groups and the $R^4$ radicals in the $X^1$, $X^2$, $X^3$ groups comprise a total of at least 12 aromatic carbon ring atoms;

the $R^1$, $R^2$, $R^3$ and $R^4$ radicals do not include a triazine structure and the $V^1$, $V^2$, $V^3$ and $W^1$, $W^2$, $W^3$ groups comprise a total of not more than two $CR^2$ and/or $CR^3$ groups comprising an aromatic or heteroaromatic ring system, i.e. in which $R^2$ and $R^3$ are an aromatic or heteroaromatic ring system.

An aryl group in the context of this invention contains 6 to 60 carbon atoms; a heteroaryl group in the context of this invention contains 2 to 60 carbon atoms and at least 1 heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, i, etc., or a fused aryl or heteroaryl group, for example naphthalene, anthracene, pyrene, quinoline, isoquinoline, etc.

An aromatic ring system in the context of this invention contains 6 to 60 carbon atoms in the ring system. A heteroaromatic ring system in the context of this invention contains 2 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention is understood to mean a system which does not necessarily contain only aryl or heteroaryl groups, but in which it is also possible for two or more aryl or heteroaryl groups to be interrupted by a short nonaromatic unit (preferably less than 10% of the atoms other than H), for example an $sp^3$-hybridized carbon, nitrogen or oxygen atom. For example, systems such as 9,9'-spirobifluorene, 9,9-diarylfluorene, triarylamine, diaryl ether, stilbene, benzophenone, etc. shall also be regarded as aromatic ring systems in the context of this invention. An aromatic or heteroaromatic ring system is likewise understood to mean systems in which two or more aryl or heteroaryl groups are joined to one another by single bonds, for example biphenyl, terphenyl or bipyridine.

In the context of the present invention, a $C_1$- to $C_{40}$-alkyl group in which individual hydrogen atoms or $CH_2$ groups may also be replaced by the abovementioned groups is more preferably understood to mean methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoroethyl and 2,2,2-trifluoroethyl. In the context of this invention, an alkenyl group is especially understood to mean ethenyl, propenyl, butenyl, pentenyl, cyclopentenyl, hexenyl, cyclohexenyl, heptenyl, cycloheptenyl, octenyl and cyclooctenyl. In the context of this invention, an alkynyl group is especially understood to mean ethynyl, propynyl, butynyl, pentynyl, hexynyl, heptynyl or octynyl. A $C_1$- to $C_{40}$-alkoxy group is more preferably understood to mean methoxy, trifluoromethoxy, ethoxy, n-propoxy, i-propoxy, n-butoxy, i-butoxy, s-butoxy, t-butoxy or 2-methylbutoxy. An aromatic or heteroaromatic ring system which has 5-60 aromatic ring atoms and may also be substituted in each case by the R radicals as defined above and which may be joined to the aromatic or heteroaromatic system via any desired positions is especially understood to mean groups derived from benzene, naphthalene, anthracene, phenanthrene, benzanthracene, pyrene, chrysene, perylene, fluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, purine, pteridine, indolizine and benzothiadiazole.

It may preferably be the case that, in compounds comprising at least one structure of the formula (I), at least one of the $V^1$, $V^2$, $V^3$ groups comprises an $R^2$ radical which is an aromatic or heteroaromatic ring system having 5 to 40 aromatic ring atoms.

The $W^1$ and $V^1$ radicals are not bridged to one another. This means that the $W^1$ and $V^1$ radicals are not bonded to one another by a bond or any $R^3$ or $R^2$ radicals present on the $W^1$ and $V^1$ radicals are not joined to one another, which likewise rules out joining via possible $R^5$ or $R^6$ substituents.

The $R^1$, $R^2$, $R^3$ and $R^4$ radicals do not comprise any triazine structure, and this likewise rules out presence of a triazine structure in possible $R^5$ or $R^6$ substituents. A triazine structure in the context of the present invention is an aromatic radical having 6 ring atoms and at least 3 nitrogen atoms in the ring, and so especially 1,3,5-triazine, 1,2,4-triazine, 1,2,3-triazine, 1,2,4,5-tetrazine, 1,2,3,4-tetrazine and 1,2,3,5-tetrazine structures are ruled out.

The $V^1$, $V^2$, $V^3$ and $W^1$, $W^2$, $W^3$ groups comprise a total of not more than two $CR^2$ and/or $CR^3$ groups comprising an aromatic or heteroaromatic ring system, which includes possible $R^5$ or $R^6$ substituents, and so a total of not more than two $R^2$ and/or $R^3$ radicals including the $R^5$ or $R^6$ substituents present on these $R^2$, $R^3$ radicals comprise an aromatic or heteroaromatic ring system.

A preferred embodiment of the compounds comprising at least one structure of the formula (I) is that of compounds containing structures of the formula (II)

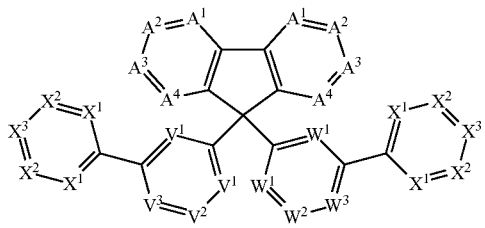

Formula (II)

where the symbols used may be as defined above, especially in connection with formula (I), where the $V^1$, $V^2$, $V^3$ and $W^1$, $W^2$, $W^3$ groups comprise a total of not more than one $R^2$ or $R^3$ radical comprising an aromatic or heteroaromatic ring system.

In a preferred configuration, compounds comprising structures of formula (I) and/or (II) can be represented by structures of the formula (I) and/or (II). Preferably, compounds comprising structures of formula (I) and/or (II) have a molecular weight of not more than 5000 g/mol, preferably not more than 4000 g/mol, particularly preferably not more than 3000 g/mol, especially preferably not more than 2000 g/mol and most preferably not more than 1200 g/mol.

In addition, it is a feature of preferred compounds of the invention that they are sublimable. These compounds generally have a molar mass of less than about 1200 g/mol.

In addition, it is a feature of preferred compounds of the invention that they have a high solubility in standard organic solvents, preferably a solubility of ≥10 mg/ml in toluene.

Preferably, not more than one of the $A^1$, $A^2$, $A^3$ and $A^4$ groups per cycle is N. More preferably, all $A^1$, $A^2$, $A^3$ and $A^4$ groups are $CR^1$.

Preferably, in addition, not more than one of the $V^1$, $V^2$ and $V^3$ groups is N. More preferably, all $V^1$, $V^2$ and $V^3$ groups are $CR^2$.

Preferably, in addition, not more than one of the $W^1$, $W^2$ and $W^3$ groups is N. More preferably, all $W^1$, $W^2$ and $W^3$ groups are $CR^3$.

Preferably, in addition, not more than one of the $X^1$, $X^2$ and $X^3$ groups per cycle is N. More preferably, all $X^1$, $X^2$ and $X^3$ groups are $CR^4$.

Preferably, none of the $R^1$ radicals in the $A^1$, $A^2$, $A^3$, $A^4$ groups in the formulae (I) and/or (II) and none of the $R^5$, $R^6$ substituents which may be bonded directly or indirectly to an $R^1$ radical comprises a nitrogen atom.

In a further embodiment, none of the $R^2$ radicals in the $V^1$, $V^2$, $V^3$ groups in the formulae (I) and/or (II) and none of the $R^5$, $R^6$ substituents which may be bonded directly or indirectly to an $R^2$ radical comprises a nitrogen atom.

It may further be the case that none of the $R^3$ radicals in the $W^1$, $W^2$, $W^3$ groups in the formulae (I) and/or (II) and none of the $R^5$, $R^6$ substituents which may be bonded directly or indirectly to an $R^3$ radical comprises a nitrogen atom.

Preferably, none of the $R^4$ radicals in the $X^1$, $X^2$, $X^3$ groups in the formulae (I) and/or (II) and none of the $R^5$, $R^6$ substituents which may be bonded directly or indirectly to an $R^4$ radical comprises a nitrogen atom.

In addition, preference is given to compounds comprising structures of formula (I) and/or (II), and especially to compounds of the formula (I) and/or (II) having not more than 5 nitrogen atoms, preferably not more than 3 nitrogen atoms, particularly preferably not more than one nitrogen atom and especially preferably no nitrogen atom.

It may further be the case that compounds comprising structures of formula (I) and/or (II) have preferably not more than 5 heteroatoms, preferably not more than 3 heteroatoms, more preferably not more than one heteroatom and especially preferably no heteroatom, apart from fluorine.

Especially preferably, a compound comprising structures of formula (I) and/or (II), or a compound of formula (I) and/or (II), is a hydrocarbon or a fluorinated hydrocarbon, preferably a hydrocarbon.

In a preferred embodiment of the invention, the symbols $W^3$ and $V^3$ in formula (I) and/or (II) are each independently C—H, C-D and C—F. The symbols $W^2$ and $V^2$ in formula (II) may preferably each independently be C—H, C-D and C—F. In formula (I), the symbols $W^2$ and one of the symbols $V^2$ may each be C—H, C-D and C—F.

It may further be the case that the $R^1$ radicals in the $A^1$, $A^2$, $A^3$, $A^4$ groups in the formulae (I) and/or (II) do not form a fused ring system with the ring atoms of the fluorene structure. This also rules out the formation of a fused ring system with possible $R^5$, $R^6$ substituents which may be bonded to the $R^1$ radicals.

Preferably, the $R^2$ radicals in the $V^1$, $V^2$, $V^3$ groups do not form a fused ring system with the ring atoms of the phenyl group to which the $R^2$ radicals are bonded. This rules out the formation of a fused ring system with possible $R^5$, $R^6$ substituents which may be bonded to the $R^2$ radicals.

In a further preferred configuration, the $R^3$ radicals in the $W^1$, $W^2$, $W^3$ groups do not form a fused ring system with the ring atoms of the phenyl group to which the $R^3$ radicals are bonded. This also rules out the formation of a fused ring system with possible $R^5$, $R^6$ substituents which may be bonded to the $R^3$ radicals.

In addition, preference is given to compounds comprising structures of the formulae (I) and/or (II), and especially compounds of formula (I) and/or (II) which are characterized in that the $R^4$ radicals in the $X^1$, $X^2$, $X^3$ groups do not form a fused ring system with the ring atoms of the phenyl group to which the $R^4$ radicals are bonded. This also rules out the formation of a fused ring system with possible $R^5$, $R^6$ substituents which may be bonded to the $R^4$ radicals.

It may further be the case that a compound comprising structures of formula (I) and/or formula (II), or a compound of formula (I) and/or (II), is symmetric in relation to the mirror plane defined by the fluorene group. The mirror plane defined by the fluorene group encompasses all the carbon atoms of the fluorene group, and so the phenyl groups bonded to the carbon atom in the 9 position of the fluorene group have identical substitution.

In a further preferred embodiment, a compound comprising structures of formula (I) and/or formula (II), or a compound of formula (I) and/or (II), is unsymmetric in relation to the mirror plane defined by the fluorene group.

Accordingly, the phenyl groups bonded in the 9 position of the fluorene group preferably do not have identical substitution.

Preference is further given to compounds which can be represented by a structure of the formula (III)

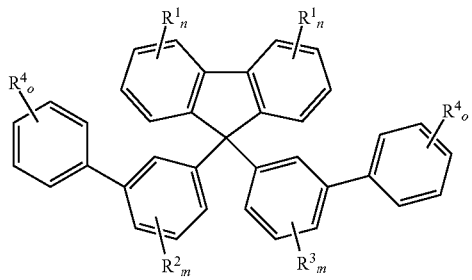

Formula (III)

where the $R^1$, $R^2$, $R^3$, $R^4$ symbols used are as defined above, especially for formula (I), and each m is independently 0 or 1, where the sum total of the indices m is not more than 1, each n is independently 0, 1, 2, 3 or 4, preferably 0, 1 or 2, particularly preferably 0 or 1 and especially preferably 0, and each o is independently 0, 1, 2, 3, 4 or 5, preferably 1, 2 or 3, particularly preferably 1 or 2.

Preferably, the sum total of the indices n in formula (III) may be not more than 2, more preferably not more than 1, this sum total especially preferably being 0. The sum total of the indices m in formula (III) is preferably 0, and so the phenyl radicals bonded to the fluorene group preferably do not comprise any additional substituents.

It may further be the case that the sum total of the indices o in formula (III) is at least 2, preferably 2, 3 or 4.

It may further be the case that the $R^1$ radicals in formula (III) do not form a fused ring system with the ring atoms of the fluorene structure. This also rules out the formation of a fused ring system with possible $R^5$, $R^6$ substituents which may be bonded to the $R^1$ radicals.

Preferably, the $R^2$ radicals in formula (III) do not form a fused ring system with the ring atoms of the phenyl group to which the $R^2$ radicals are bonded. This also rules out the formation of a fused ring system with possible $R^5$, $R^6$ substituents which may be bonded to the $R^2$ radicals.

In a further preferred configuration, the $R^3$ radicals in formula (III) do not form a fused ring system with the ring atoms of the phenyl group to which the $R^3$ radicals are bonded. This also rules out the formation of a fused ring system with possible $R^5$, $R^6$ substituents which may be bonded to the $R^3$ radicals.

In addition, preference is given to compounds which can be represented by a structure of the formula (III) which are characterized in that the $R^4$ radicals in formula (III) do not form a fused ring system with the ring atoms of the phenyl group to which the $R^4$ radicals are bonded. This also rules out the formation of a fused ring system with possible $R^5$, $R^6$ substituents which may be bonded to the $R^4$ radicals.

In addition, particular preference is given to compounds which can be represented by a structure of the formula (IV)

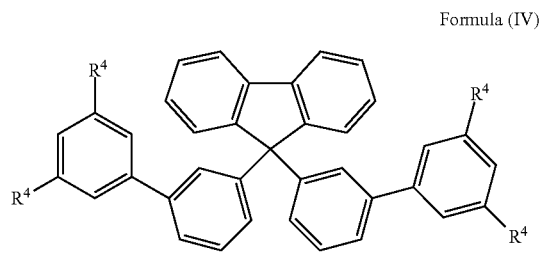

Formula (IV)

where the $R^4$ symbol used is as defined above, especially for formula (I). More preferably, the $R^4$ radicals do not have any nitrogen atom, especially preferably any heteroatom. Especially preferably, the $R^4$ radical may be an aromatic ring system, especially an aryl radical, or H.

In addition, preference is given to compounds which can be represented by a structure of the formula (IV) which are characterized in that the $R^4$ radicals in formula (IV) do not form a fused ring system with the ring atoms of the phenyl group to which the $R^4$ radicals are bonded. This also rules out the formation of a fused ring system with possible $R^5$, $R^6$ substituents which may be bonded to the $R^4$ radicals.

Preferably, not more than one and preferably none of the $R^4$ radicals in the formulae (III) and/or (IV) or one of the $R^5$, $R^6$ substituents which may be bonded directly or indirectly to an $R^4$ radical comprises a nitrogen atom.

Especially preferably, a compound which can be represented by a structure of formula (III) and/or (IV) is a hydrocarbon or a fluorinated hydrocarbon, preferably a hydrocarbon.

It may especially be the case that, in the structure of formula (I), (II), (III) and/or (IV), at least one $R^1$, $R^2$, $R^3$ and/or $R^4$ radical is a group selected from the formulae ($R^1$-1) to ($R^1$-45)

Formula ($R^1$-1)

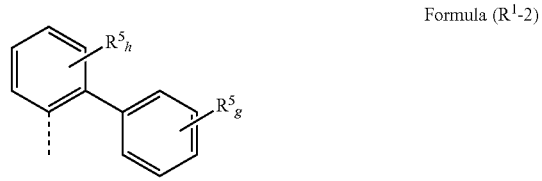

Formula ($R^1$-2)

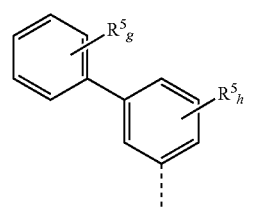
Formula (R¹-3)
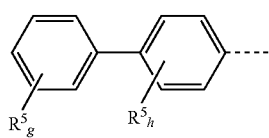
Formula (R¹-4)
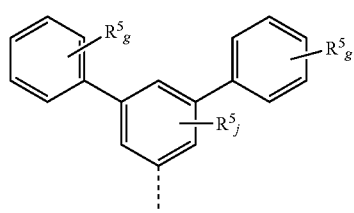
Formula (R¹-5)
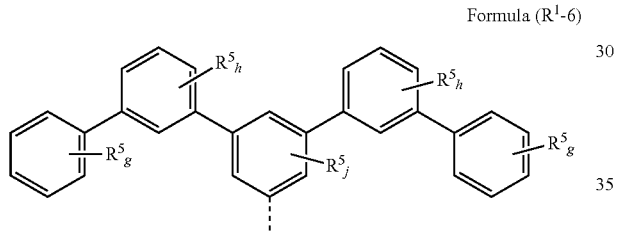
Formula (R¹-6)
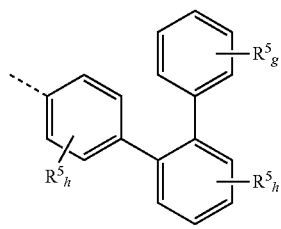
Formula (R¹-7)
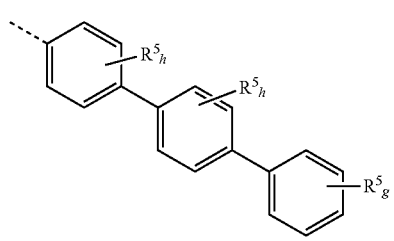
Formula (R¹-8)
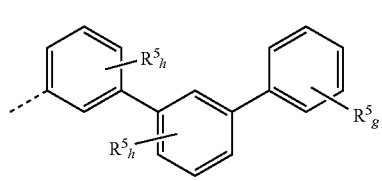
Formula (R¹-9)
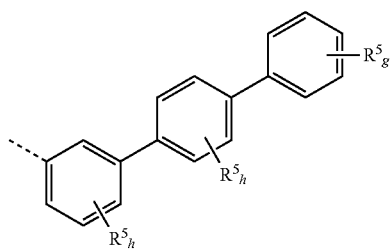
Formula (R¹-10)
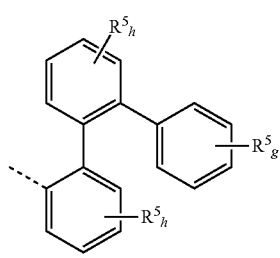
Formula (R¹-11)
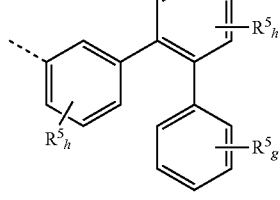
Formula (R¹-12)
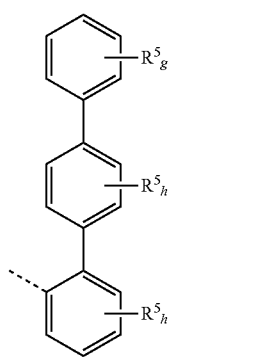
Formula (R¹-13)
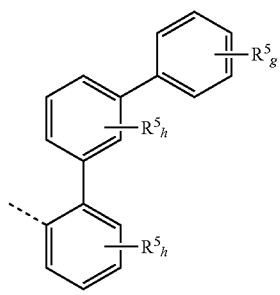
Formula (R¹-14)

Formula (R¹-15)
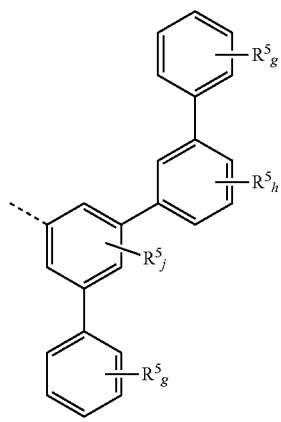
Formula (R¹-16)
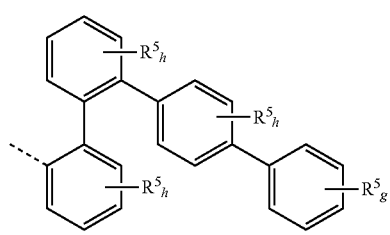
Formula (R¹-17)
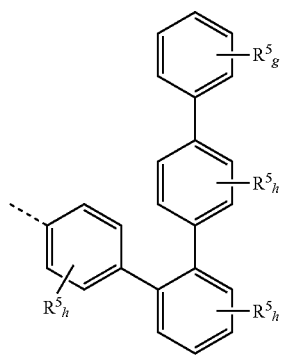
Formula (R¹-18)
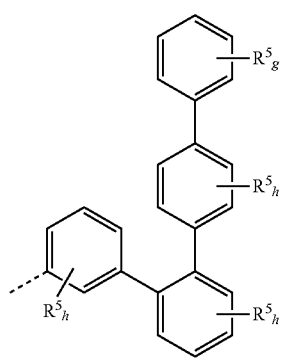
Formula (R¹-19)
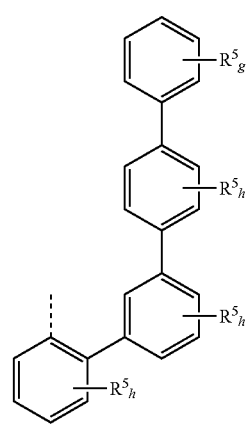
Formula (R¹-20)
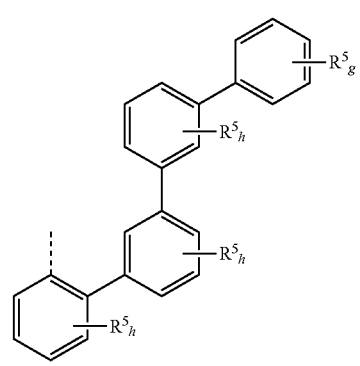
Formula (R¹-21)
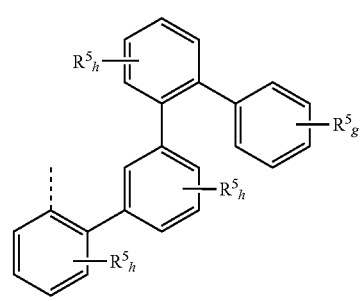
Formula (R¹-22)
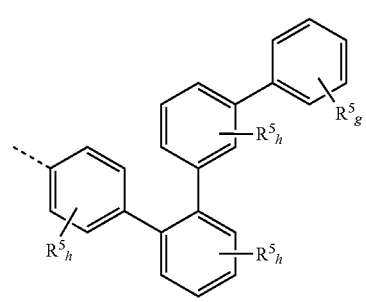
Formula (R¹-23)
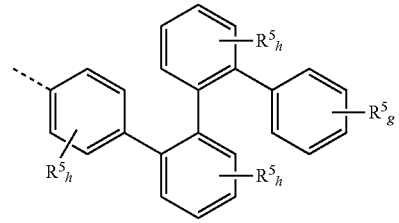

Formula (R¹-24)
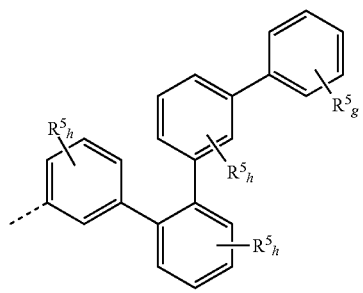
Formula (R¹-25)
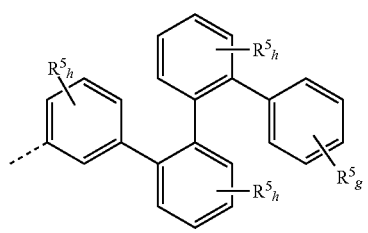
Formula (R¹-26)
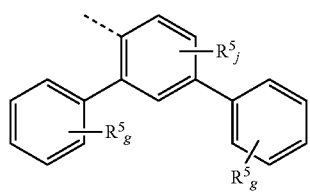
Formula (R¹-27)
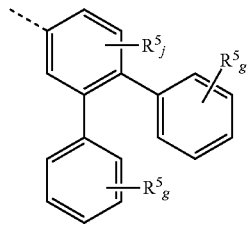
Formula (R¹-28)
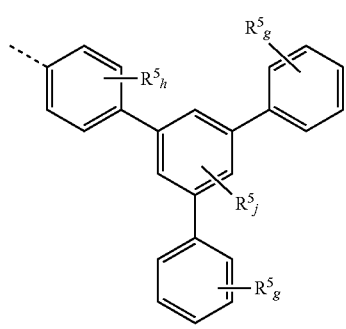
Formula (R¹-29)
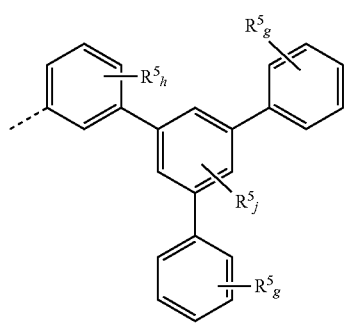
Formula (R¹-30)
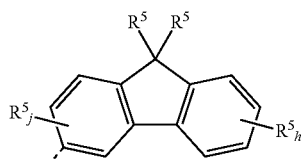
Formula (R¹-31)
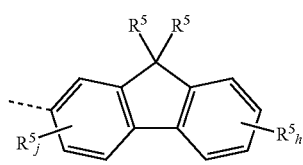
Formula (R¹-32)
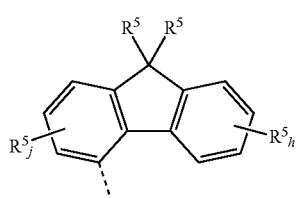
Formula (R¹-33)
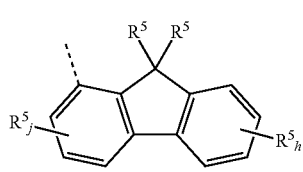
Formula (R¹-34)
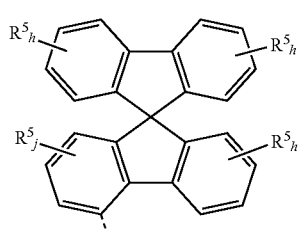
Formula (R¹-35)
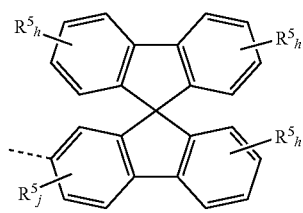
Formula (R¹-36)
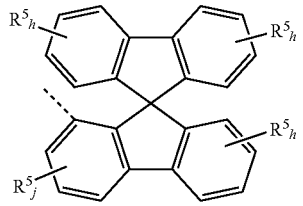

-continued

Formula (R¹-37)
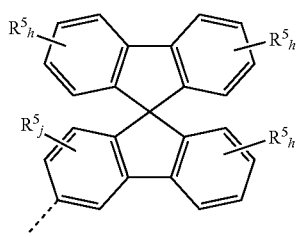

Formula (R¹-38)
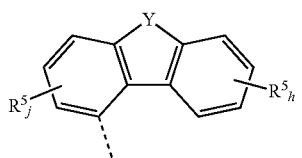

Formula (R¹-39)
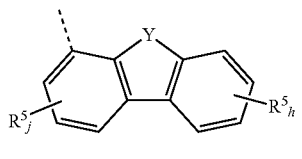

Formula (R¹-40)
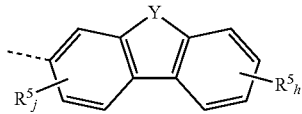

Formula (R¹-41)
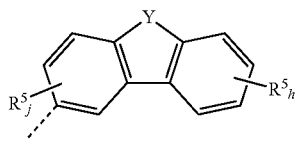

Formula (R¹-42)
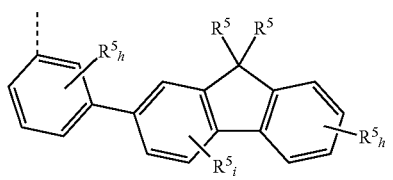

Formula (R¹-43)
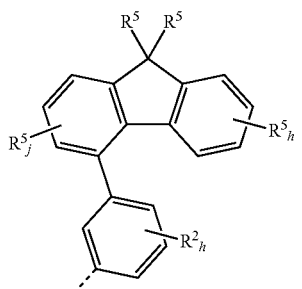

Formula (R¹-44)
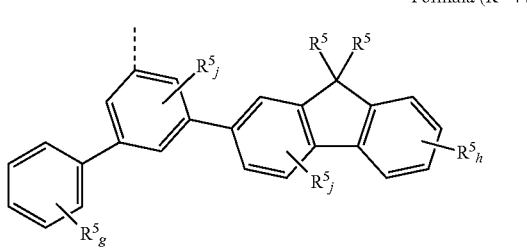

Formula (R¹-45)
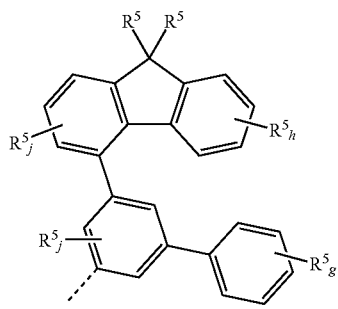

where the symbols used are as follows:
Y is O, S or $NR^5$;
j independently at each instance is 0, 1, 2 or 3;
h independently at each instance is 0, 1, 2, 3 or 4;
g independently at each instance is 0, 1, 2, 3, 4 or 5:
the dotted bond marks the attachment position; and
$R^5$ is as defined above, especially for formula (I).

More preferably, at least two of and especially preferably all of the $R^1$, $R^2$, $R^3$ and/or $R^4$ radicals in the structure of formula (I), (II), (III) and/or (IV) are H, D, F, an aliphatic hydrocarbon radical which has 1 to 20 carbon atoms and in which hydrogen atoms may also be replaced by F, or a group selected from the formulae ($R^1$-1) to ($R^1$-45).

Among the groups of the formulae ($R^1$-1) to ($R^1$-45) mentioned, preference is given to groups of the formulae ($R^1$-1) to ($R^1$-37) and ($R^1$-42) to ($R^1$-45). Among the groups of the formulae ($R^1$-1) to ($R^1$-45) mentioned, particular preference is further given to the groups of the formulae ($R^1$-1) to ($R^1$-33) and ($R^1$-42) to ($R^1$-45). Very particular preference is given to the groups of the formulae ($R^1$-1), ($R^1$-3), ($R^1$-5), ($R^1$-6), ($R^1$-15), ($R^1$-29), ($R^1$-31), ($R^1$-32), ($R^1$-42), ($R^1$-43), ($R^1$-44) and/or ($R^1$-45).

It may further be the case that the sum total of the indices g, h and j in the structures of the formula ($R^1$-1) to ($R^1$-45) is not more than 3 in each case, preferably not more than 2 and more preferably not more than 1. Most preferably, the sum total of the indices g, h and j in each of the structures of the formula ($R^1$-1) to ($R^1$-45) is 0.

It may especially be the case that, in the structure of formula (I), (II), (III) and/or (IV), at least one $R^5$ radical is a group selected from aliphatic hydrocarbyl radicals having 1 to 20 carbon atoms and in which hydrogen atoms may also be replaced by F. In this context, the $R^5$ radicals preferably do not comprise any $R^6$ substituents.

It may further be the case that, in the structures of the formula ($R^1$-1) to ($R^1$-45), the $R^5$ radical is H, F or a group selected from aliphatic hydrocarbyl radicals having 1 to 20 carbon atoms and in which hydrogen atoms may also be replaced by F. In this context, the $R^5$ radicals preferably do not comprise any $R^6$ substituents.

In a particular embodiment, a compound comprising structures of formula (I) and/or (II) or one which can be represented by structures of formula (I), (II), (III) and/or (IV) has a glass transition temperature of at least 70° C., more preferably of at least 110° C., even more preferably of at least 125° C. and especially preferably of at least 150° C., determined in accordance with DIN EN ISO 11357-1 and DIN EN ISO 11357-2.

Examples of preferred compounds of the formulae (I) to (IV) are the structures (1) to (46) depicted below.

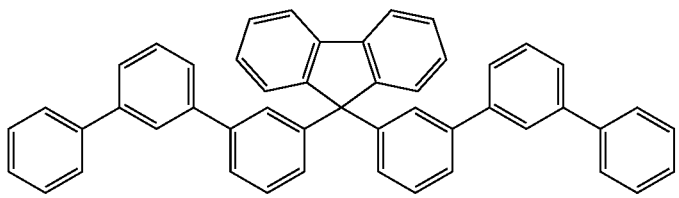
(1)
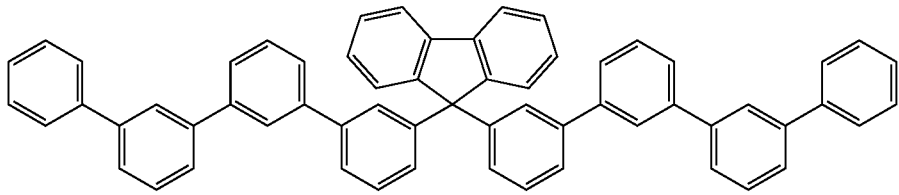
(2)
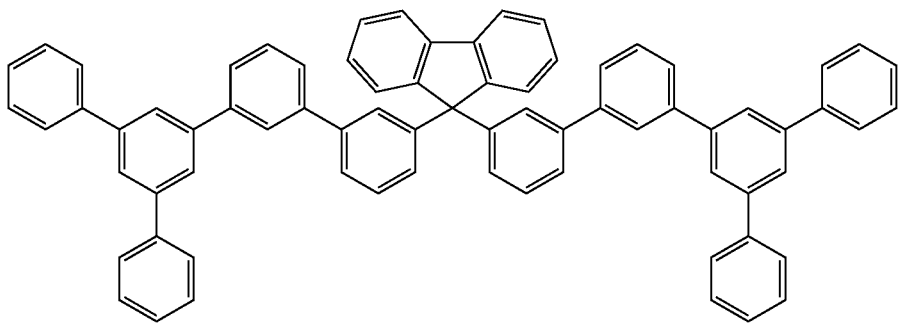
(3)
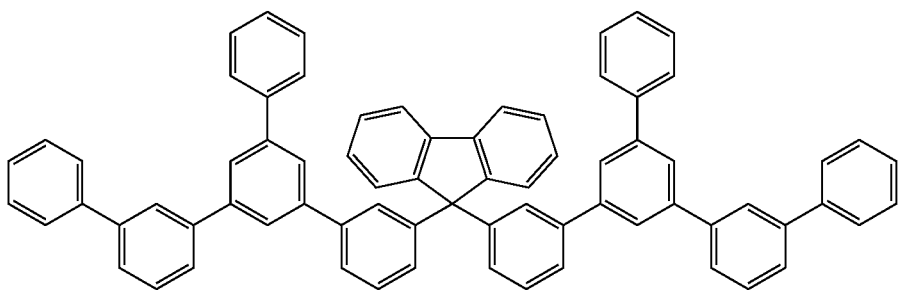
(4)
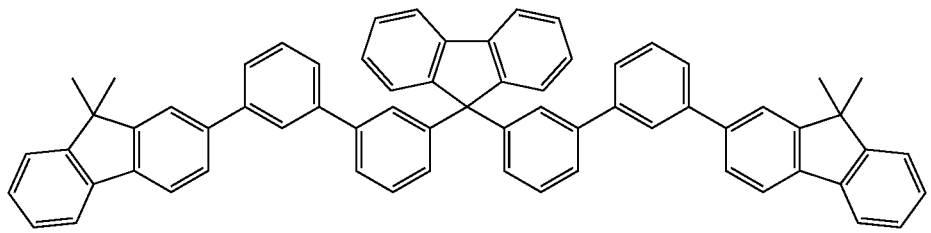
(5)
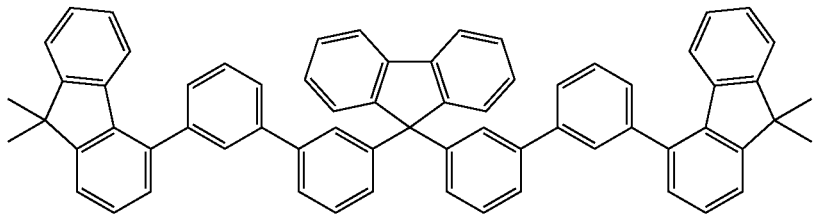
(6)

-continued
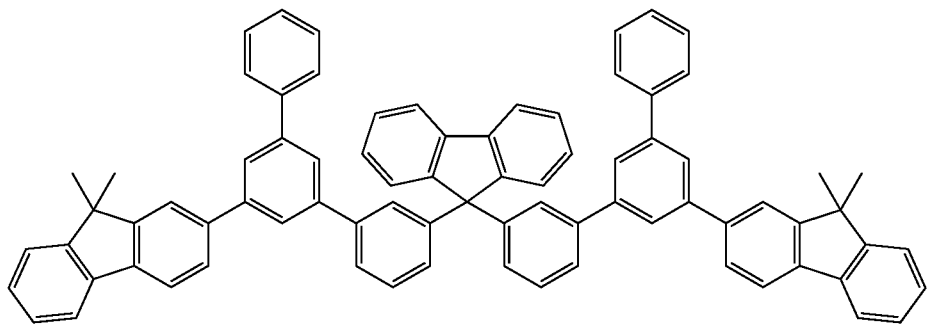
(7)
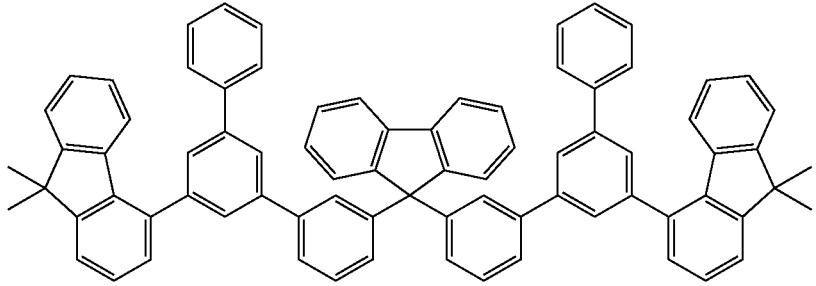
(8)
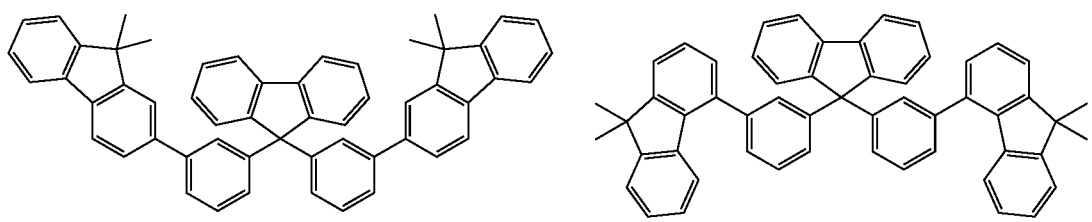
(9) (10)
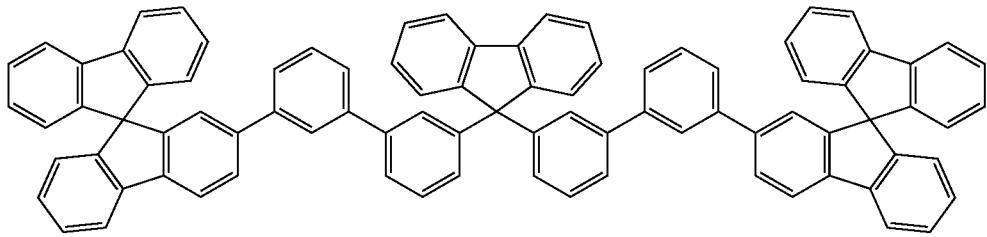
(11)
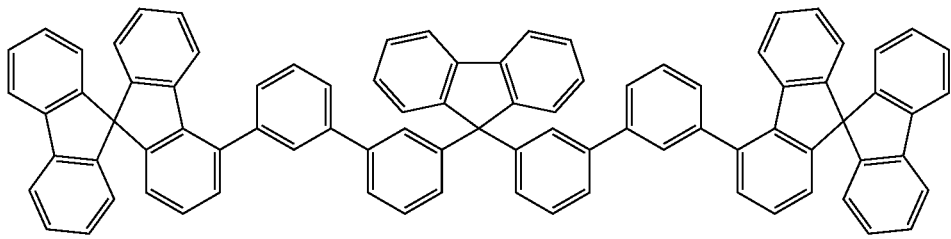
(12)
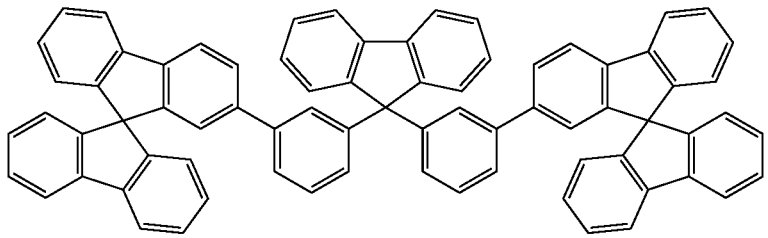
(13)

-continued
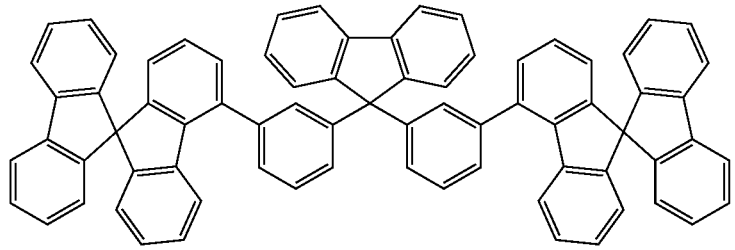
(14)
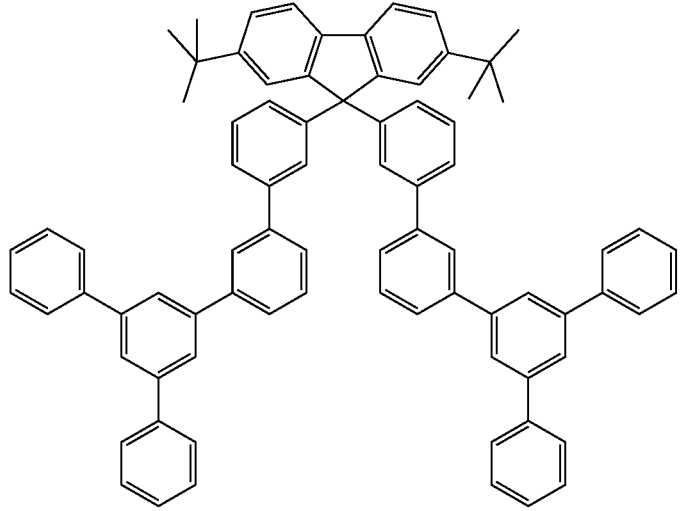
(15)
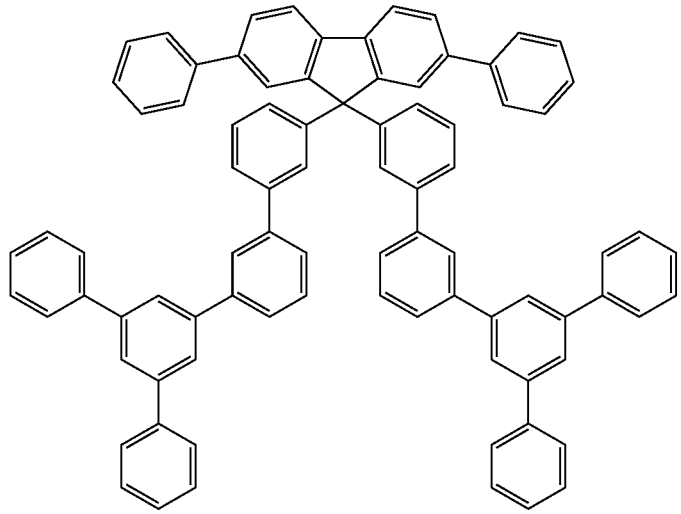
(16)
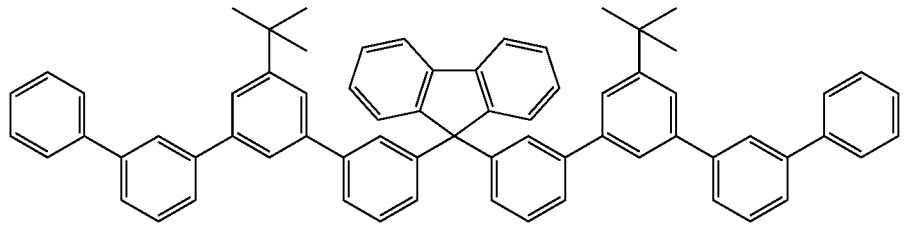
(17)

-continued
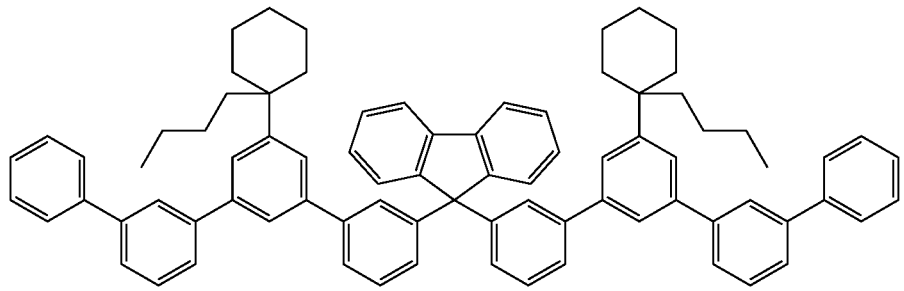
(18)
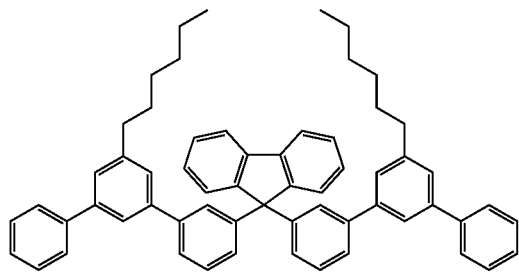
(19)
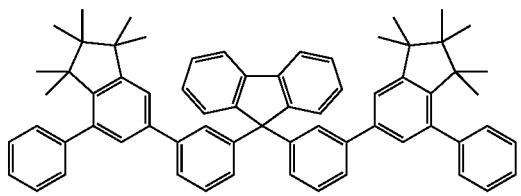
(20)
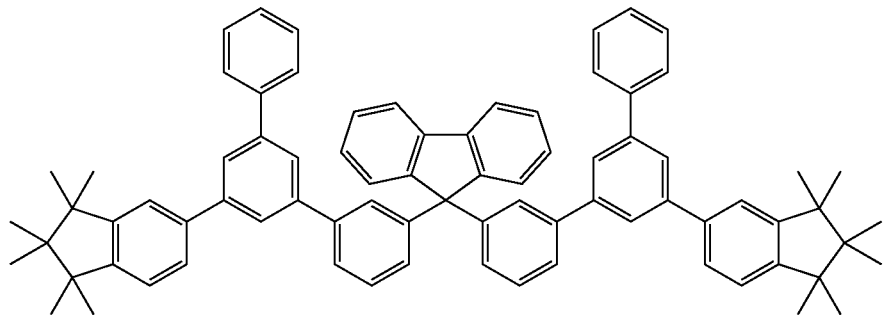
(21)
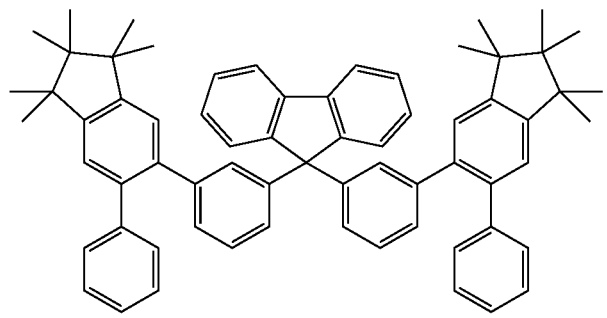
(22)
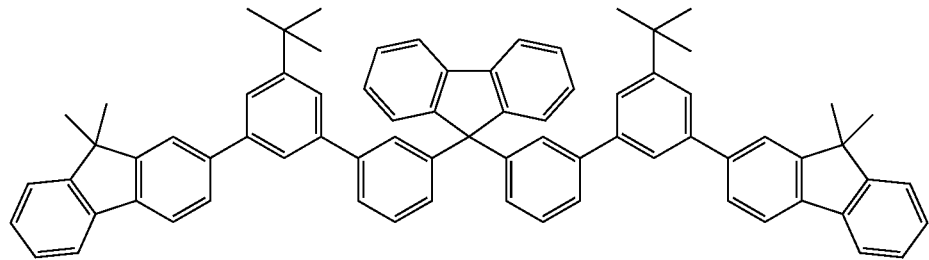
(23)

-continued
(24)
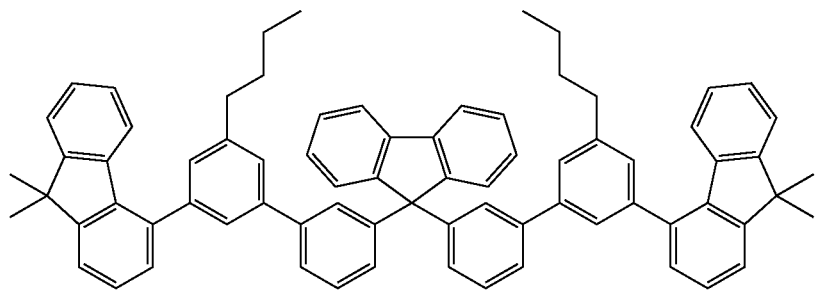
(25)
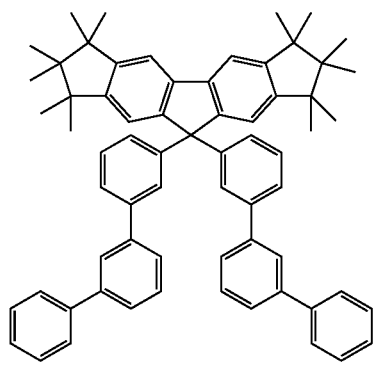
(26)
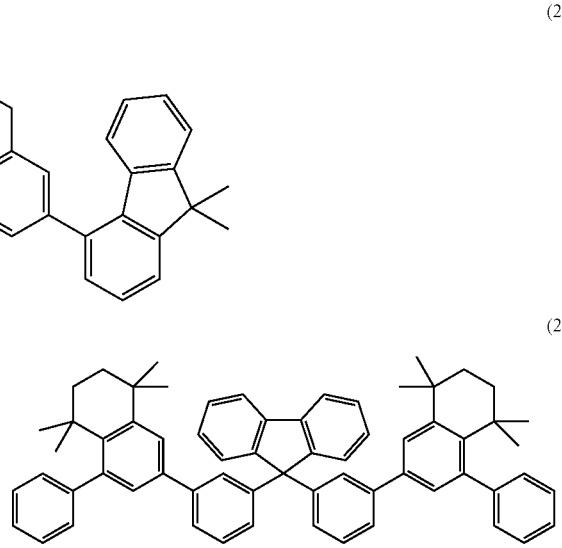
(27)
(28)
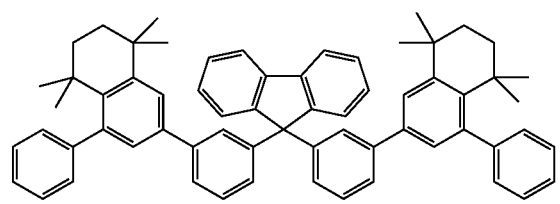
(29)
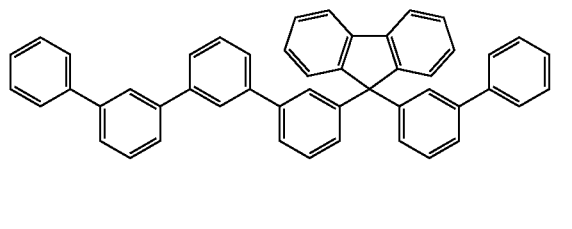
(30)
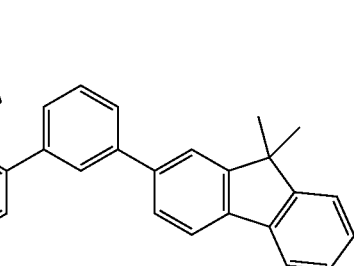

(31)
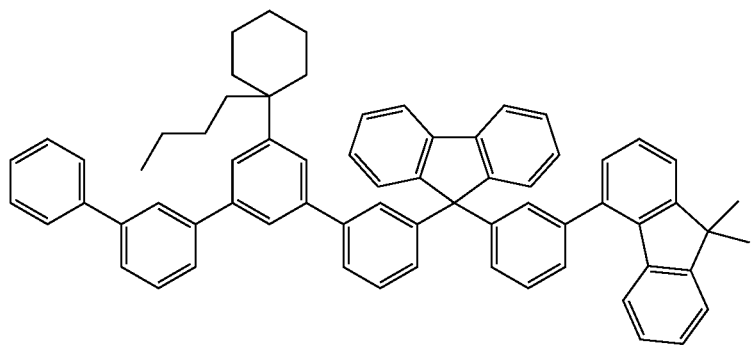
(32)
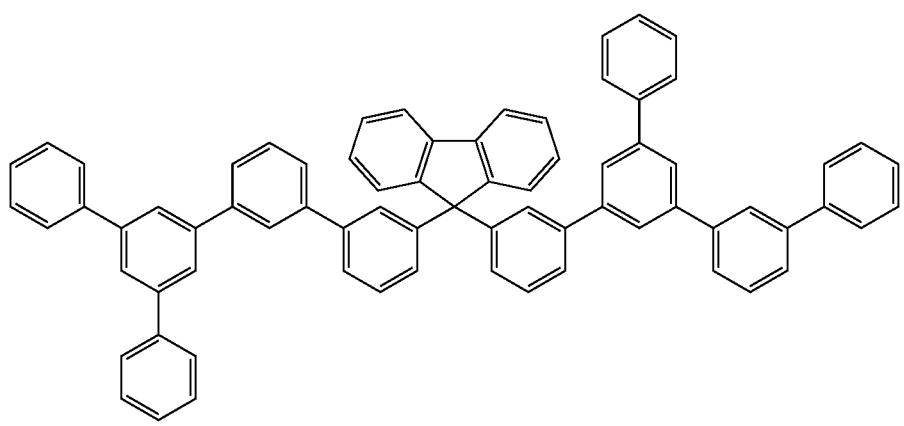
(33)
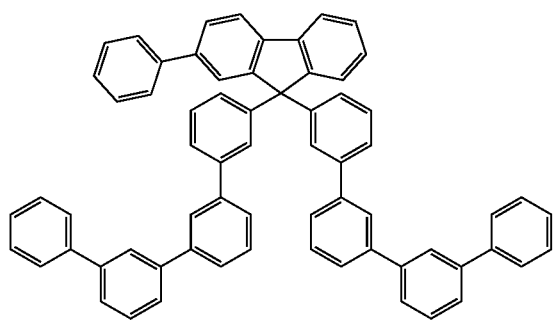
(34)
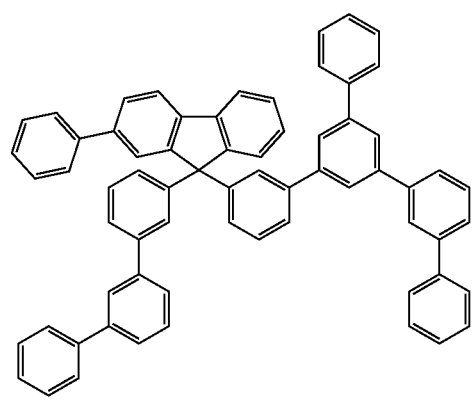
(35)
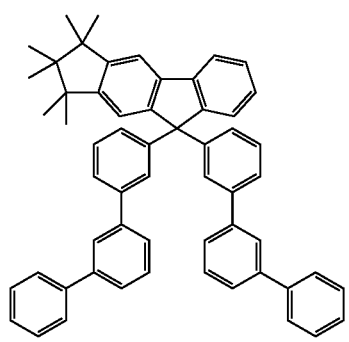
(36)
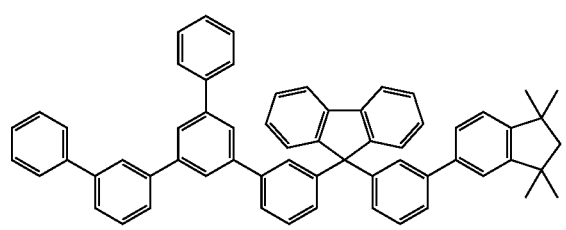

-continued
(37)
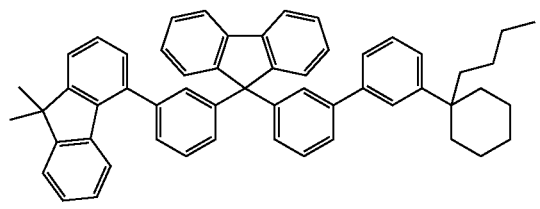
(38)
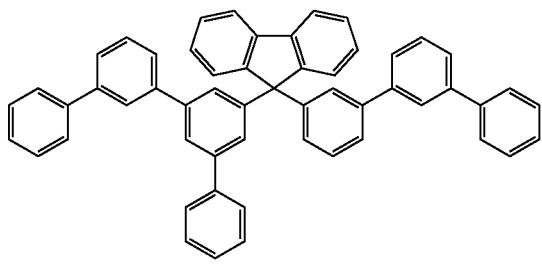
(39)
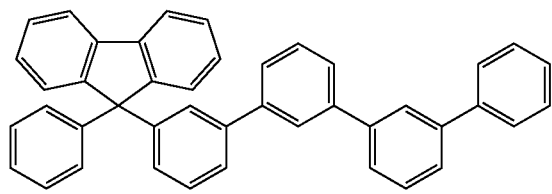
(40)
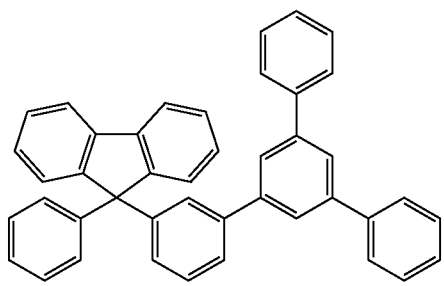
(41)
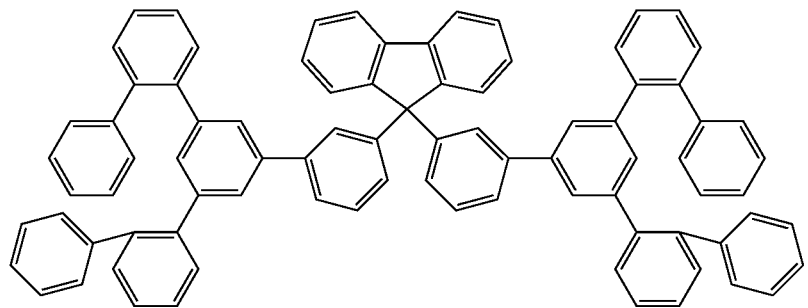
(42)
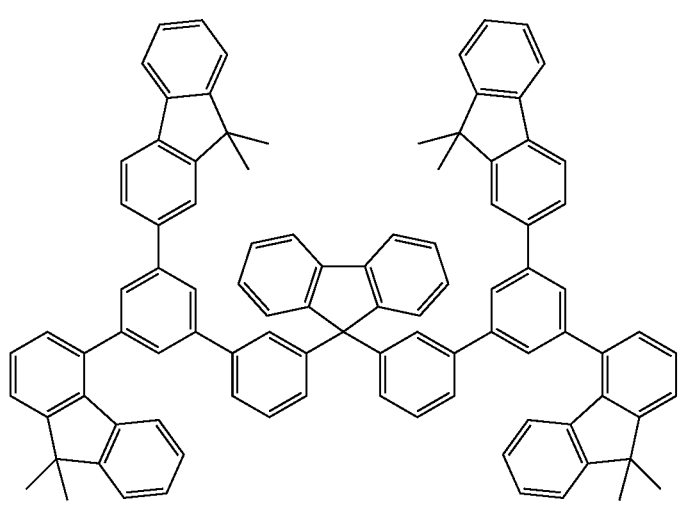

-continued
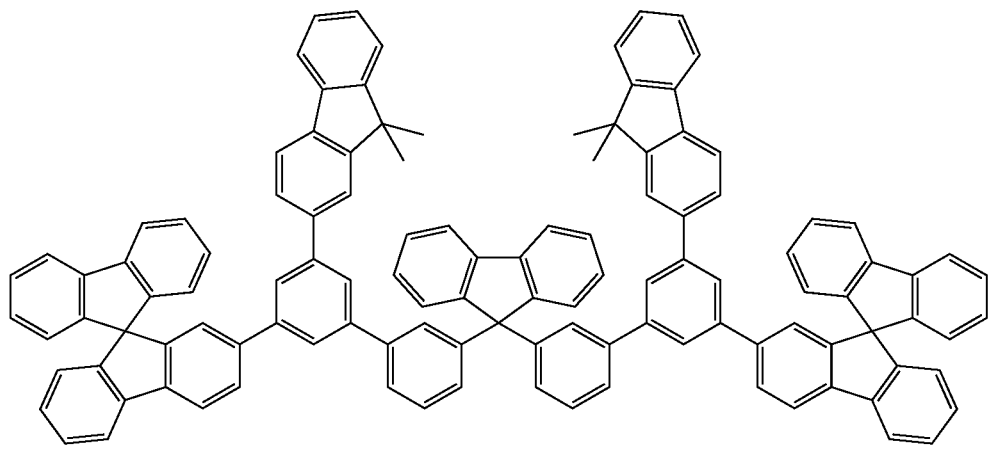
(43)
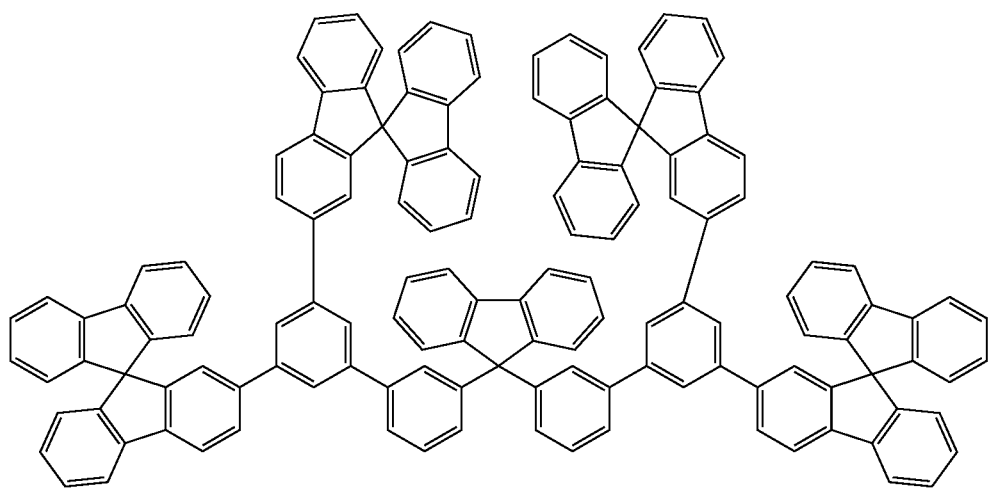
(44)
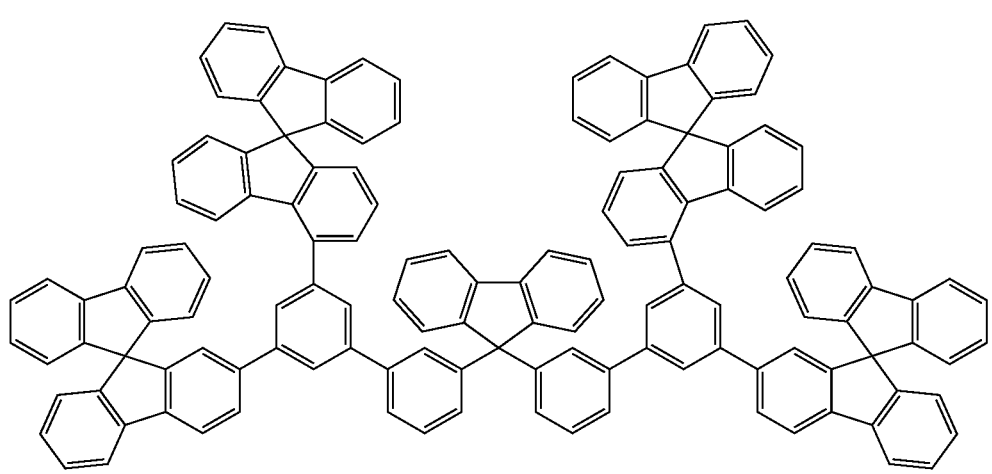
(45)

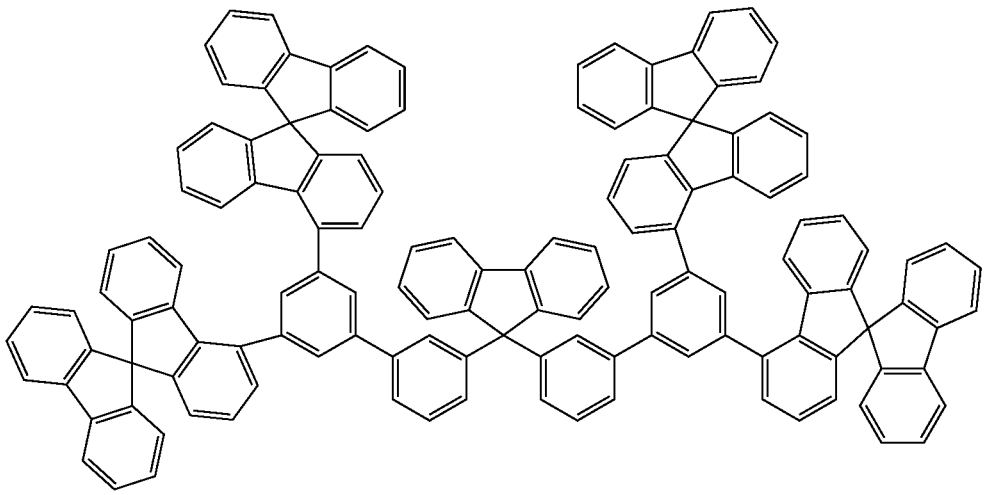

(46)

More preferably, a compound comprising structures of formula (I) and/or formula (II) or one which can be represented by structures of the formula (I), (II), (III) and/or formula (IV) may be a wide band gap material.

Preferably, a compound comprising structures of formula (I) and/or formula (II) or one which can be represented by structures of the formula (I), (II), (III) and/or formula (IV) may have a band gap of 2.5 eV or more, preferably 3.0 eV or more, very preferably of 3.5 eV or more. A "wide band gap" material in the context of the present invention refers to a material having a band gap of 3.0 eV or more. One way of calculating the band gap is via the energy levels of the highest occupied molecular orbital (HOMO) and the lowest unoccupied molecular orbital (LUMO).

The HOMO and LUMO energies and the triplet level and the singlet levels of the materials are determined via quantum-chemical calculations. For this purpose, in the present case, the "Gaussian09, Revision D.01" software package (Gaussian Inc.) is used. For calculation of organic substances without metals (referred to as the "org." method), a geometry optimization is first conducted by the semi-empirical method AM1 (Gaussian input line "# AM1 opt") with charge 0 and multiplicity 1. Subsequently, on the basis of the optimized geometry, a single-point energy calculation is effected for the electronic ground state and the triplet level. This is done using the TDDFT (time dependent density functional theory) method B3PW91 with the 6-31G(d) basis set (Gaussian input line "# B3PW91/6-31G(d) td=(50-50, nstates=4)") (charge 0, multiplicity 1). For organometallic compounds (referred to as the "M-org." method), the geometry is optimized by the Hartree-Fock method and the LanL2 MB basis set (Gaussian input line "#HF/LanL2 MB opt") (charge 0, multiplicity 1). The energy calculation is effected, as described above, analogously to that for the organic substances, except that the "LanL2DZ" basis set is used for the metal atom and the "6-31G(d)" basis set for the ligands (Gaussian input line "#B3PW91/gen pseudo=lanl2 td=(50-50,nstates=4)"). From the energy calculation, the HOMO is obtained as the last orbital occupied by two electrons (alpha occ. eigenvalues) and LUMO as the first unoccupied orbital (alpha virt. eigenvalues) in Hartree units, where HEh and LEh represent the HOMO energy in Hartree units and the LUMO energy in Hartree units respectively. This is used to determine the HOMO and LUMO value in electron volts, calibrated by cyclic voltammetry measurements, as follows:

HOMO(eV)=(HEh*27.212)*0.8308−1.118

LUMO(eV)=(LEh*27.212)*1.0658−0.5049

These values are to be regarded as HOMO and as LUMO of the materials in the context of this application. The magnitude of the difference between the two values is regarded as the band gap in the context of this application.

The triplet level T1 of a material is defined as the relative excitation energy (in eV) of the triplet state having the lowest energy which is found by the quantum-chemical energy calculation.

The singlet level S1 of a material is defined as the relative excitation energy (in eV) of the singlet state having the second-lowest energy which is found by the quantum-chemical energy calculation.

The energetically lowest singlet state is referred to as S0.

The method described herein is independent of the software package used. Examples of frequently utilized programs for this purpose are "Gaussian09" (Gaussian Inc.) and Q-Chem 4.1 (Q-Chem, Inc.). In the present case, the energies are calculated using the software package "Gaussian09, Revision D.01" with the pre-programmed set of parameters.

The compounds of the invention, comprising structures of formula (I) and/or (II), or which can be represented by the formulae (I), (II), (III) or (IV), can be prepared by synthesis steps that are common knowledge to those skilled in the art. The starting compound used may, for example, be 3,3'-dibromobenzophenone (J. Mater. Chem. C 2014, 2028-2036). This can, for example, be converted according to Scheme 1 by reaction with a substituted or unsubstituted 2-lithiobiphenyl to give the corresponding triarylmethanols, which are then cyclized under acidic conditions, for example in the presence of acetic acid and a mineral acid such as hydrogen bromide. The organolithium compounds required for this reaction can be prepared by transmetallation of the corresponding 2-bromobiphenyl compounds with alkyllithium compounds such as n-butyllithium. In an analogous manner, it is of course possible to use corresponding Grignard compounds.

Scheme 1

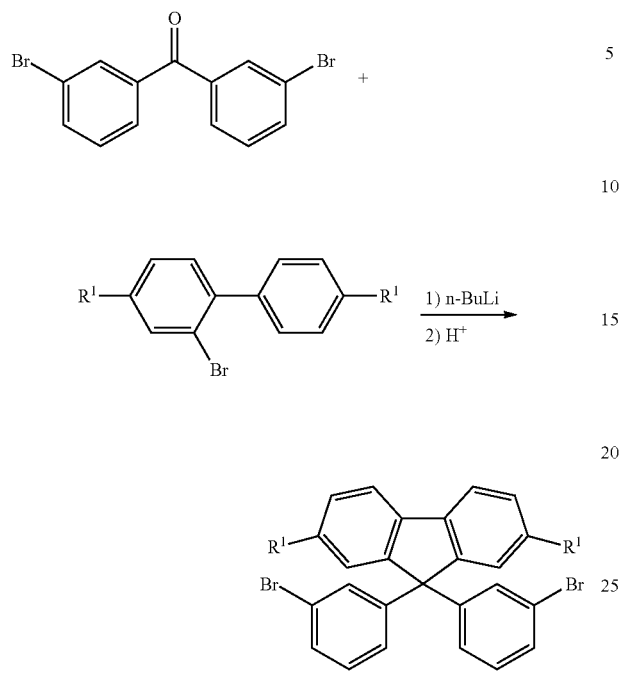

The dibromides thus obtained can be converted further by methods known to those skilled in the art. For example, the palladium-catalysed reaction with boronic acids (Suzuki coupling) or the palladium-catalysed reaction with organotin compounds (Negishi coupling) leads to aromatic or heteroaromatic compounds of the invention. According to Scheme 2, by reaction of a dibromide with two equivalents, it is possible to prepare symmetrically substituted 9,9-diphenylfluorenes. According to Schemes 3 and 4, it is possible in an analogous manner to obtain mixtures of three products, one of which in each case is asymmetrically substituted with respect to the 9,9-diphenylfluorene. These mixtures can then be separated by chromatography.

Scheme 2

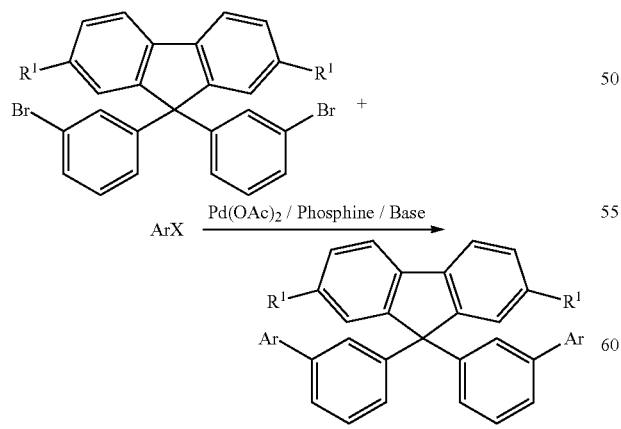

Ar = (hetero)aromatic hydrocarbon
X = B(OH)$_2$, ZnBr, MgBr, etc.

Scheme 3

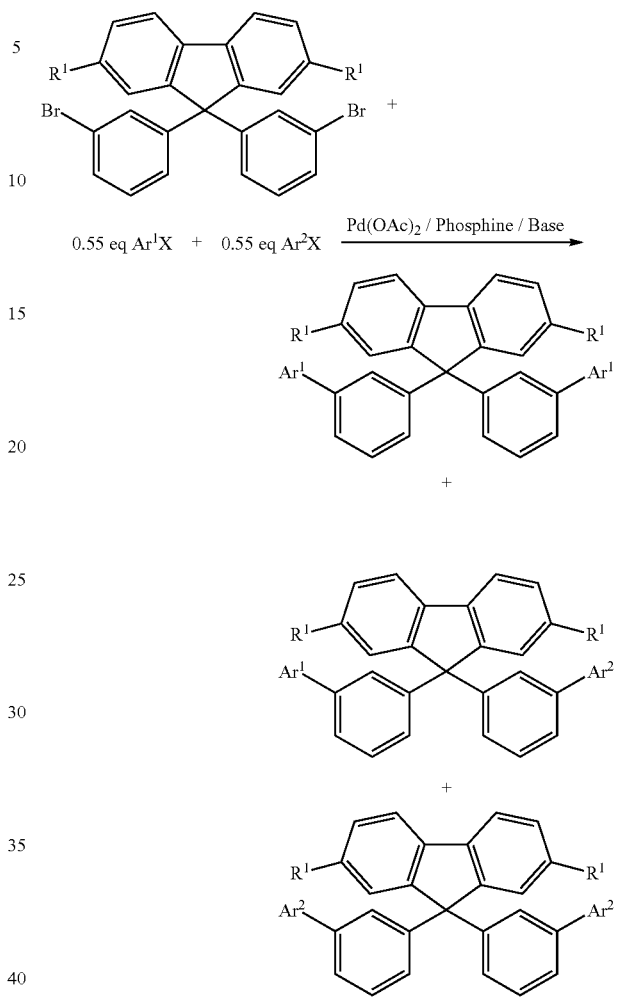

Ar = (hetero)aromatic hydrocarbon
X = B(OH)$_2$, ZnBr, MgBr, etc.

Scheme 4

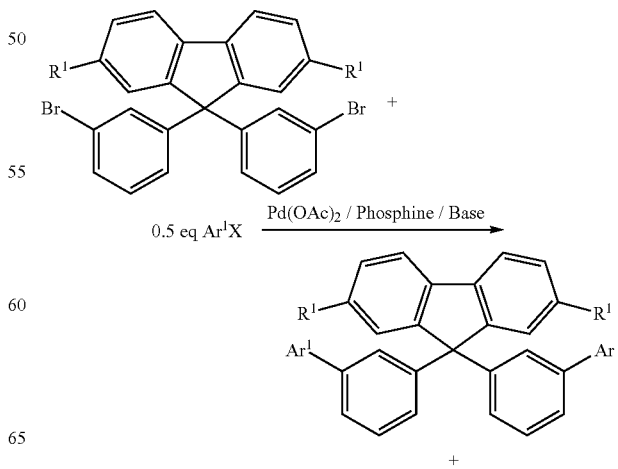

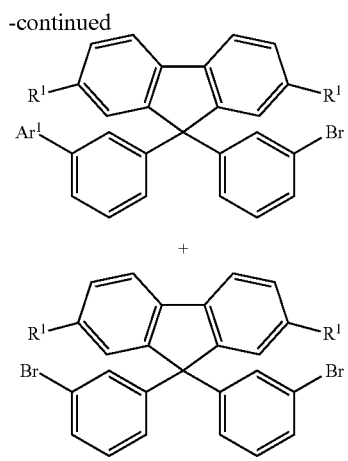

Ar = (hetero)aromatic hydrocarbon
X = B(OH)$_2$, ZnBr, MgBr, etc.

The monobromo compound formed according to Scheme 4 can be substituted further, for example, by another coupling reaction. In addition, it is possible to convert a remaining bromine group according to Scheme 5 to a hydrogen radical by transmetallation, for example with an organolithium compound such as n-butyllithium, and subsequent reaction with a proton source such as water.

Scheme 5

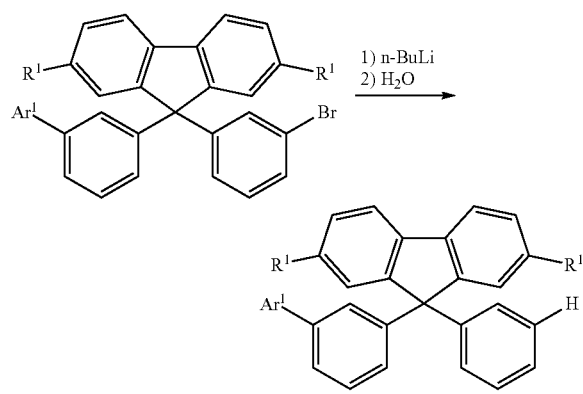

The invention further provides a process for preparing the compounds comprising structures of formula (I) and/or (II), or ones which can be represented by the formulae (I), (II), (III) or (IV), comprising the reaction of 3,3'-dibromobenzophenone with a substituted or unsubstituted 2-lithiobiphenyl or the corresponding Grignard compound to give the triarylmethanols, followed by cyclization under acidic conditions and optionally followed by further conversion of the bromine groups.

The present invention still further provides a composition comprising a compound of the invention and at least one further organically functional material. The further organically functional material differs from the compounds of the invention. Functional materials are generally the organic or inorganic materials introduced between the anode and cathode. Preferably, the organically functional material is selected from the group consisting of fluorescent emitters, phosphorescent emitters, host materials, matrix materials, electron transport materials, electron injection materials, hole conductor materials, hole injection materials, electron blocker materials and hole blocker materials.

The present invention further provides a composition comprising at least one compound comprising at least one structure of formula (I) or the preferred embodiments detailed above and hereinafter, and at least one emitter and at least one compound selected from the group consisting of electron transport materials and hole conductor materials. Emitters include fluorescent emitters and phosphorescent emitters, and it is also possible to use mixtures of fluorescent emitters and phosphorescent emitters. Preference is given to phosphorescent emitters.

The present invention still further provides solutions comprising at least one compound comprising at least one structure of formula (I) or the preferred embodiments and at least one organic solvent. Solutions of this kind are required for the production of the organic electronic device from solution, for example by spin-coating or by printing methods.

For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, hexamethylindane, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention therefore further provides a formulation comprising at least one compound comprising at least one structure of formula (I) or as per the preferred embodiments and one or more solvents, especially organic solvents. This formulation preferably comprises solutions, suspensions or miniemulsions, especially solutions. The way in which such solutions can be prepared is known to those skilled in the art and is described, for example, in WO 02/072714, WO 03/019694 and the literature cited therein.

The compounds of the invention, comprising at least one structure of formula (I) or as per the preferred embodiments, are suitable for use in electronic devices, especially in organic electroluminescent devices (OLEDs, PLEDs). Depending on the substitution, the compounds are used in different functions and layers. In this case, the preferred embodiments correspond to the abovementioned formulae.

The invention therefore further provides for the use of compounds comprising structures of formula (I) and/or (II) or ones which can be represented by structures of formula (I), (II), (III) and/or (IV) in electronic devices, especially in organic electroluminescent devices.

The invention still further provides for the use of compounds comprising structures of formula (I) and/or (II) or ones which can be represented by structures of formula (III)

and/or (IV) in electronic devices, especially in organic electroluminescent devices, especially as a wide band gap material.

The invention further provides an electronic device comprising at least one compound comprising structures of formula (I) and/or (II) or one which can be represented by structures of formula (III) and/or (IV), wherein the electronic device is preferably selected from the group consisting of organic electroluminescent devices (OLEDs, PLEDs), organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) or organic photoreceptors.

The invention still further provides organic electronic devices comprising at least one compound comprising structures of formula (I) and/or (II) or which can be represented by structures of formula (III) and/or (IV), especially organic electroluminescent devices comprising anode, cathode and at least one emitting layer, characterized in that at least one organic layer which may be an emitting layer or another layer comprises at least one compound comprising structures of formula (I) and/or (II) or ones which can be represented by structures of formula (III) and/or (IV).

In addition, the invention further provides an organic electroluminescent device comprising an emitting layer comprising at least one compound of the invention comprising structures of formulae (I) and/or (II) or ones which can be represented by formulae (III) and/or (IV), and at least one phosphorescent emitter and at least one matrix material which differs from the compounds of the invention. Preferably, the further matrix material may be a hole- and/or electron-conducting matrix material, it being particularly preferable to use a "bipolar" matrix material having both hole-conducting and electron-conducting properties. More preferably, the compound of the invention has the properties of a wide band gap material and the further matrix material is hole- and/or electron-conducting.

Apart from the cathode, anode and emitting layer, the organic electroluminescent device may also comprise further layers. These are selected, for example, from in each case one or more hole injection layers, hole transport layers, hole blocker layers, electron transport layers, electron injection layers, electron blocker layers, exciton blocker layers, charge generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. In addition, the layers, especially the charge transport layers, may also be doped. The doping of the layers may be advantageous for improved charge transport. However, it should be pointed out that not every one of these layers need necessarily be present and the choice of layers always depends on the compounds used and especially also on whether the device is a fluorescent or phosphorescent electroluminescent device.

In a further preferred embodiment of the invention, the organic electroluminescent device comprises two or more emitting layers, at least one organic layer comprising at least one compound comprising at least one structure of formula (I) or one of the preferred compounds detailed above. More preferably, these emission layers have several emission maxima between 380 nm and 750 nm overall, such that the overall result is white emission; in other words, various emitting compounds which may fluoresce or phosphoresce and which emit blue and yellow, orange or red light are used in the emitting layers. Especially preferred are three-layer systems, i.e. systems having three emitting layers, where at least one of these layers comprises at least one compound comprising at least one structure of formula (I) and where the three layers show blue, green and orange or red emission (for the basic construction see, for example, WO 05/011013). Emitters likewise suitable for white emission are those which have broad emission bands and as a result exhibit white emission.

In a preferred embodiment of the invention, the compounds comprising at least one structure of formula (I) or as per the preferred embodiments are used as matrix material for fluorescent or phosphorescent compounds in an emitting layer. In a matrix material for fluorescent compounds, preferably one or more $R^1$, $R^2$, $R^3$ and/or $R^4$ groups are an aromatic or heteroaromatic ring system, especially an aromatic ring system containing anthracene. The same preferences apply to the $R^1$, $R^2$, $R^3$ and/or $R^4$ groups in structures of the abovementioned formulae.

A matrix material in a system composed of matrix and dopant is understood to mean that component present in a higher proportion in the system. In a system composed of a matrix and two or more dopants, the matrix is understood to mean that component having the highest proportion in the mixture.

In a preferred embodiment of the invention, the matrix used is a mixture, wherein at least one component of this mixture is a compound of the formula (I) or as per the preferred embodiments. Preferably, one component of this mixture is a hole transport compound and the other an electron transport compound. Preferred hole transport compounds are aromatic amines and carbazole derivatives. Preferred electron transport compounds are triazine derivatives.

In one embodiment, the compound comprising at least one structure of formula (I) or as per the preferred embodiments is used as the sole matrix material in the mixture with the emitter. In a further embodiment of the invention, the compound comprising at least one structure of formula (I) or as per the preferred embodiments is used in the form of a mixture together with a further matrix material and an emitter. Preferably, one component of this mixture of matrix materials is a hole transport compound and the other an electron transport compound. Especially preferably, one component of this mixture of matrix materials comprises a wide band gap material comprising at least one structure of formula (I) or as per the preferred embodiments.

Preferred electron-conducting compounds which can be used together with a compound comprising at least one structure of formula (I) include those described in WO 2014/094964, particularly preferred electron-conducting compounds having a LUMO of ≤−2.4 eV.

Examples of suitable electron-conducting compounds having a LUMO ≤−2.4 eV are the compounds depicted in the following table:

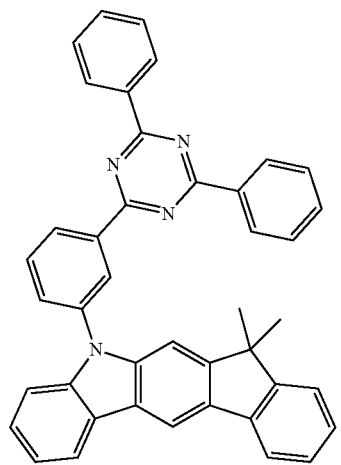 [SMILES: CC1(C)c2ccccc2-c2cc3c4ccccc4n(-c4cccc(-c5nc(-c6ccccc6)nc(-c6ccccc6)n5)c4)c3cc21]
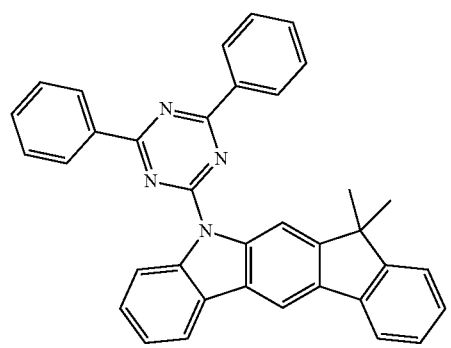 [SMILES: CC1(C)c2ccccc2-c2cc3c4ccccc4n(-c4nc(-c5ccccc5)nc(-c5ccccc5)n4)c3cc21]
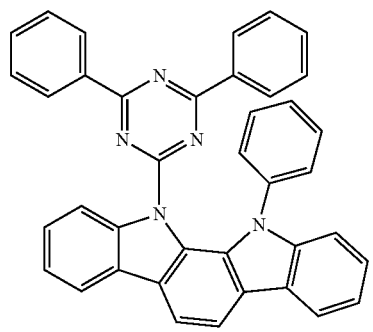 [SMILES: c1ccc(-c2nc(-c3ccccc3)nc(-n3c4ccccc4c4ccc5c6ccccc6n(-c6ccccc6)c5c43)n2)cc1]
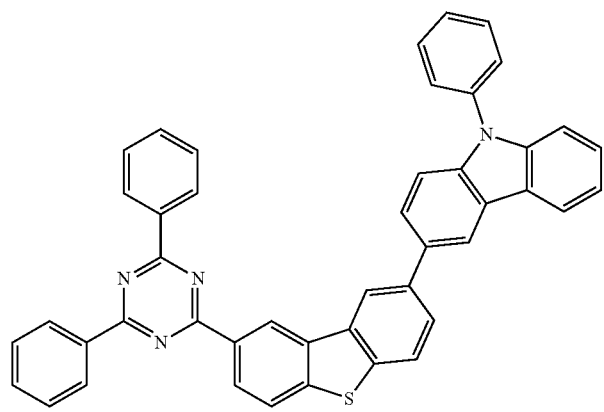 [SMILES: c1ccc(-c2nc(-c3ccccc3)nc(-c3ccc4sc5ccc(-c6ccc7c(c6)c6ccccc6n7-c6ccccc6)cc5c4c3)n2)cc1]

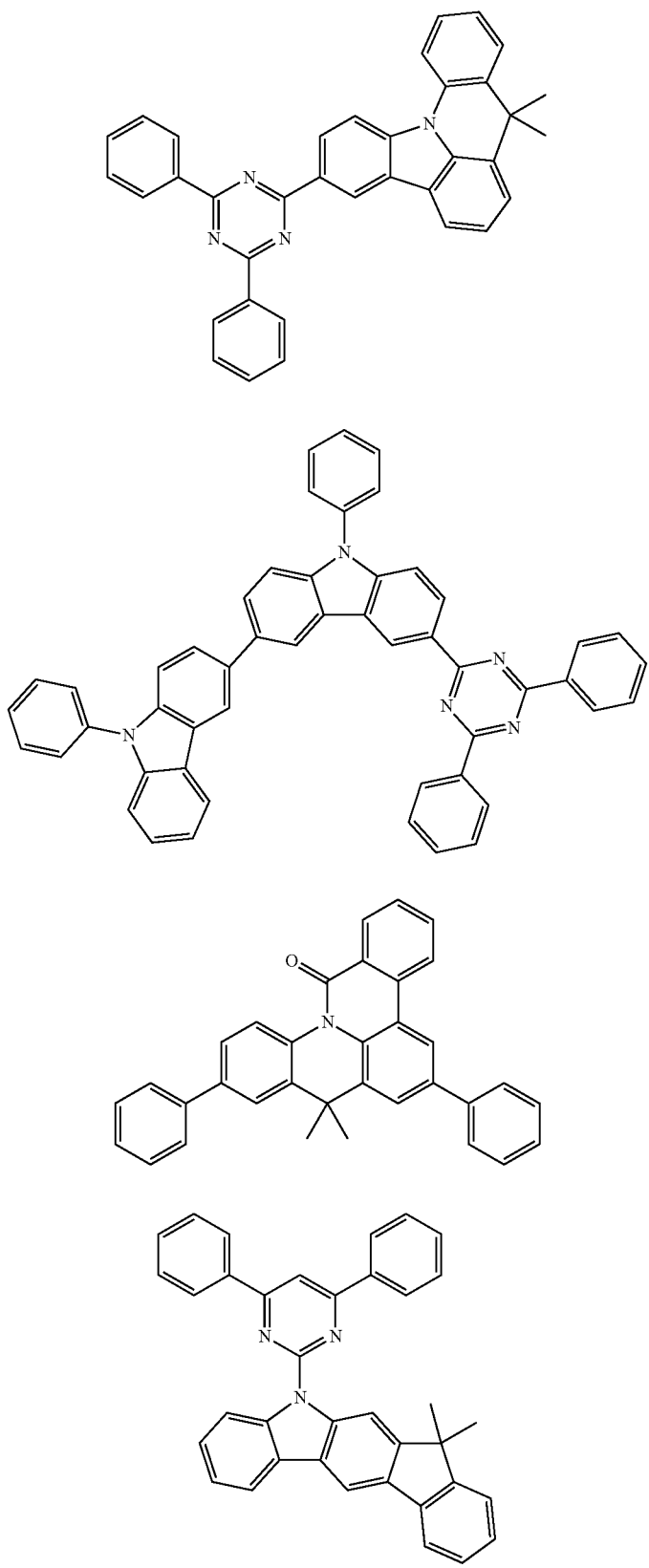

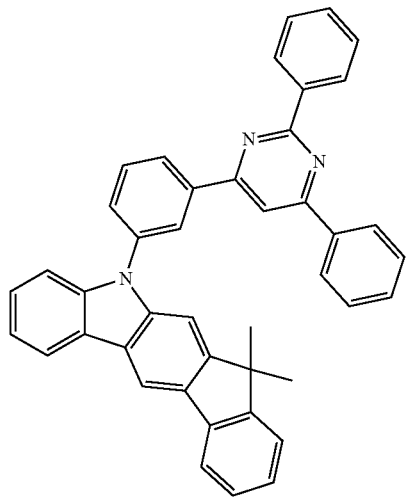 [SMILES: CC1(C)c2ccccc2-c2cc3c4ccccc4n(-c4cccc(-c5cc(-c6ccccc6)nc(-c6ccccc6)n5)c4)c3cc21]
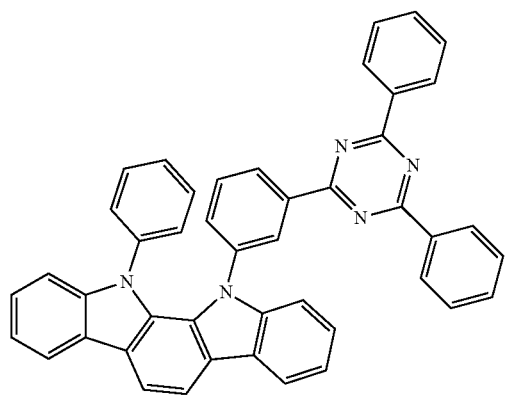 [SMILES: c1ccc(-c2nc(-c3ccccc3)nc(-c3cccc(-n4c5ccccc5c5ccc6c7ccccc7n(-c7ccccc7)c6c54)c3)n2)cc1]
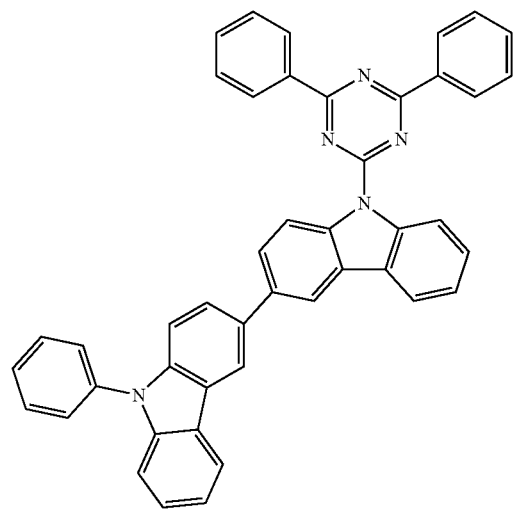 [SMILES: c1ccc(-c2nc(-c3ccccc3)nc(-n3c4ccccc4c4cc(-c5ccc6c(c5)c5ccccc5n6-c5ccccc5)ccc43)n2)cc1]

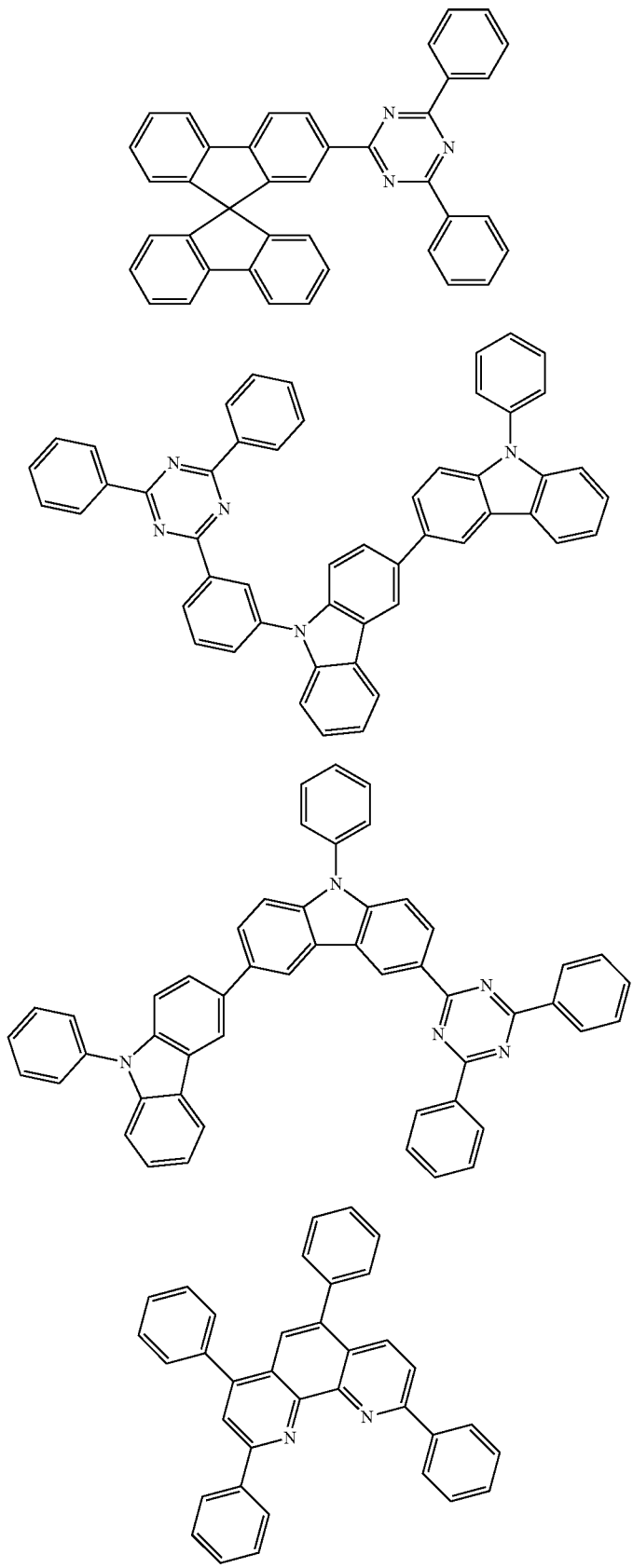

-continued
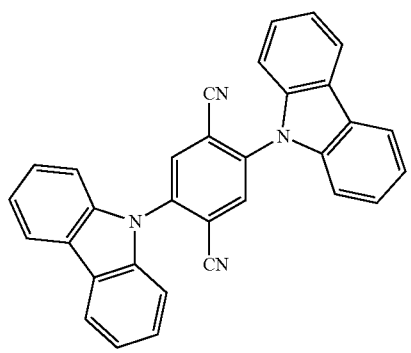 [SMILES: N#Cc1cc(-n2c3ccccc3c3ccccc32)c(C#N)cc1-n1c2ccccc2c2ccccc21]
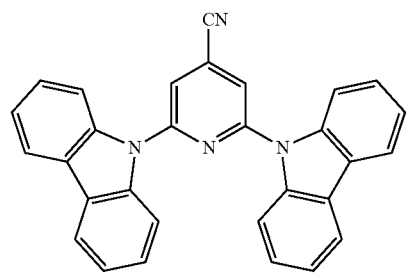 [SMILES: N#Cc1cc(-n2c3ccccc3c3ccccc32)nc(-n2c3ccccc3c3ccccc32)c1]
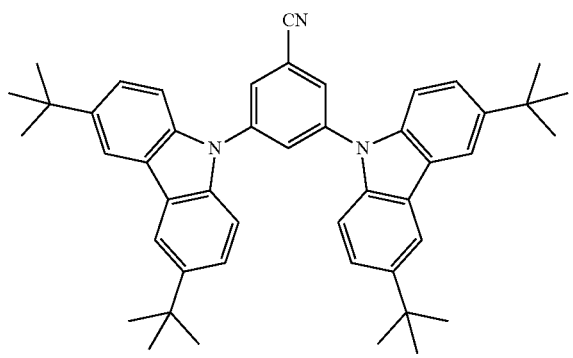 [SMILES: CC(C)(C)c1ccc2c(c1)c1cc(C(C)(C)C)ccc1n2-c1cc(C#N)cc(-n2c3ccc(C(C)(C)C)cc3c3cc(C(C)(C)C)ccc32)c1]
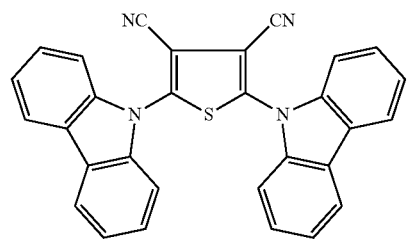 [SMILES: N#Cc1c(-n2c3ccccc3c3ccccc32)sc(-n2c3ccccc3c3ccccc32)c1C#N]
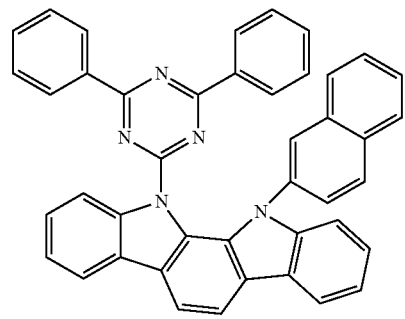 [SMILES: c1ccc(-c2nc(-c3ccccc3)nc(-n3c4ccccc4c4ccc5c6ccccc6n(-c6ccc7ccccc7c6)c5c43)n2)cc1]

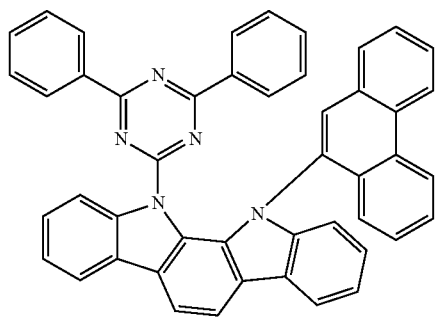 [SMILES: c1ccc(-c2nc(-c3ccccc3)nc(-n3c4ccccc4c4ccc5c6ccccc6n(-c6cc7ccccc7c7ccccc67)c5c43)n2)cc1]
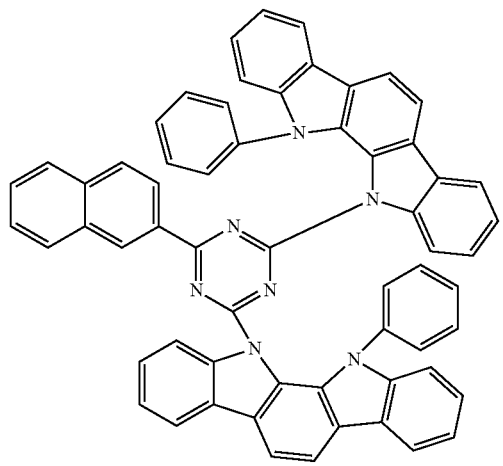 [SMILES: c1ccc(-n2c3ccccc3c3ccc4c5ccccc5n(-c5nc(-c6ccc7ccccc7c6)nc(-n6c7ccccc7c7ccc8c9ccccc9n(-c9ccccc9)c8c76)n5)c4c32)cc1]
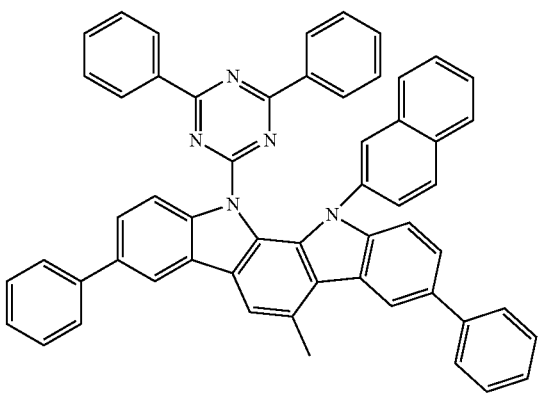 [SMILES: Cc1cc2c3cc(-c4ccccc4)ccc3n(-c3nc(-c4ccccc4)nc(-c4ccccc4)n3)c2c2c1c1cc(-c3ccccc3)ccc1n2-c1ccc2ccccc2c1]
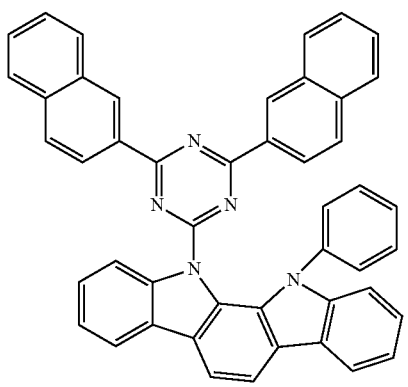 [SMILES: c1ccc(-n2c3ccccc3c3ccc4c5ccccc5n(-c5nc(-c6ccc7ccccc7c6)nc(-c6ccc7ccccc7c6)n5)c4c32)cc1]

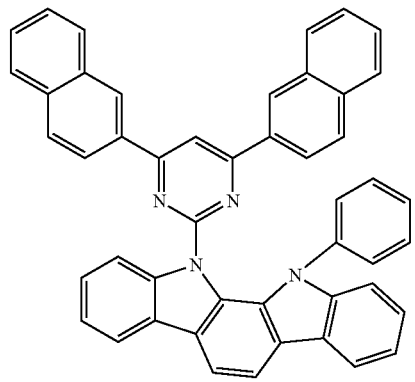 [SMILES: c1ccc(-n2c3ccccc3c3ccc4c5ccccc5n(-c5nc(-c6ccc7ccccc7c6)cc(-c6ccc7ccccc7c6)n5)c4c32)cc1]
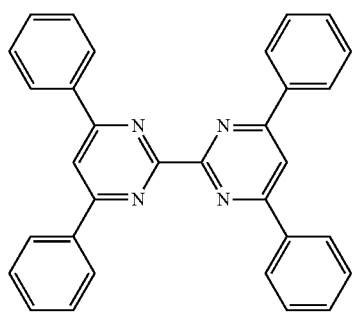 [SMILES: c1ccc(-c2cc(-c3ccccc3)nc(-c3nc(-c4ccccc4)cc(-c4ccccc4)n3)n2)cc1]
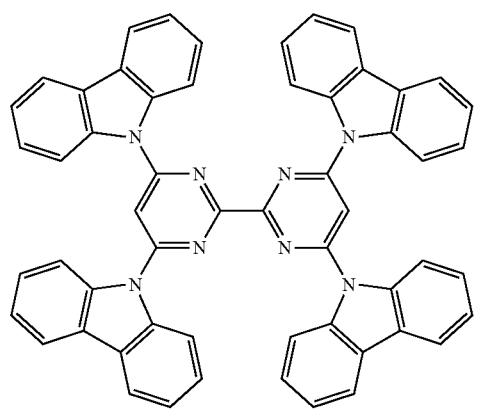 [SMILES: c1ccc2c(c1)c1ccccc1n2-c1cc(-n2c3ccccc3c3ccccc32)nc(-c2nc(-n3c4ccccc4c4ccccc43)cc(-n3c4ccccc4c4ccccc43)n2)n1]
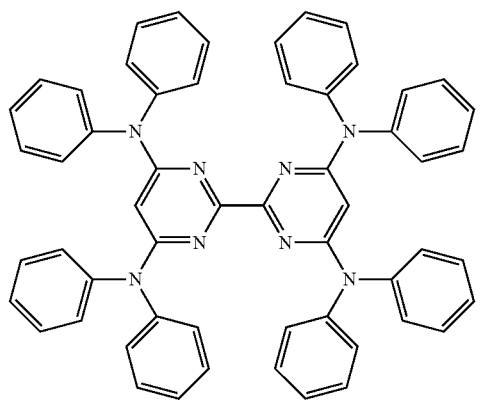 [SMILES: c1ccc(N(c2ccccc2)c2cc(N(c3ccccc3)c3ccccc3)nc(-c3nc(N(c4ccccc4)c4ccccc4)cc(N(c4ccccc4)c4ccccc4)n3)n2)cc1]

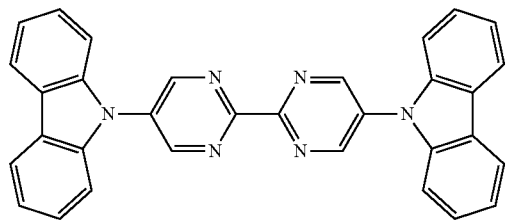 [SMILES: c1ccc2c(c1)c1ccccc1n2-c1cnc(-c2ncc(-n3c4ccccc4c4ccccc43)cn2)nc1]
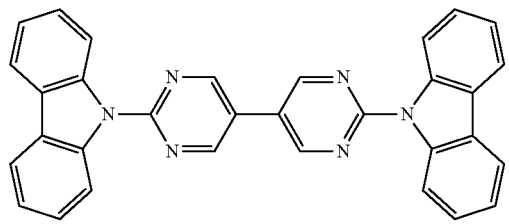 [SMILES: c1ccc2c(c1)c1ccccc1n2-c1ncc(-c2cnc(-n3c4ccccc4c4ccccc43)nc2)cn1]
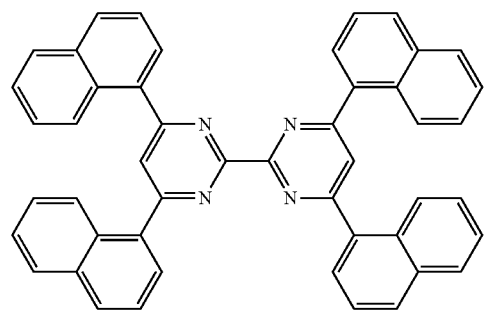 [SMILES: c1ccc2c(-c3cc(-c4cccc5ccccc45)nc(-c4nc(-c5cccc6ccccc56)cc(-c5cccc6ccccc56)n4)n3)cccc2c1]
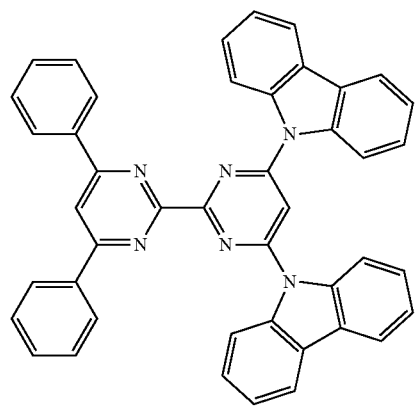 [SMILES: c1ccc(-c2cc(-c3ccccc3)nc(-c3nc(-n4c5ccccc5c5ccccc54)cc(-n4c5ccccc5c5ccccc54)n3)n2)cc1]

-continued
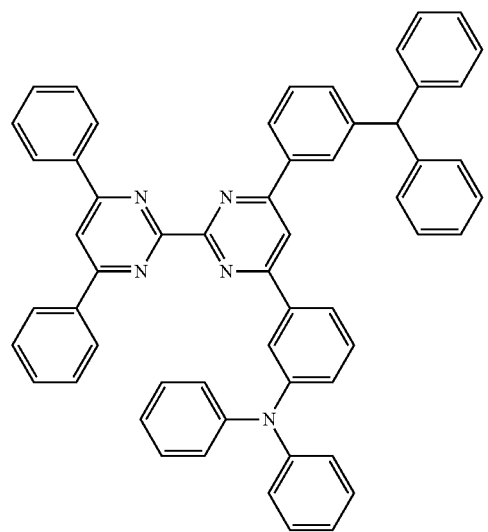 [SMILES: c1ccc(-c2cc(-c3ccccc3)nc(-c3nc(-c4cccc(C(c5ccccc5)c5ccccc5)c4)cc(-c4cccc(N(c5ccccc5)c5ccccc5)c4)n3)n2)cc1]
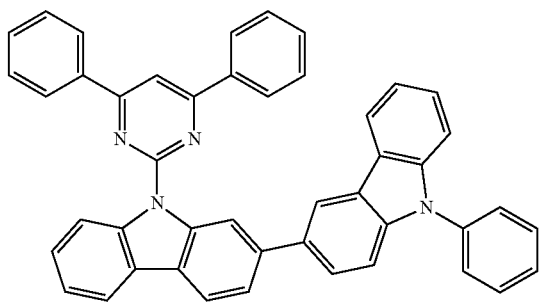 [SMILES: c1ccc(-c2cc(-c3ccccc3)nc(-n3c4ccccc4c4ccc(-c5ccc6c(c5)c5ccccc5n6-c5ccccc5)cc43)n2)cc1]
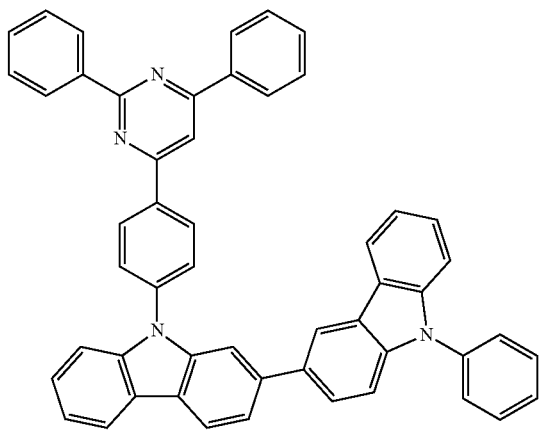 [SMILES: c1ccc(-c2cc(-c3ccc(-n4c5ccccc5c5ccc(-c6ccc7c(c6)c6ccccc6n7-c6ccccc6)cc54)cc3)nc(-c3ccccc3)n2)cc1]
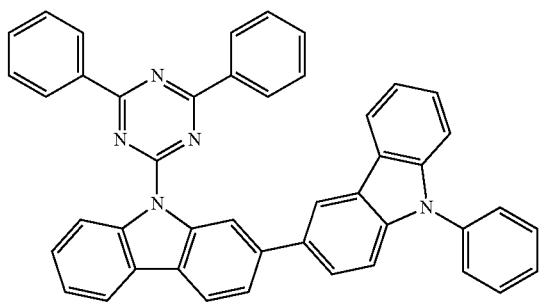 [SMILES: c1ccc(-c2nc(-c3ccccc3)nc(-n3c4ccccc4c4ccc(-c5ccc6c(c5)c5ccccc5n6-c5ccccc5)cc43)n2)cc1]

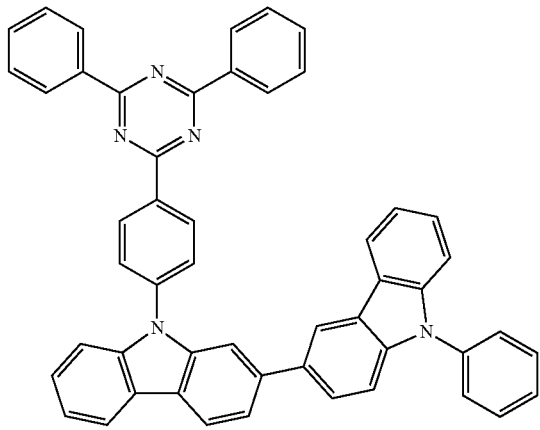 [SMILES: c1ccc(-c2nc(-c3ccccc3)nc(-c3ccc(-n4c5ccccc5c5ccc(-c6ccc7c(c6)c6ccccc6n7-c6ccccc6)cc54)cc3)n2)cc1]
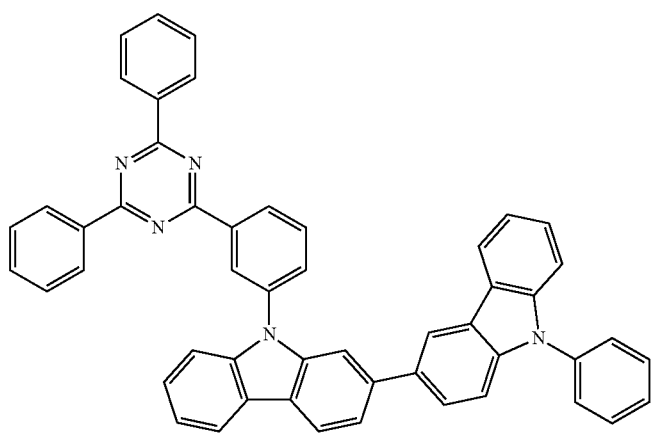 [SMILES: c1ccc(-c2nc(-c3ccccc3)nc(-c3cccc(-n4c5ccccc5c5ccc(-c6ccc7c(c6)c6ccccc6n7-c6ccccc6)cc54)c3)n2)cc1]
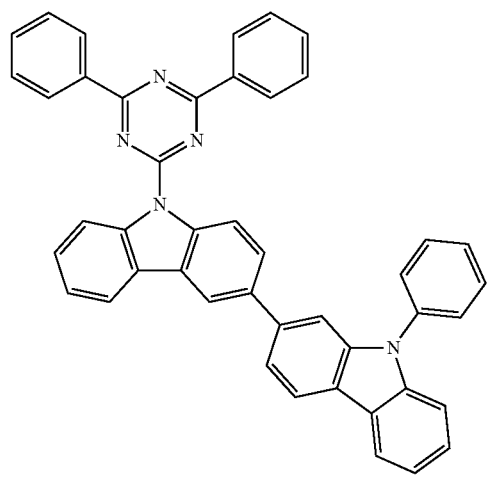 [SMILES: c1ccc(-c2nc(-c3ccccc3)nc(-n3c4ccccc4c4cc(-c5ccc6c7ccccc7n(-c7ccccc7)c6c5)ccc43)n2)cc1]

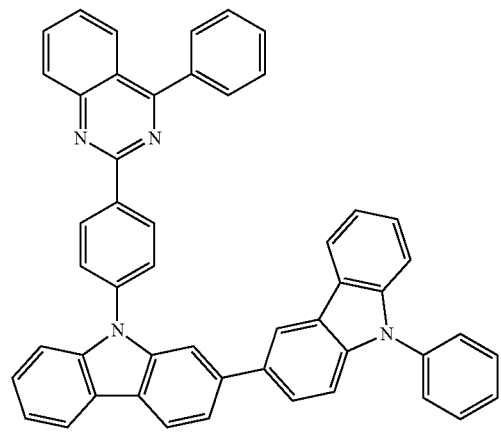 [SMILES: c1ccc(-c2nc(-c3ccc(-n4c5ccccc5c5ccc(-c6ccc7c(c6)c6ccccc6n7-c6ccccc6)cc54)cc3)nc3ccccc23)cc1]
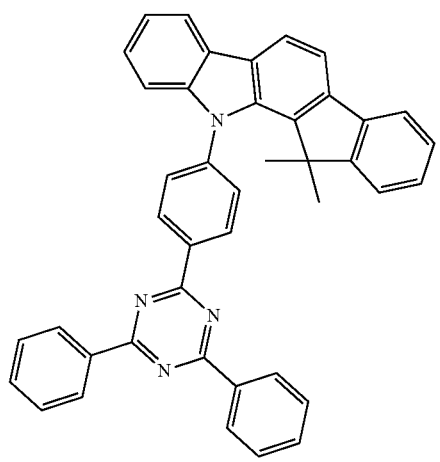 [SMILES: CC1(C)c2ccccc2-c2ccc3c4ccccc4n(-c4ccc(-c5nc(-c6ccccc6)nc(-c6ccccc6)n5)cc4)c3c21]
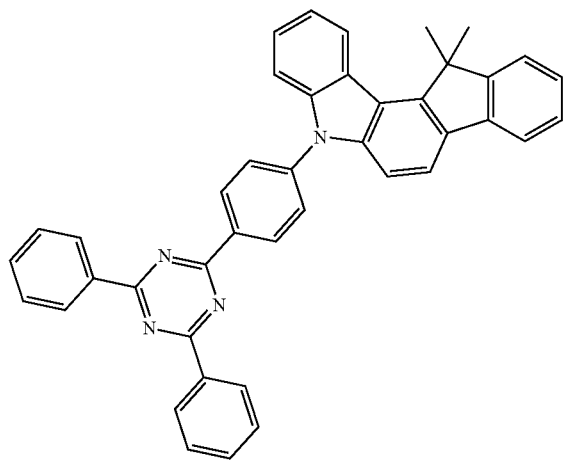 [SMILES: CC1(C)c2ccccc2-c2ccc3c(c21)c1ccccc1n3-c1ccc(-c2nc(-c3ccccc3)nc(-c3ccccc3)n2)cc1]

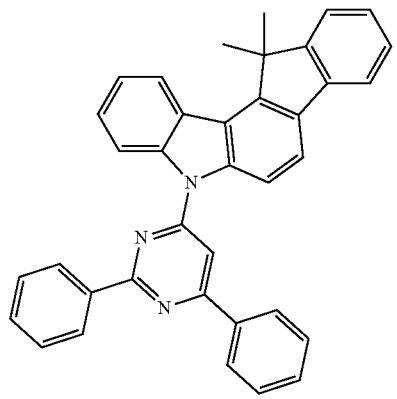 [SMILES: CC1(C)c2ccccc2-c2ccc3c(c21)c1ccccc1n3-c1cc(-c2ccccc2)nc(-c2ccccc2)n1]
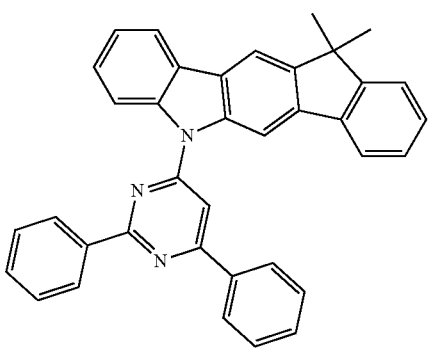 [SMILES: CC1(C)c2ccccc2-c2cc3c(cc21)c1ccccc1n3-c1cc(-c2ccccc2)nc(-c2ccccc2)n1]
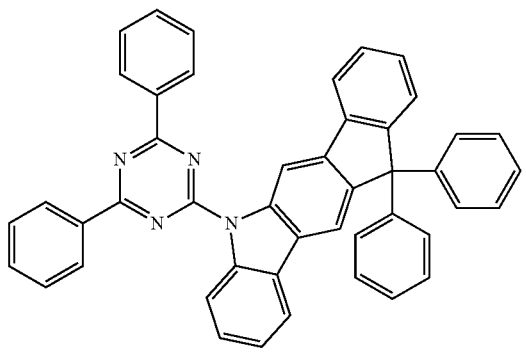 [SMILES: c1ccc(-c2nc(-c3ccccc3)nc(-n3c4ccccc4c4cc5c(cc43)-c3ccccc3C5(c3ccccc3)c3ccccc3)n2)cc1]
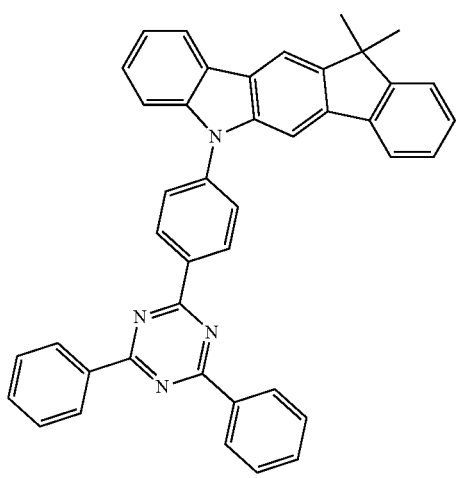 [SMILES: CC1(C)c2ccccc2-c2cc3c(cc21)c1ccccc1n3-c1ccc(-c2nc(-c3ccccc3)nc(-c3ccccc3)n2)cc1]

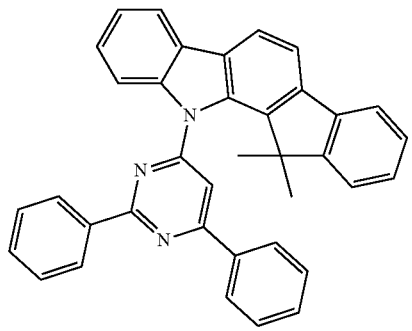 [SMILES: CC1(C)c2ccccc2-c2ccc3c4ccccc4n(-c4cc(-c5ccccc5)nc(-c5ccccc5)n4)c3c21]
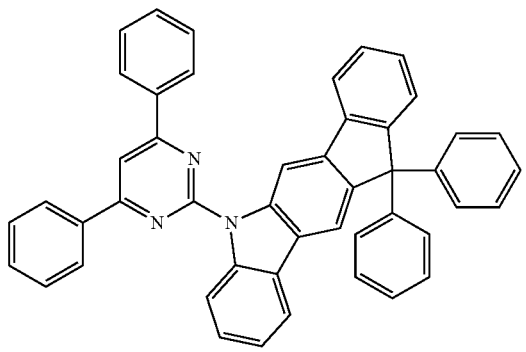 [SMILES: c1ccc(-c2cc(-c3ccccc3)nc(-n3c4ccccc4c4cc5c(cc43)-c3ccccc3C5(c3ccccc3)c3ccccc3)n2)cc1]
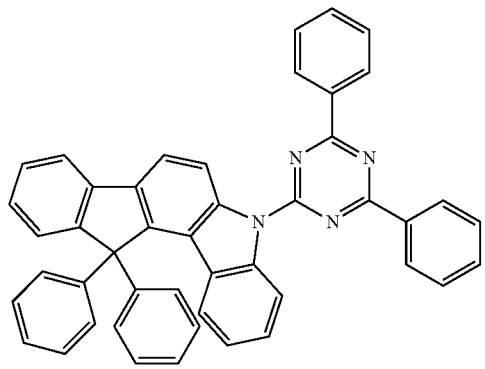 [SMILES: c1ccc(-c2nc(-c3ccccc3)nc(-n3c4ccccc4c4c5c(ccc43)-c3ccccc3C5(c3ccccc3)c3ccccc3)n2)cc1]
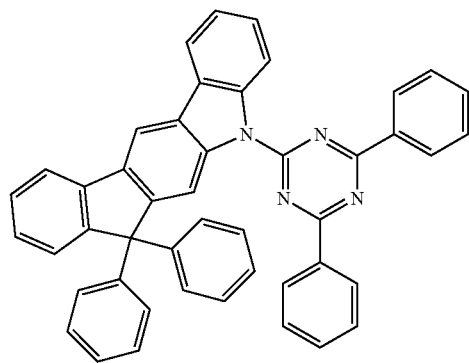 [SMILES: c1ccc(-c2nc(-c3ccccc3)nc(-n3c4ccccc4c4cc5c(cc43)C(c3ccccc3)(c3ccccc3)c3ccccc3-5)n2)cc1]

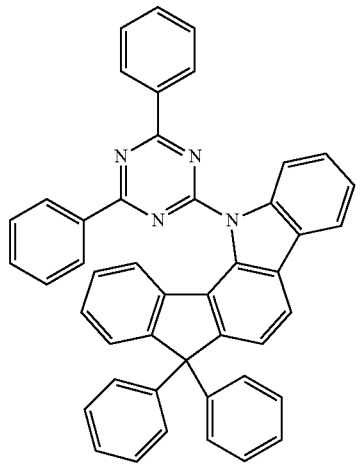 [SMILES: c1ccc(-c2nc(-c3ccccc3)nc(-n3c4ccccc4c4ccc5c(c43)-c3ccccc3C5(c3ccccc3)c3ccccc3)n2)cc1]
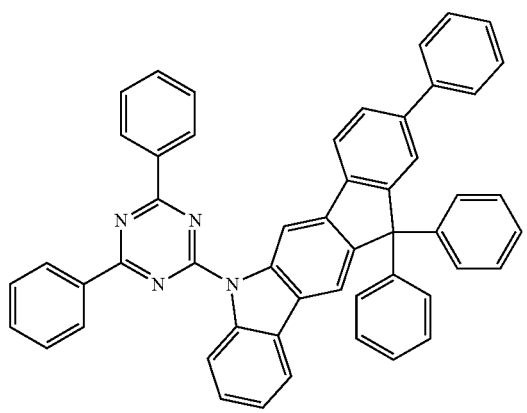 [SMILES: c1ccc(-c2ccc3c(c2)C(c2ccccc2)(c2ccccc2)c2cc4c5ccccc5n(-c5nc(-c6ccccc6)nc(-c6ccccc6)n5)c4cc2-3)cc1]
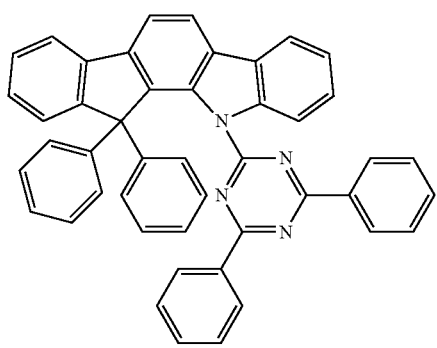 [SMILES: c1ccc(-c2nc(-c3ccccc3)nc(-n3c4ccccc4c4ccc5c(c43)C(c3ccccc3)(c3ccccc3)c3ccccc3-5)n2)cc1]
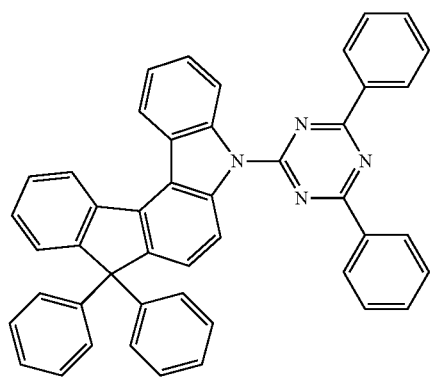 [SMILES: c1ccc(-c2nc(-c3ccccc3)nc(-n3c4ccccc4c4c5c(ccc43)C(c3ccccc3)(c3ccccc3)c3ccccc3-5)n2)cc1]

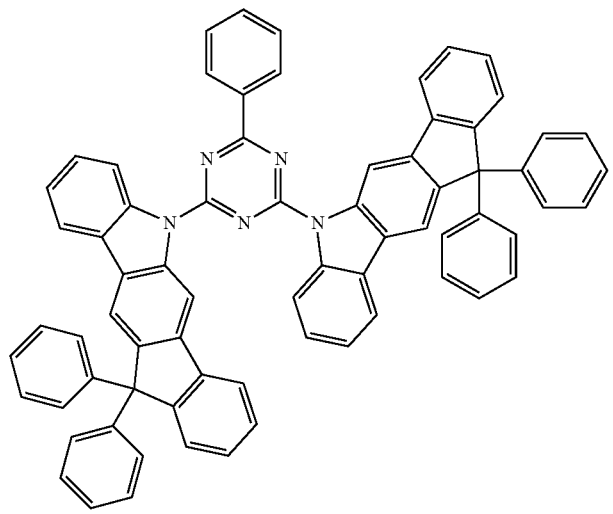 [SMILES: c1ccc(-c2nc(-n3c4ccccc4c4cc5c(cc43)-c3ccccc3C5(c3ccccc3)c3ccccc3)nc(-n3c4ccccc4c4cc5c(cc43)-c3ccccc3C5(c3ccccc3)c3ccccc3)n2)cc1]
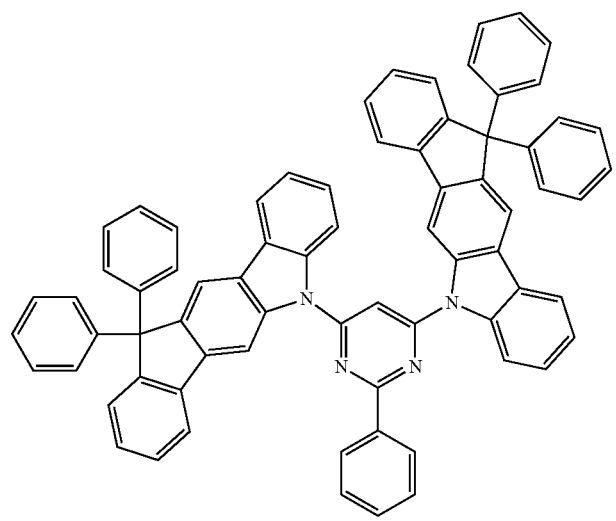 [SMILES: c1ccc(-c2nc(-n3c4ccccc4c4cc5c(cc43)-c3ccccc3C5(c3ccccc3)c3ccccc3)cc(-n3c4ccccc4c4cc5c(cc43)-c3ccccc3C5(c3ccccc3)c3ccccc3)n2)cc1]
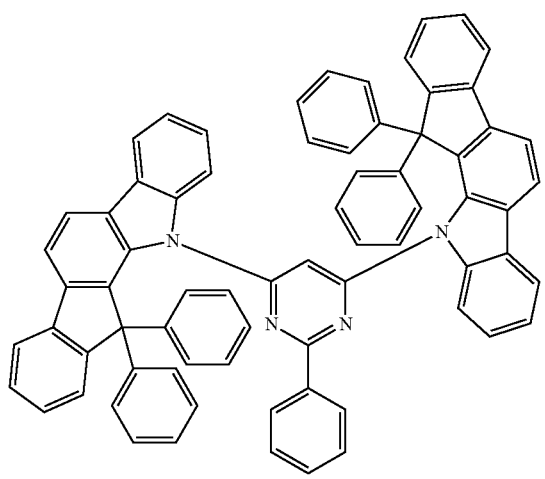 [SMILES: c1ccc(-c2nc(-n3c4ccccc4c4ccc5c(c43)C(c3ccccc3)(c3ccccc3)c3ccccc3-5)cc(-n3c4ccccc4c4ccc5c(c43)C(c3ccccc3)(c3ccccc3)c3ccccc3-5)n2)cc1]

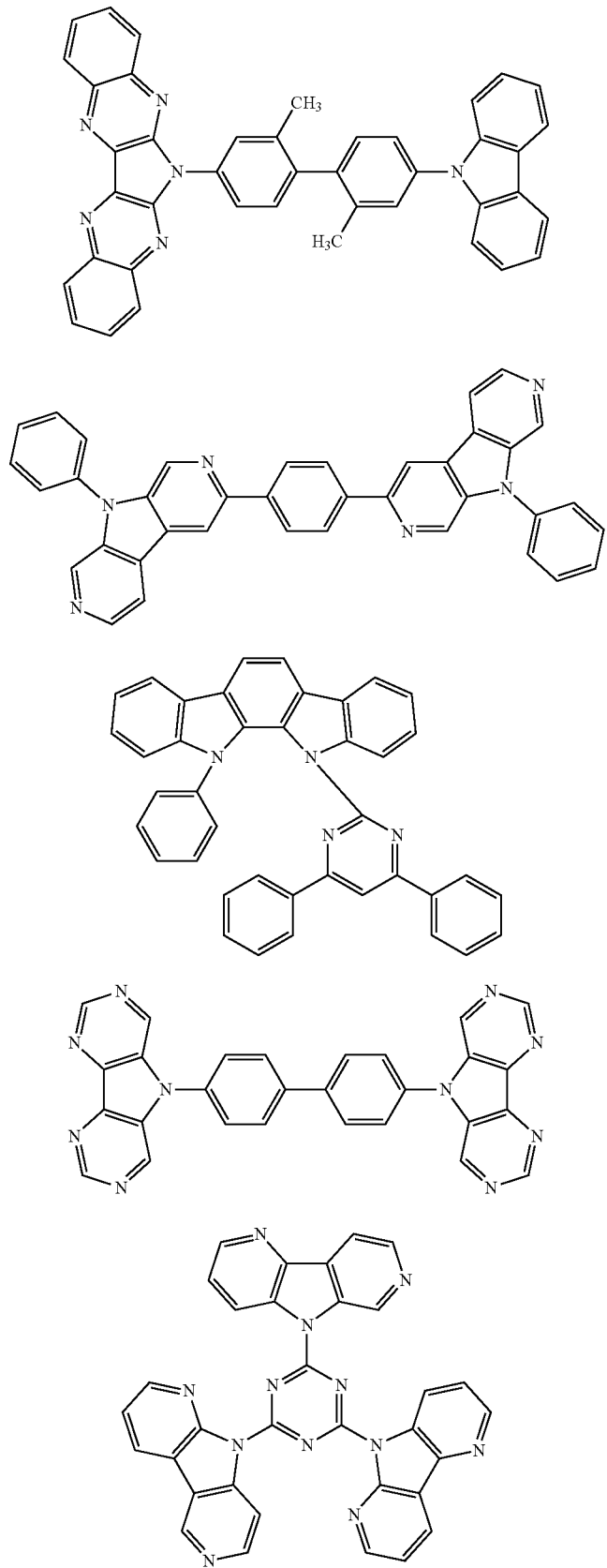

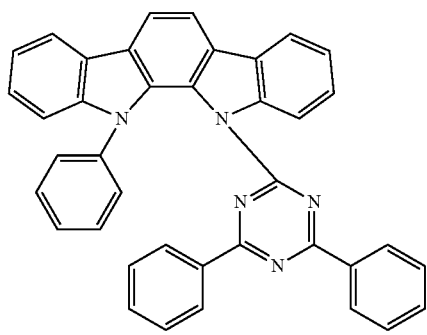 [SMILES: c1ccc(-c2nc(-c3ccccc3)nc(-n3c4ccccc4c4ccc5c6ccccc6n(-c6ccccc6)c5c43)n2)cc1]
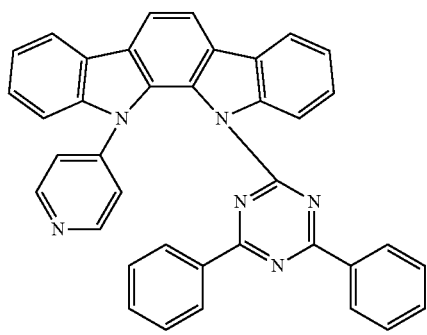 [SMILES: c1ccc(-c2nc(-c3ccccc3)nc(-n3c4ccccc4c4ccc5c6ccccc6n(-c6ccncc6)c5c43)n2)cc1]
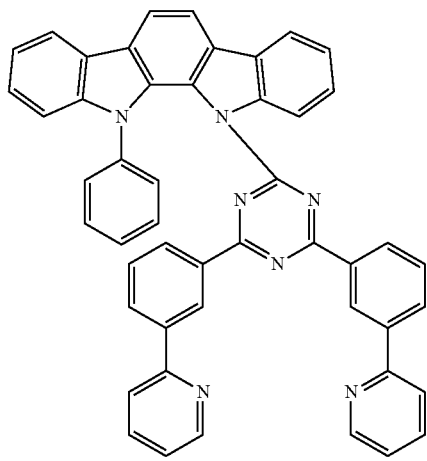 [SMILES: c1ccc(-n2c3ccccc3c3ccc4c5ccccc5n(-c5nc(-c6cccc(-c7ccccn7)c6)nc(-c6cccc(-c7ccccn7)c6)n5)c4c32)cc1]
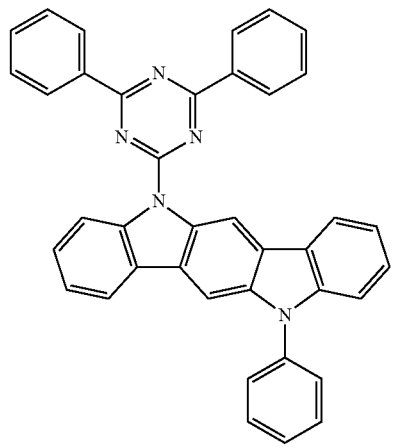 [SMILES: c1ccc(-c2nc(-c3ccccc3)nc(-n3c4ccccc4c4cc5c(cc43)c3ccccc3n5-c3ccccc3)n2)cc1]

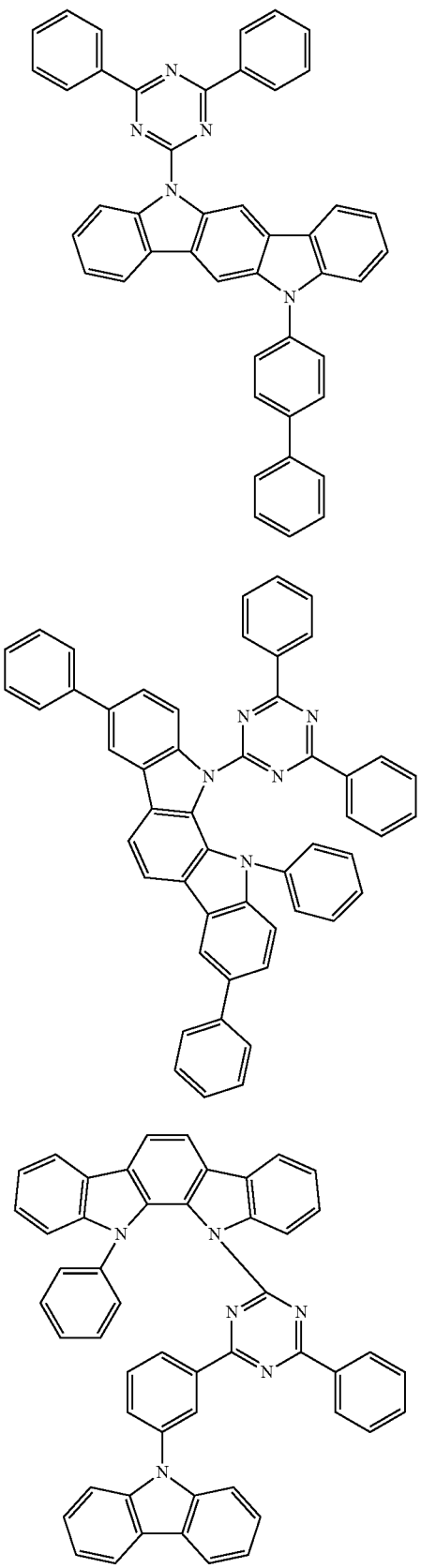

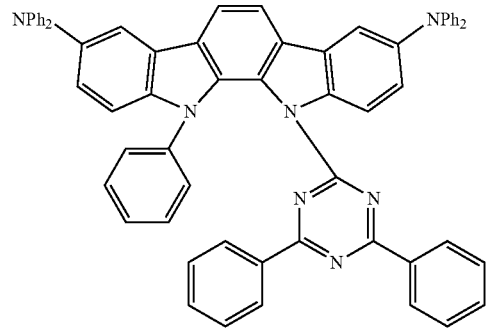
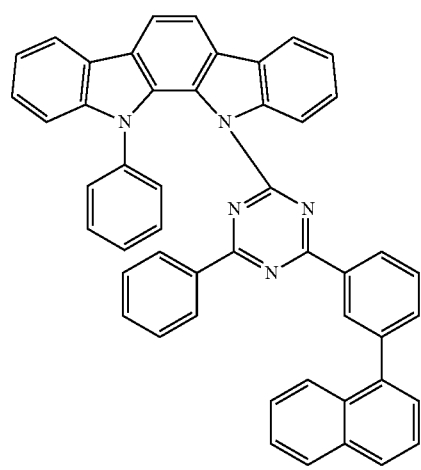 [SMILES: c1ccc(-c2nc(-c3cccc(-c4cccc5ccccc45)c3)nc(-n3c4ccccc4c4ccc5c6ccccc6n(-c6ccccc6)c5c43)n2)cc1]
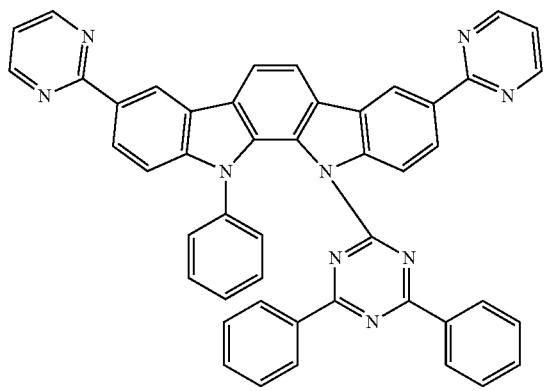 [SMILES: c1ccc(-c2nc(-c3ccccc3)nc(-n3c4ccc(-c5ncccn5)cc4c4ccc5c6cc(-c7ncccn7)ccc6n(-c6ccccc6)c5c43)n2)cc1]
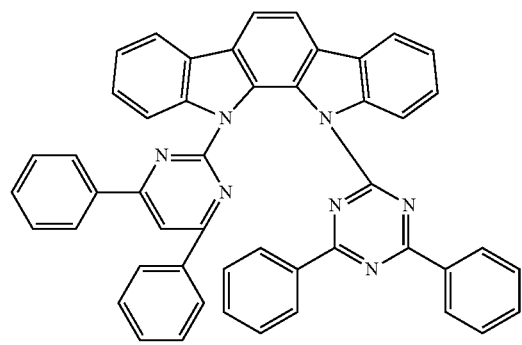 [SMILES: c1ccc(-c2cc(-c3ccccc3)nc(-n3c4ccccc4c4ccc5c6ccccc6n(-c6nc(-c7ccccc7)nc(-c7ccccc7)n6)c5c43)n2)cc1]

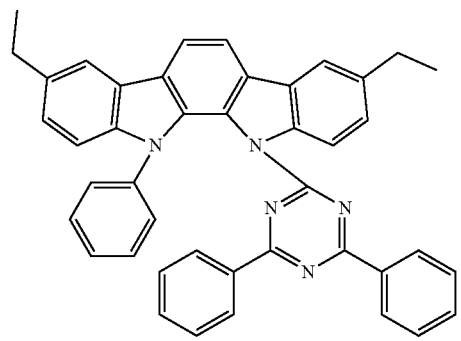 [SMILES: CCc1ccc2c(c1)c1ccc3c4cc(CC)ccc4n(-c4nc(-c5ccccc5)nc(-c5ccccc5)n4)c3c1n2-c1ccccc1]
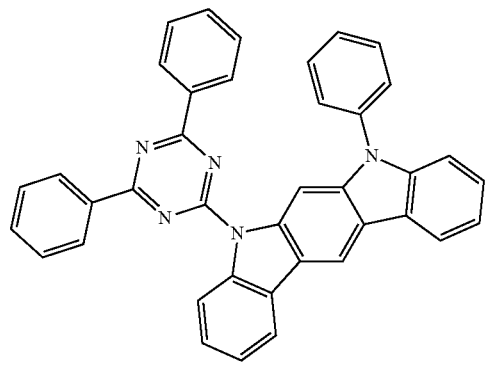 [SMILES: c1ccc(-c2nc(-c3ccccc3)nc(-n3c4ccccc4c4cc5c6ccccc6n(-c6ccccc6)c5cc43)n2)cc1]
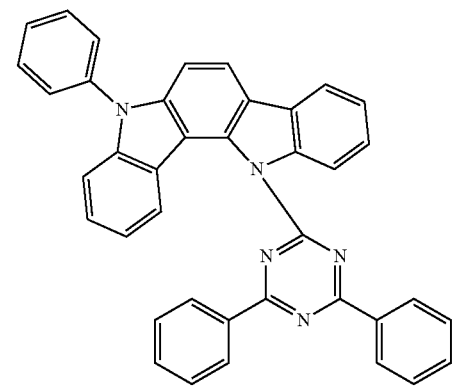 [SMILES: c1ccc(-c2nc(-c3ccccc3)nc(-n3c4ccccc4c4ccc5c(c6ccccc6n5-c5ccccc5)c43)n2)cc1]
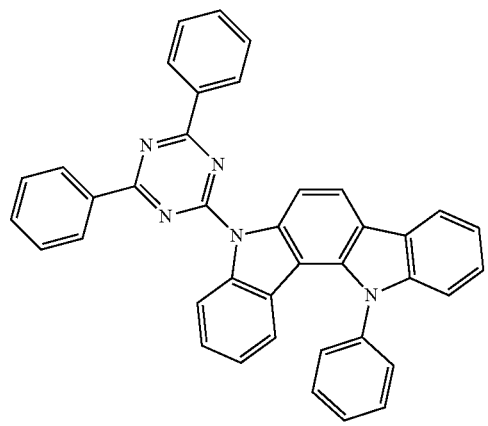 [SMILES: c1ccc(-c2nc(-c3ccccc3)nc(-n3c4ccccc4c4c3ccc3c5ccccc5n(-c5ccccc5)c34)n2)cc1]

-continued
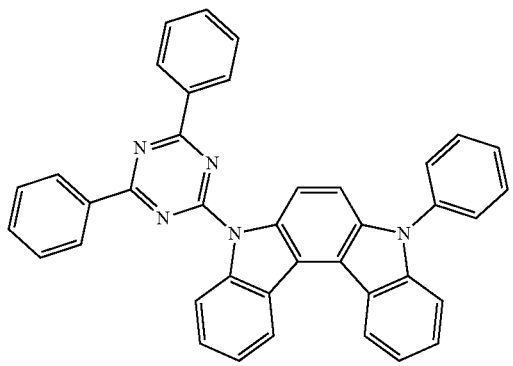 [SMILES: c1ccc(-c2nc(-c3ccccc3)nc(-n3c4ccccc4c4c5c6ccccc6n(-c6ccccc6)c5ccc43)n2)cc1]
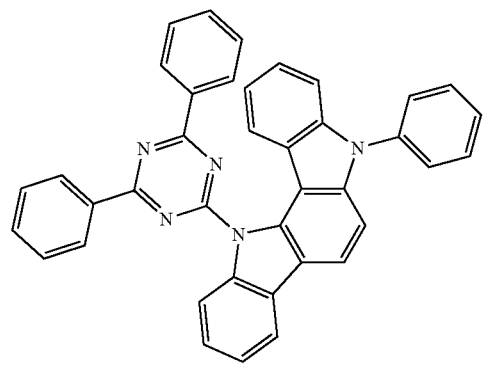 [SMILES: c1ccc(-c2nc(-c3ccccc3)nc(-n3c4ccccc4c4ccc5c(c6ccccc6n5-c5ccccc5)c43)n2)cc1]
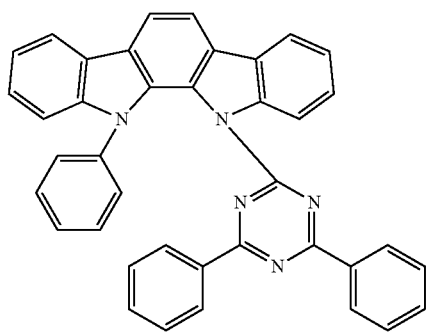 [SMILES: c1ccc(-c2nc(-c3ccccc3)nc(-n3c4ccccc4c4ccc5c6ccccc6n(-c6ccccc6)c5c43)n2)cc1]
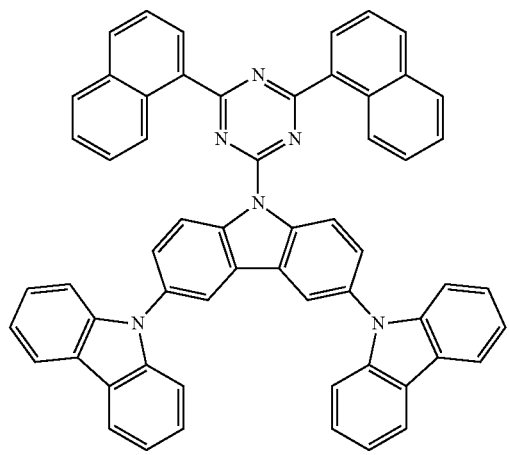 [SMILES: c1ccc2c(-c3nc(-c4cccc5ccccc45)nc(-n4c5ccc(-n6c7ccccc7c7ccccc76)cc5c5cc(-n6c7ccccc7c7ccccc76)ccc54)n3)cccc2c1]

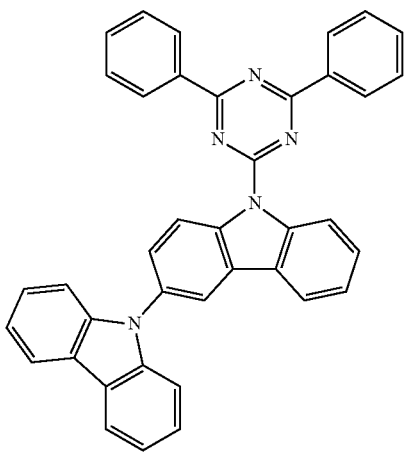 [SMILES: c1ccc(-c2nc(-c3ccccc3)nc(-n3c4ccccc4c4cc(-n5c6ccccc6c6ccccc65)ccc43)n2)cc1]
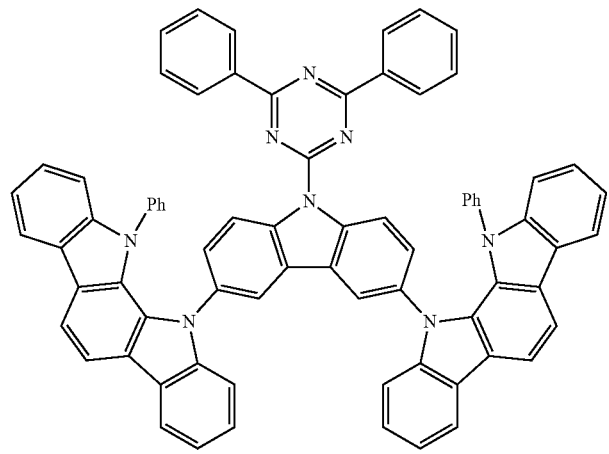 [SMILES: c1ccc(-c2nc(-c3ccccc3)nc(-n3c4ccc(-n5c6ccccc6c6ccc7c8ccccc8n(-c8ccccc8)c7c65)cc4c4cc(-n5c6ccccc6c6ccc7c8ccccc8n(-c8ccccc8)c7c65)ccc43)n2)cc1]
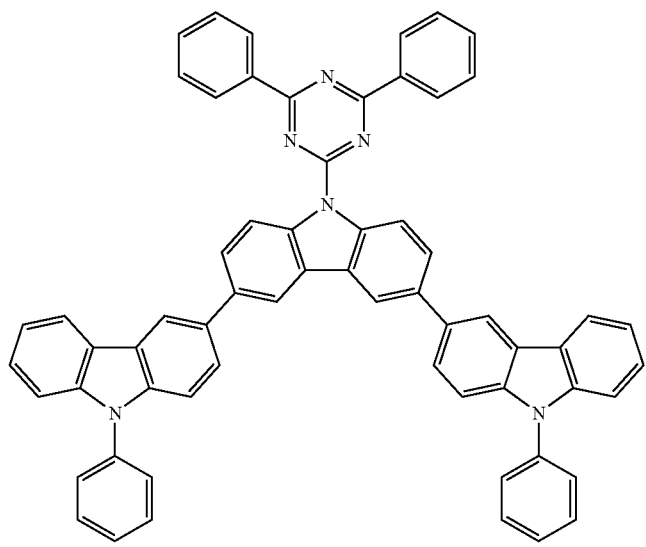 [SMILES: c1ccc(-c2nc(-c3ccccc3)nc(-n3c4ccc(-c5ccc6c(c5)c5ccccc5n6-c5ccccc5)cc4c4cc(-c5ccc6c(c5)c5ccccc5n6-c5ccccc5)ccc43)n2)cc1]

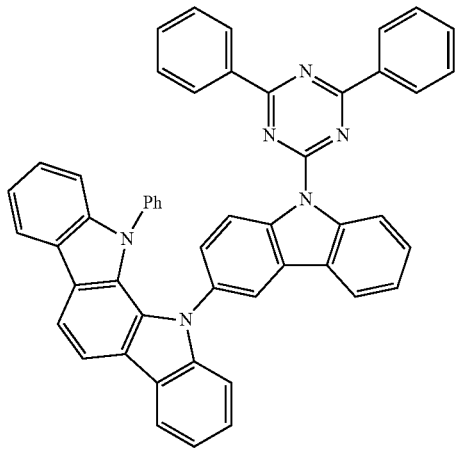 [SMILES: c1ccc(-c2nc(-c3ccccc3)nc(-n3c4ccccc4c4cc(-n5c6ccccc6c6ccc7c8ccccc8n(-c8ccccc8)c7c65)ccc43)n2)cc1]
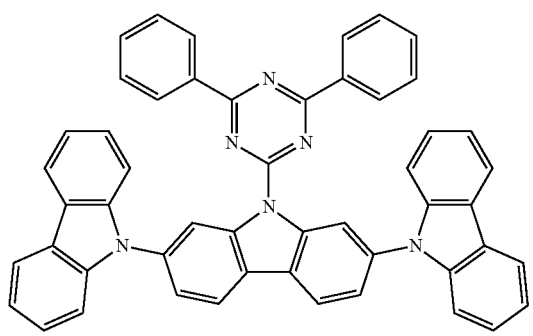 [SMILES: c1ccc(-c2nc(-c3ccccc3)nc(-n3c4cc(-n5c6ccccc6c6ccccc65)ccc4c4ccc(-n5c6ccccc6c6ccccc65)cc43)n2)cc1]
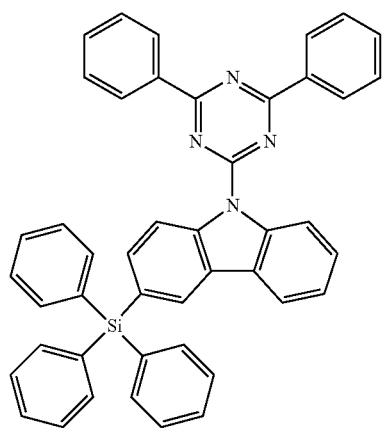 [SMILES: c1ccc(-c2nc(-c3ccccc3)nc(-n3c4ccccc4c4cc([Si](c5ccccc5)(c5ccccc5)c5ccccc5)ccc43)n2)cc1]

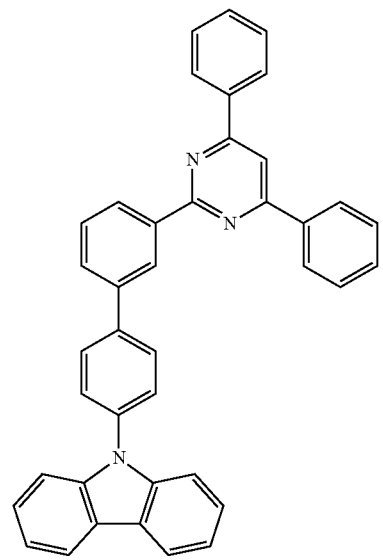 [SMILES: c1ccc(-c2cc(-c3ccccc3)nc(-c3cccc(-c4ccc(-n5c6ccccc6c6ccccc65)cc4)c3)n2)cc1]
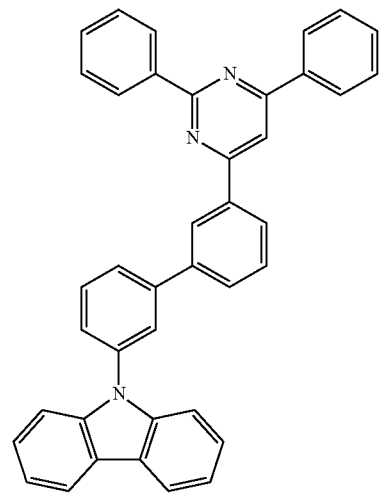 [SMILES: c1ccc(-c2cc(-c3cccc(-c4cccc(-n5c6ccccc6c6ccccc65)c4)c3)nc(-c3ccccc3)n2)cc1]
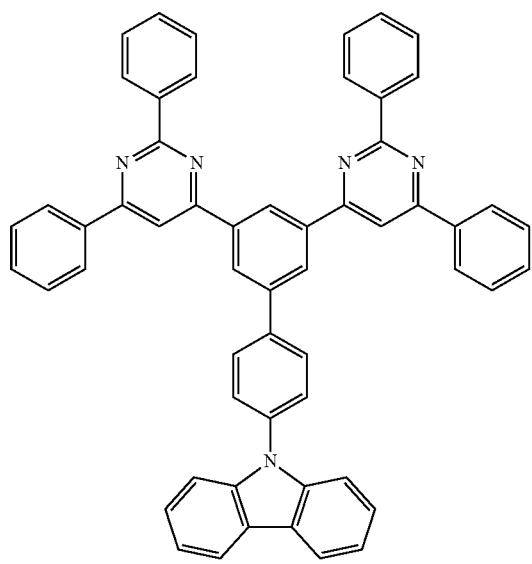 [SMILES: c1ccc(-c2cc(-c3cc(-c4ccc(-n5c6ccccc6c6ccccc65)cc4)cc(-c4cc(-c5ccccc5)nc(-c5ccccc5)n4)c3)nc(-c3ccccc3)n2)cc1]

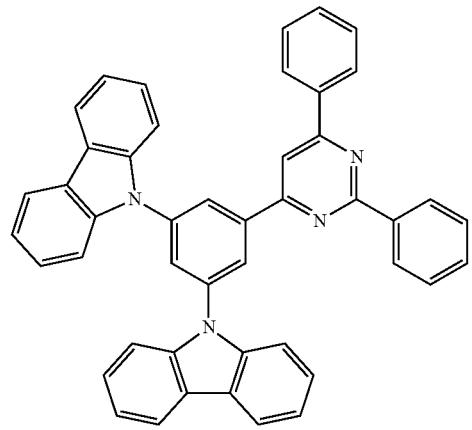 [SMILES: c1ccc(-c2cc(-c3cc(-n4c5ccccc5c5ccccc54)cc(-n4c5ccccc5c5ccccc54)c3)nc(-c3ccccc3)n2)cc1]
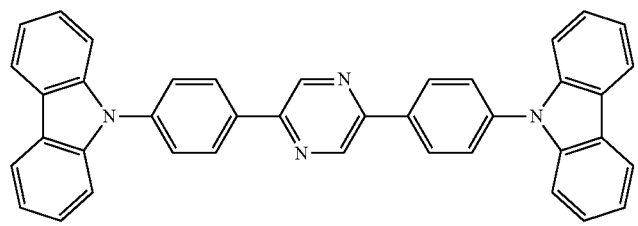 [SMILES: c1ccc2c(c1)c1ccccc1n2-c1ccc(-c2cnc(-c3ccc(-n4c5ccccc5c5ccccc54)cc3)cn2)cc1]
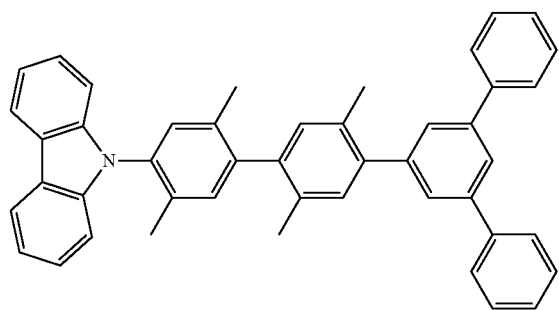 [SMILES: Cc1cc(-c2cc(C)c(-n3c4ccccc4c4ccccc43)cc2C)c(C)cc1-c1cc(-c2ccccc2)cc(-c2ccccc2)c1]
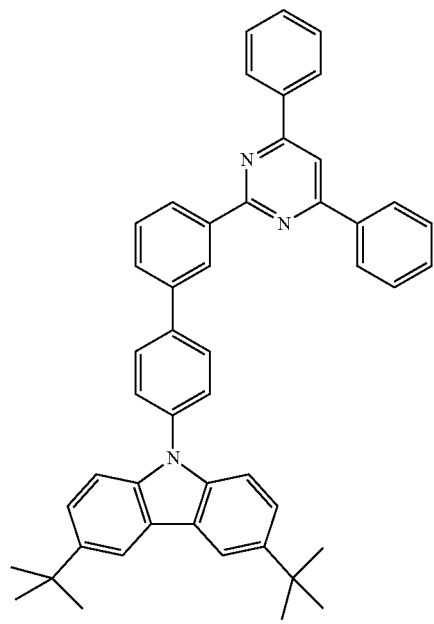 [SMILES: CC(C)(C)c1ccc2c(c1)c1cc(C(C)(C)C)ccc1n2-c1ccc(-c2cccc(-c3nc(-c4ccccc4)cc(-c4ccccc4)n3)c2)cc1]

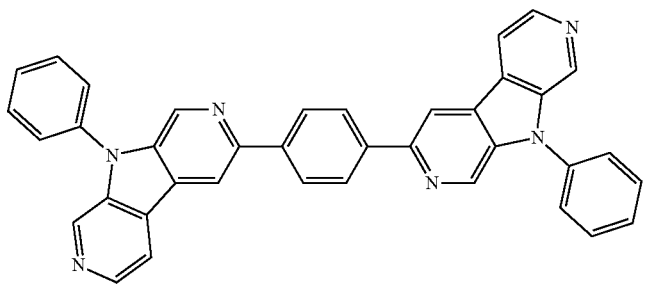 [SMILES: c1ccc(-n2c3cnccc3c3cc(-c4ccc(-c5cc6c7ccncc7n(-c7ccccc7)c6cn5)cc4)ncc32)cc1]
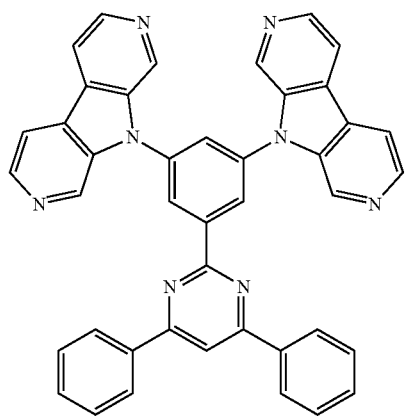 [SMILES: c1ccc(-c2cc(-c3ccccc3)nc(-c3cc(-n4c5cnccc5c5ccncc54)cc(-n4c5cnccc5c5ccncc54)c3)n2)cc1]
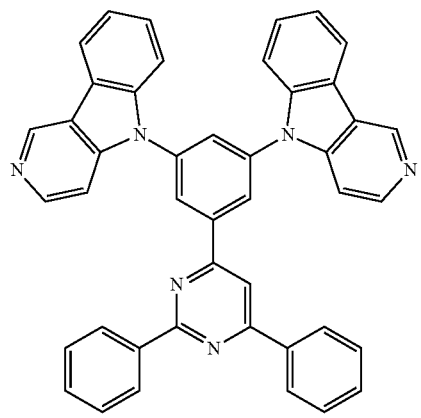 [SMILES: c1ccc(-c2cc(-c3cc(-n4c5ccccc5c5cnccc54)cc(-n4c5ccccc5c5cnccc54)c3)nc(-c3ccccc3)n2)cc1]
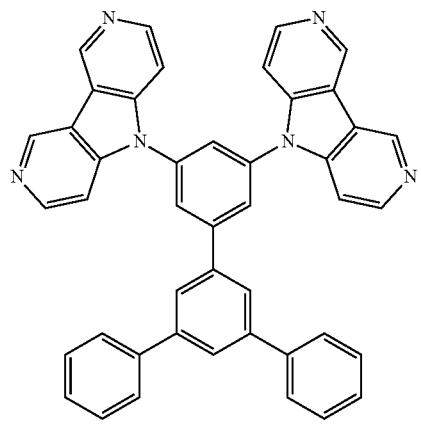 [SMILES: c1ccc(-c2cc(-c3ccccc3)cc(-c3cc(-n4c5ccncc5c5cnccc54)cc(-n4c5ccncc5c5cnccc54)c3)c2)cc1]

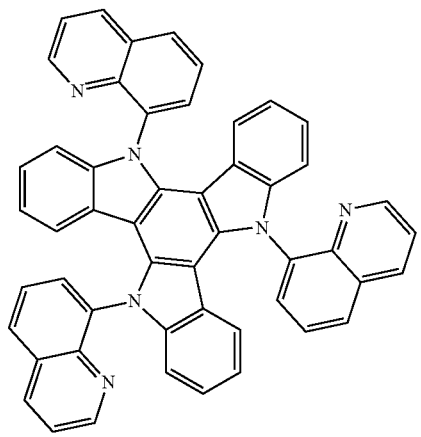 [SMILES: c1cnc2c(-n3c4ccccc4c4c3c3c5ccccc5n(-c5cccc6cccnc56)c3c3c5ccccc5n(-c5cccc6cccnc56)c43)cccc2c1]
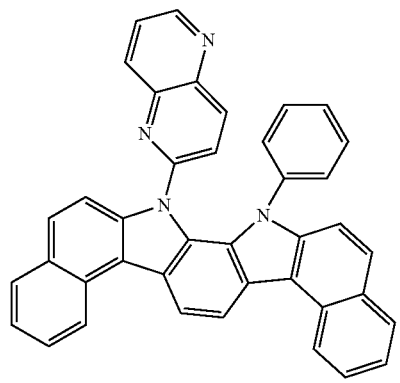 [SMILES: c1ccc(-n2c3ccc4ccccc4c3c3ccc4c5c6ccccc6ccc5n(-c5ccc6ncccc6n5)c4c32)cc1]
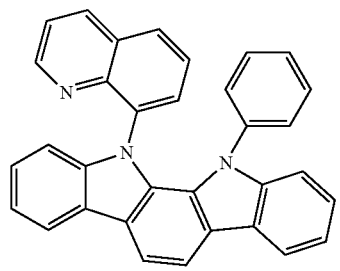 [SMILES: c1ccc(-n2c3ccccc3c3ccc4c5ccccc5n(-c5cccc6cccnc56)c4c32)cc1]
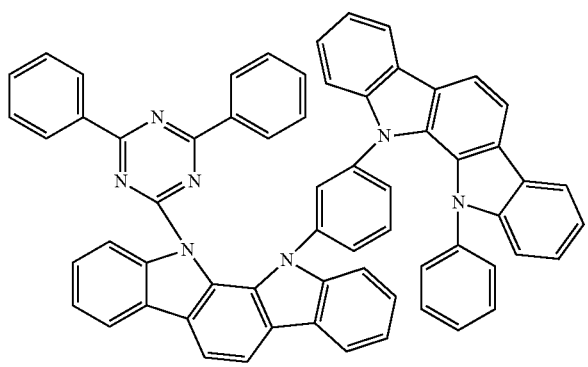 [SMILES: c1ccc(-c2nc(-c3ccccc3)nc(-n3c4ccccc4c4ccc5c6ccccc6n(-c6cccc(-n7c8ccccc8c8ccc9c%10ccccc%10n(-c%10ccccc%10)c9c87)c6)c5c43)n2)cc1]

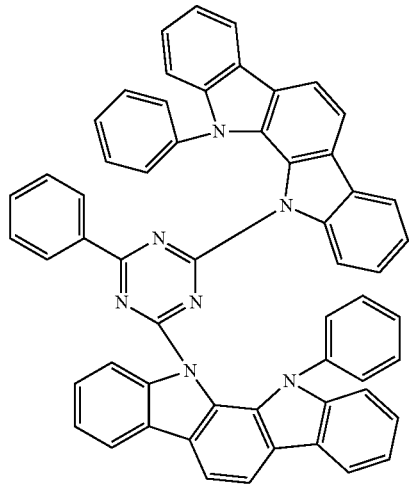 [SMILES: c1ccc(-c2nc(-n3c4ccccc4c4ccc5c6ccccc6n(-c6ccccc6)c5c43)nc(-n3c4ccccc4c4ccc5c6ccccc6n(-c6ccccc6)c5c43)n2)cc1]
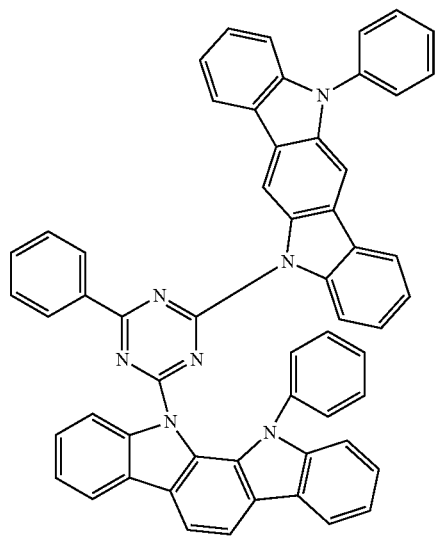 [SMILES: c1ccc(-c2nc(-n3c4ccccc4c4cc5c(cc43)c3ccccc3n5-c3ccccc3)nc(-n3c4ccccc4c4ccc5c6ccccc6n(-c6ccccc6)c5c43)n2)cc1]
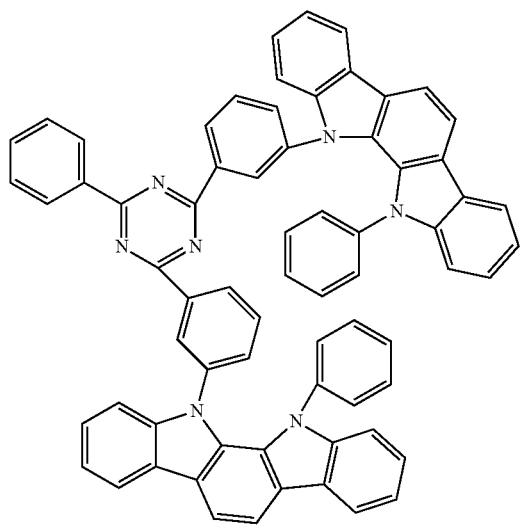 [SMILES: c1ccc(-c2nc(-c3cccc(-n4c5ccccc5c5ccc6c7ccccc7n(-c7ccccc7)c6c54)c3)nc(-c3cccc(-n4c5ccccc5c5ccc6c7ccccc7n(-c7ccccc7)c6c54)c3)n2)cc1]

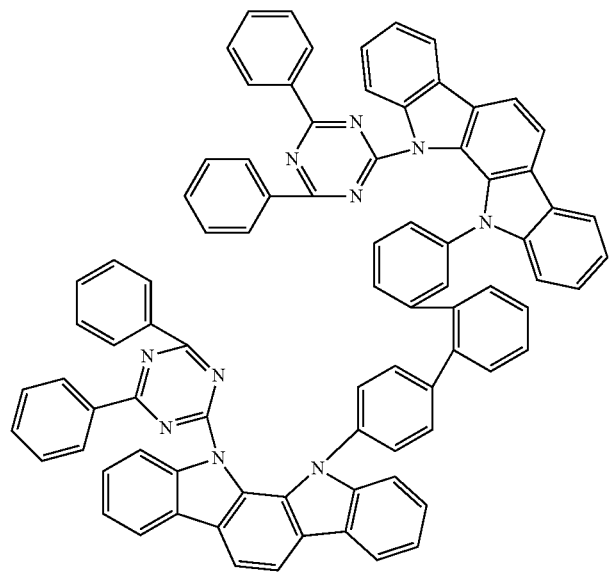 [SMILES: c1ccc(-c2nc(-c3ccccc3)nc(-n3c4ccccc4c4ccc5c6ccccc6n(-c6ccc(-c7ccccc7-c7cccc(-n8c9ccccc9c9ccc%10c%11ccccc%11n(-c%11nc(-c%12ccccc%12)nc(-c%12ccccc%12)n%11)c%10c98)c7)cc6)c5c43)n2)cc1]
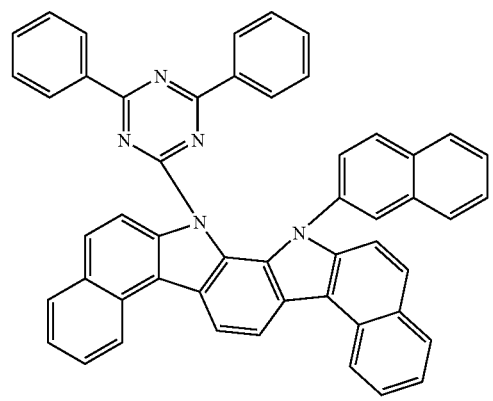 [SMILES: c1ccc(-c2nc(-c3ccccc3)nc(-n3c4ccc5ccccc5c4c4ccc5c6c7ccccc7ccc6n(-c6ccc7ccccc7c6)c5c43)n2)cc1]
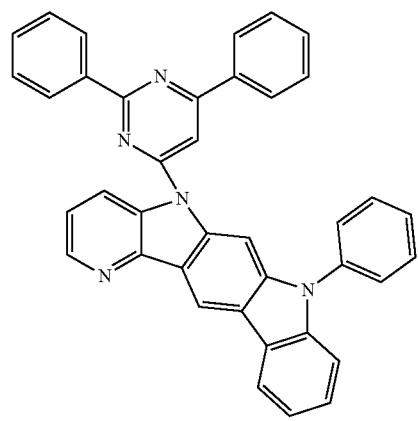 [SMILES: c1ccc(-c2cc(-n3c4cc5c(cc4c4ncccc43)c3ccccc3n5-c3ccccc3)nc(-c3ccccc3)n2)cc1]

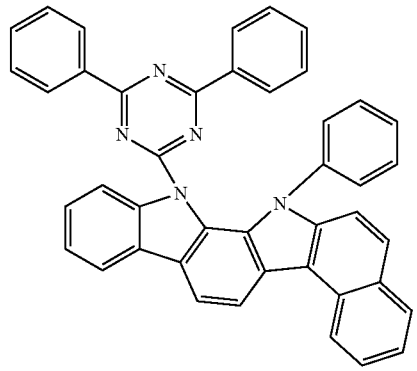 [SMILES: c1ccc(-c2nc(-c3ccccc3)nc(-n3c4ccccc4c4ccc5c6c7ccccc7ccc6n(-c6ccccc6)c5c43)n2)cc1]
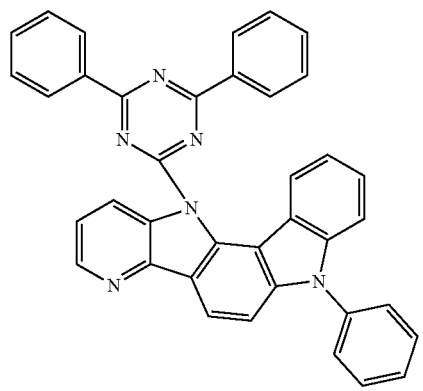 [SMILES: c1ccc(-c2nc(-c3ccccc3)nc(-n3c4cccnc4c4ccc5c(c6ccccc6n5-c5ccccc5)c43)n2)cc1]
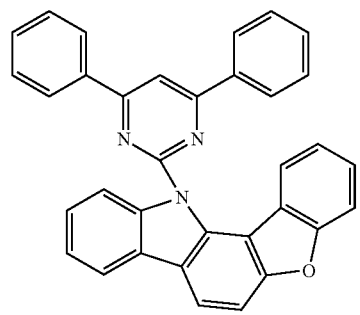 [SMILES: c1ccc(-c2cc(-c3ccccc3)nc(-n3c4ccccc4c4ccc5oc6ccccc6c5c43)n2)cc1]
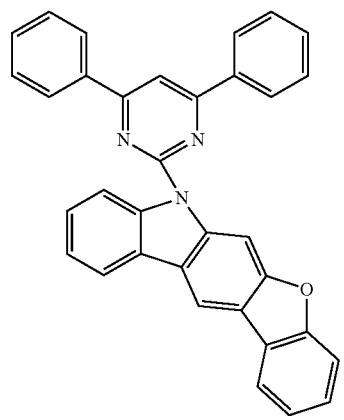 [SMILES: c1ccc(-c2cc(-c3ccccc3)nc(-n3c4ccccc4c4cc5c(cc43)oc3ccccc35)n2)cc1]

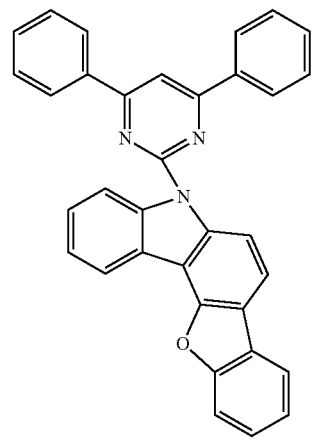 [SMILES: c1ccc(-c2cc(-c3ccccc3)nc(-n3c4ccccc4c4c5oc6ccccc6c5ccc43)n2)cc1]
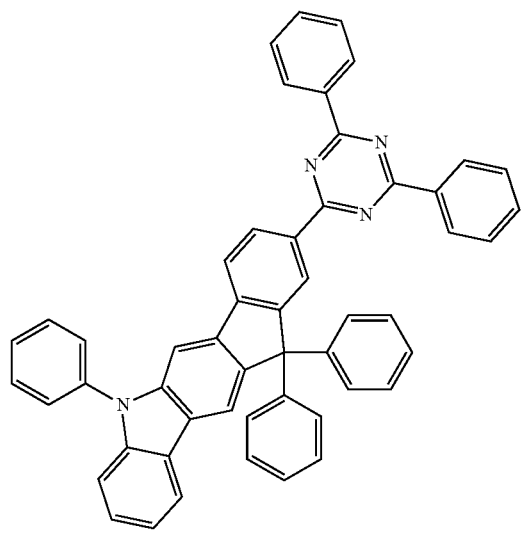 [SMILES: c1ccc(-c2nc(-c3ccccc3)nc(-c3ccc4c(c3)C(c3ccccc3)(c3ccccc3)c3cc5c6ccccc6n(-c6ccccc6)c5cc3-4)n2)cc1]
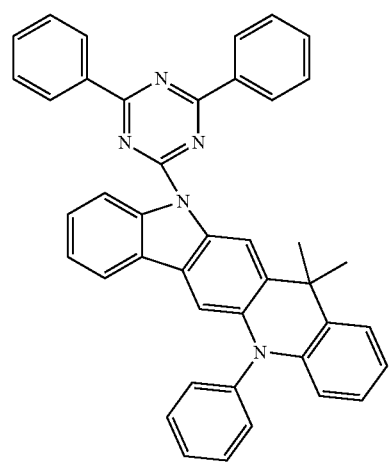 [SMILES: CC1(C)c2ccccc2N(c2ccccc2)c2cc3c4ccccc4n(-c4nc(-c5ccccc5)nc(-c5ccccc5)n4)c3cc21]

-continued
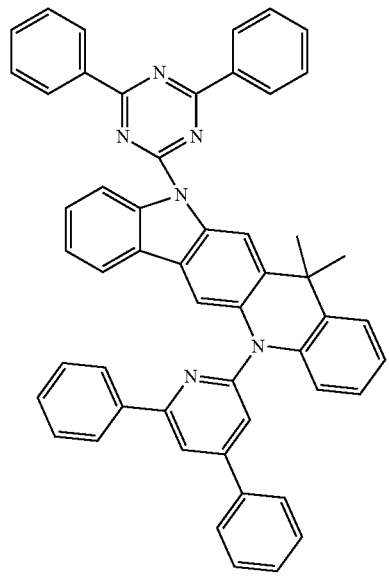 [SMILES: CC1(C)c2ccccc2N(c2cc(-c3ccccc3)cc(-c3ccccc3)n2)c2cc3c4ccccc4n(-c4nc(-c5ccccc5)nc(-c5ccccc5)n4)c3cc21]
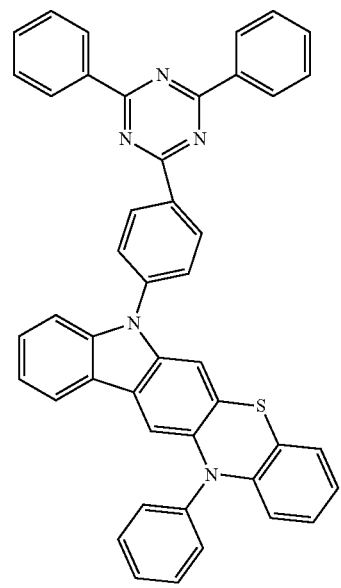 [SMILES: c1ccc(-c2nc(-c3ccccc3)nc(-c3ccc(-n4c5ccccc5c5cc6c(cc54)Sc4ccccc4N6c4ccccc4)cc3)n2)cc1]
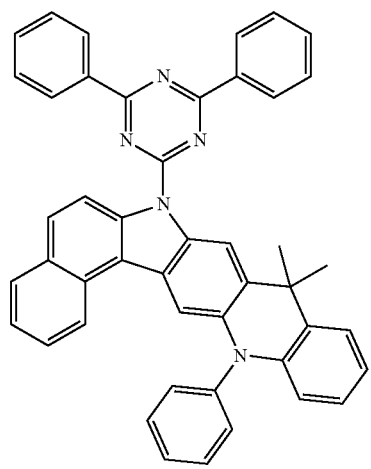 [SMILES: CC1(C)c2ccccc2N(c2ccccc2)c2cc3c4c5ccccc5ccc4n(-c4nc(-c5ccccc5)nc(-c5ccccc5)n4)c3cc21]

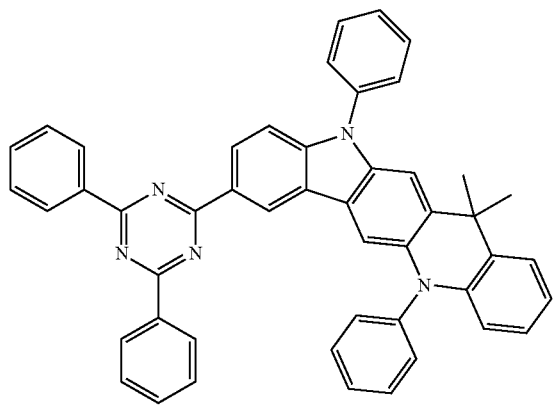 [SMILES: CC1(C)c2ccccc2N(c2ccccc2)c2cc3c4cc(-c5nc(-c6ccccc6)nc(-c6ccccc6)n5)ccc4n(-c4ccccc4)c3cc21]
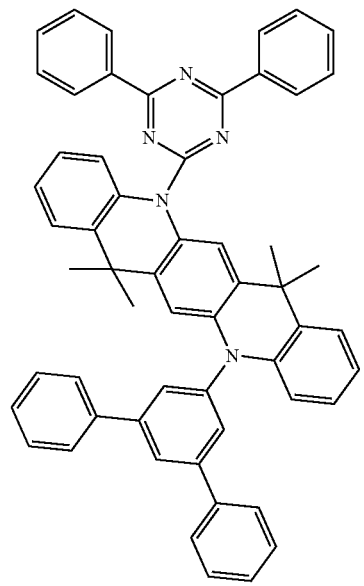 [SMILES: CC1(C)c2ccccc2N(c2cc(-c3ccccc3)cc(-c3ccccc3)c2)c2cc3c(cc21)N(c1nc(-c2ccccc2)nc(-c2ccccc2)n1)c1ccccc1C3(C)C]
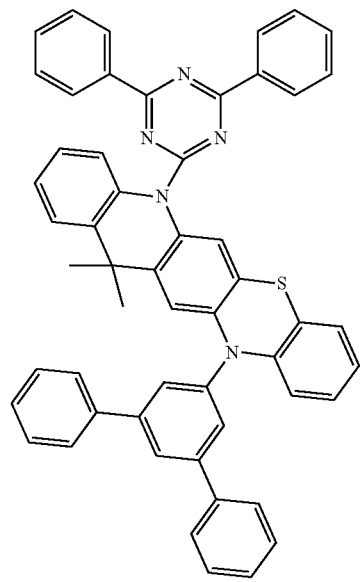 [SMILES: CC1(C)c2ccccc2N(c2nc(-c3ccccc3)nc(-c3ccccc3)n2)c2cc3c(cc21)N(c1cc(-c2ccccc2)cc(-c2ccccc2)c1)c1ccccc1S3]

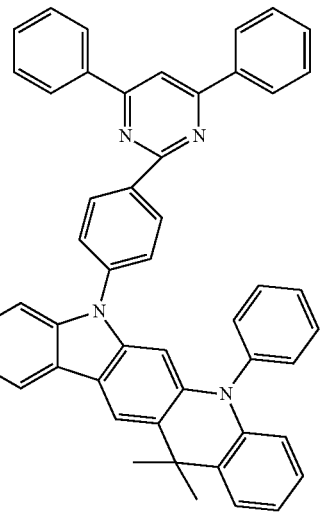
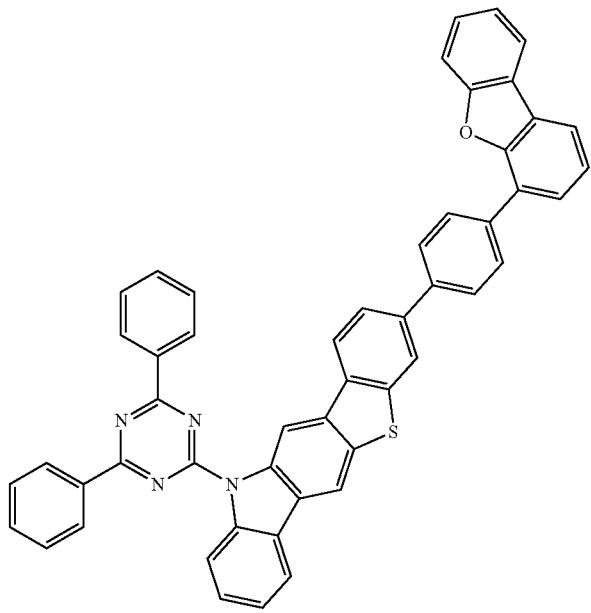 [SMILES: c1ccc(-c2nc(-c3ccccc3)nc(-n3c4ccccc4c4cc5sc6cc(-c7ccc(-c8cccc9c8oc8ccccc89)cc7)ccc6c5cc43)n2)cc1]
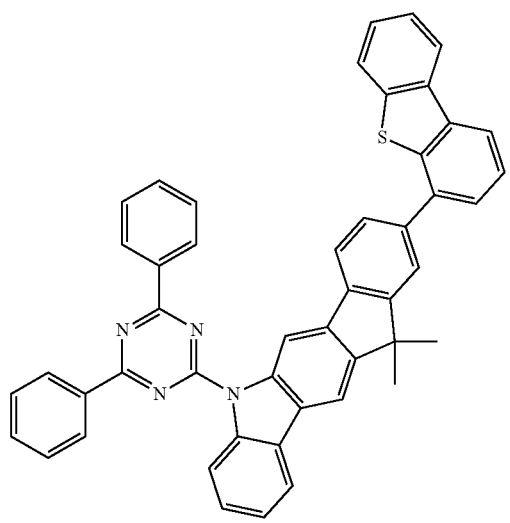 [SMILES: CC1(C)c2cc(-c3cccc4c3sc3ccccc34)ccc2-c2cc3c(cc21)c1ccccc1n3-c1nc(-c2ccccc2)nc(-c2ccccc2)n1]

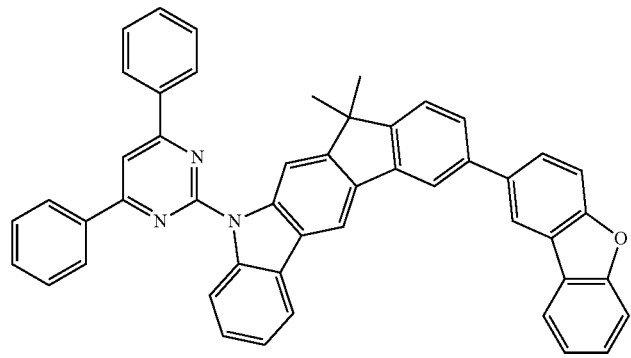 [SMILES: CC1(C)c2ccc(-c3ccc4oc5ccccc5c4c3)cc2-c2cc3c4ccccc4n(-c4nc(-c5ccccc5)cc(-c5ccccc5)n4)c3cc21]
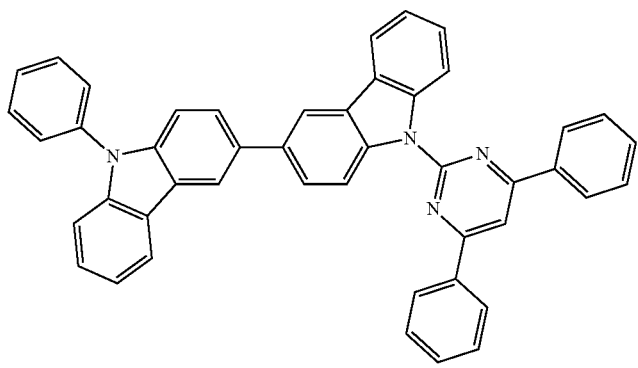 [SMILES: c1ccc(-c2cc(-c3ccccc3)nc(-n3c4ccccc4c4cc(-c5ccc6c(c5)c5ccccc5n6-c5ccccc5)ccc43)n2)cc1]
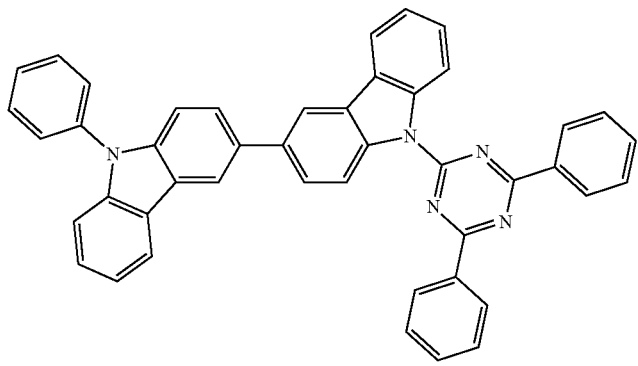 [SMILES: c1ccc(-c2nc(-c3ccccc3)nc(-n3c4ccccc4c4cc(-c5ccc6c(c5)c5ccccc5n6-c5ccccc5)ccc43)n2)cc1]
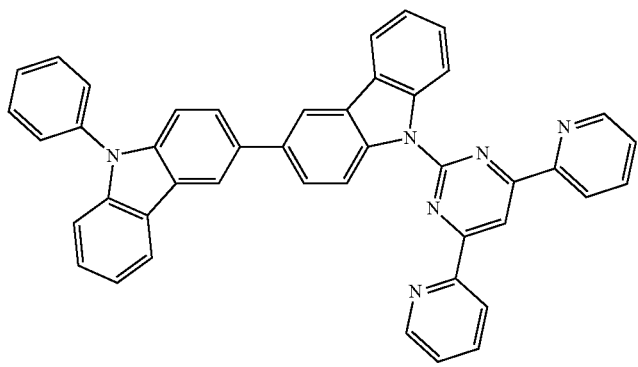 [SMILES: c1ccc(-n2c3ccccc3c3cc(-c4ccc5c(c4)c4ccccc4n5-c4nc(-c5ccccn5)cc(-c5ccccn5)n4)ccc32)cc1]

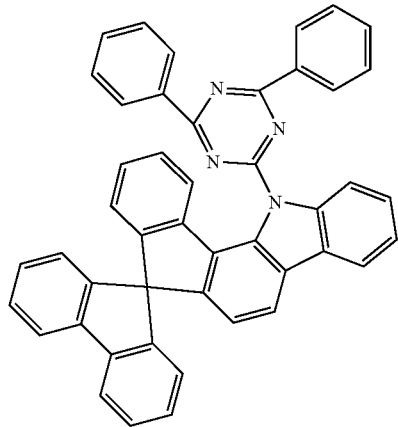 [SMILES: c1ccc(-c2nc(-c3ccccc3)nc(-n3c4ccccc4c4ccc5c(c43)-c3ccccc3C53c4ccccc4-c4ccccc43)n2)cc1]
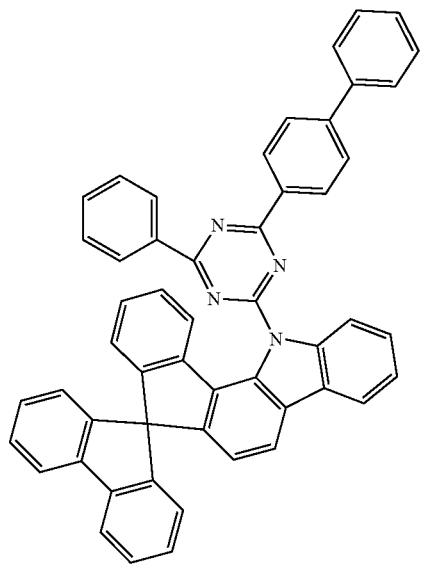 [SMILES: c1ccc(-c2ccc(-c3nc(-c4ccccc4)nc(-n4c5ccccc5c5ccc6c(c54)-c4ccccc4C64c5ccccc5-c5ccccc54)n3)cc2)cc1]
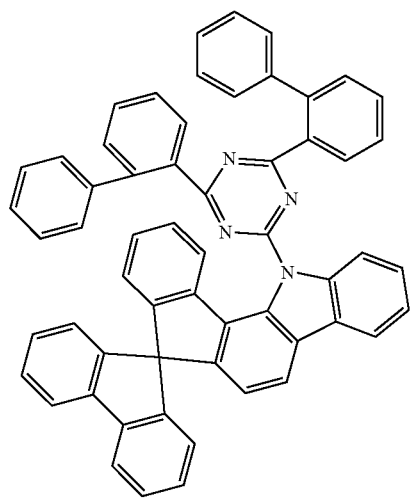 [SMILES: c1ccc(-c2ccccc2-c2nc(-c3ccccc3-c3ccccc3)nc(-n3c4ccccc4c4ccc5c(c43)-c3ccccc3C53c4ccccc4-c4ccccc43)n2)cc1]

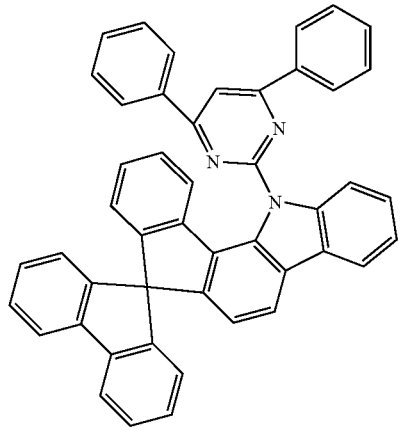 [SMILES: c1ccc(-c2cc(-c3ccccc3)nc(-n3c4ccccc4c4ccc5c(c43)-c3ccccc3C53c4ccccc4-c4ccccc43)n2)cc1]
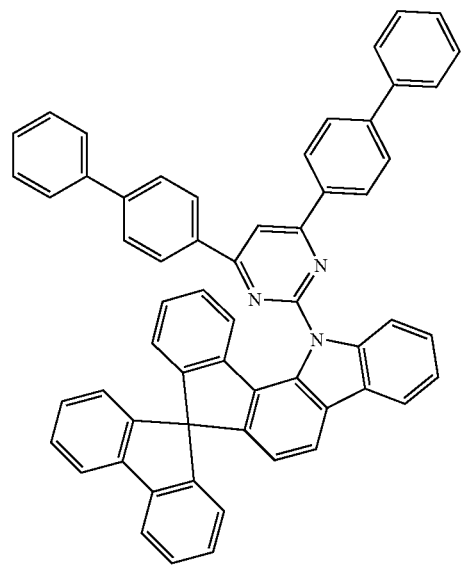 [SMILES: c1ccc(-c2ccc(-c3cc(-c4ccc(-c5ccccc5)cc4)nc(-n4c5ccccc5c5ccc6c(c54)-c4ccccc4C64c5ccccc5-c5ccccc54)n3)cc2)cc1]
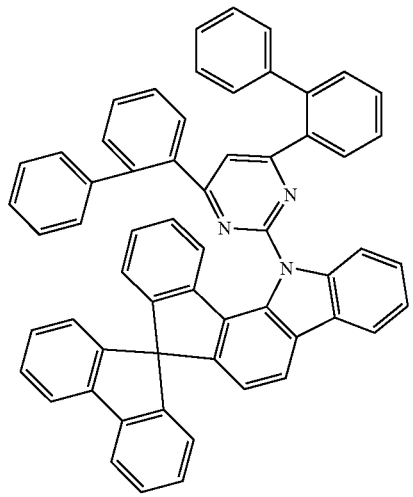 [SMILES: c1ccc(-c2ccccc2-c2cc(-c3ccccc3-c3ccccc3)nc(-n3c4ccccc4c4ccc5c(c43)-c3ccccc3C53c4ccccc4-c4ccccc43)n2)cc1]

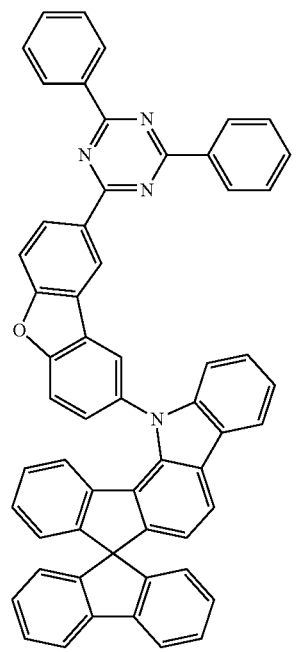 [SMILES: c1ccc(-c2nc(-c3ccccc3)nc(-c3ccc4oc5ccc(-n6c7ccccc7c7ccc8c(c76)-c6ccccc6C86c7ccccc7-c7ccccc76)cc5c4c3)n2)cc1]
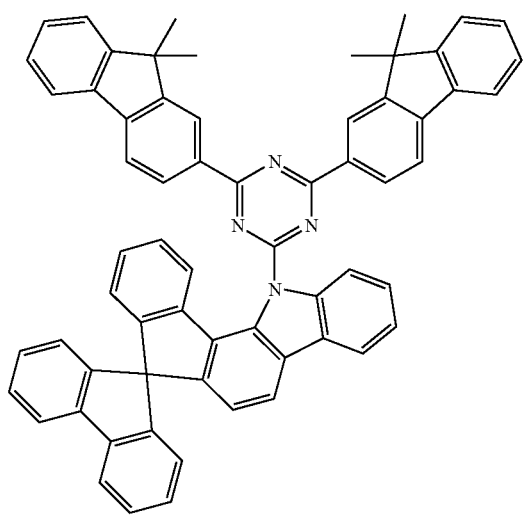 [SMILES: CC1(C)c2ccccc2-c2ccc(-c3nc(-c4ccc5c(c4)C(C)(C)c4ccccc4-5)nc(-n4c5ccccc5c5ccc6c(c54)-c4ccccc4C64c5ccccc5-c5ccccc54)n3)cc21]

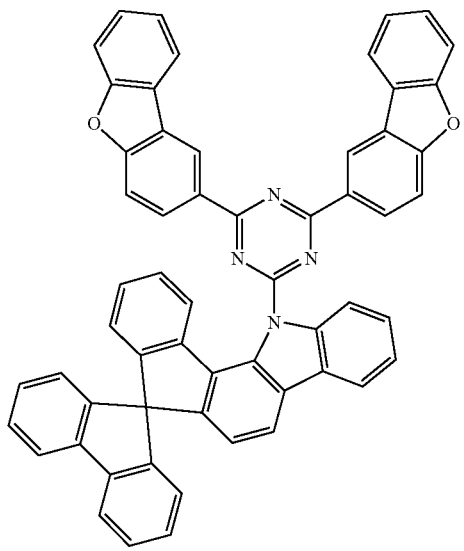 [SMILES: c1ccc2c(c1)-c1ccccc1C21c2ccccc2-c2c1ccc1c3ccccc3n(-c3nc(-c4ccc5oc6ccccc6c5c4)nc(-c4ccc5oc6ccccc6c5c4)n3)c21]
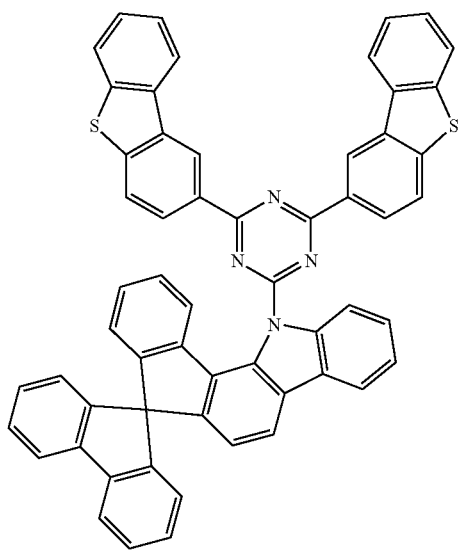 [SMILES: c1ccc2c(c1)-c1ccccc1C21c2ccccc2-c2c1ccc1c3ccccc3n(-c3nc(-c4ccc5sc6ccccc6c5c4)nc(-c4ccc5sc6ccccc6c5c4)n3)c21]

-continued
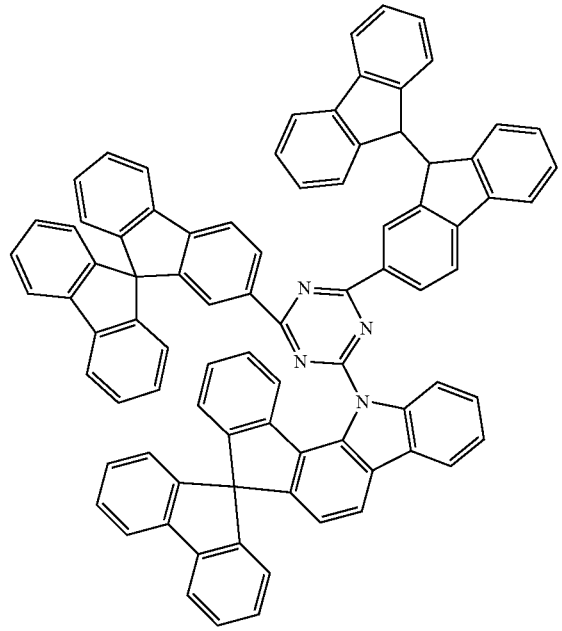 [SMILES: c1ccc2c(c1)-c1ccccc1C2C1c2ccccc2-c2ccc(-c3nc(-c4ccc5c(c4)C4(c6ccccc6-c6ccccc64)c4ccccc4-5)nc(-n4c5ccccc5c5ccc6c(c54)-c4ccccc4C64c5ccccc5-c5ccccc54)n3)cc21]
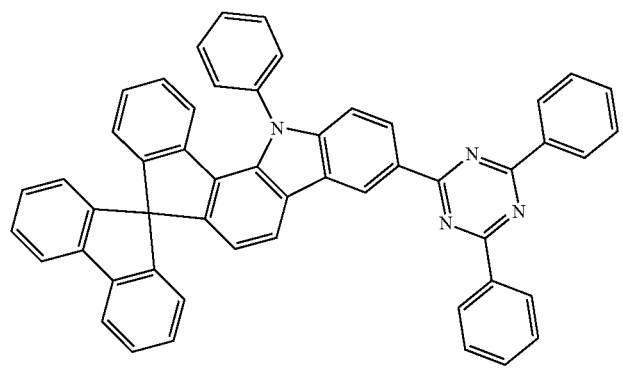 [SMILES: c1ccc(-c2nc(-c3ccccc3)nc(-c3ccc4c(c3)c3ccc5c(c3n4-c3ccccc3)-c3ccccc3C53c4ccccc4-c4ccccc43)n2)cc1]
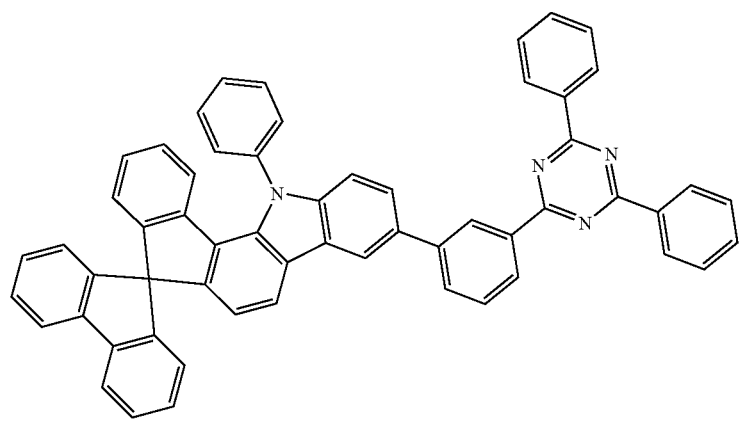 [SMILES: c1ccc(-c2nc(-c3ccccc3)nc(-c3cccc(-c4ccc5c(c4)c4ccc6c(c4n5-c4ccccc4)-c4ccccc4C64c5ccccc5-c5ccccc54)c3)n2)cc1]

-continued
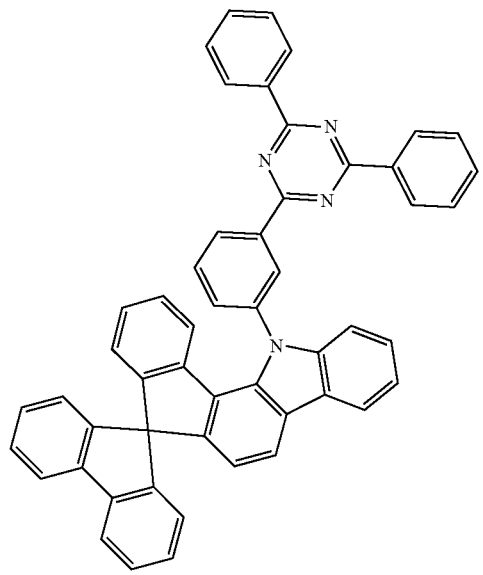 [SMILES: c1ccc(-c2nc(-c3ccccc3)nc(-c3cccc(-n4c5ccccc5c5ccc6c(c54)-c4ccccc4C64c5ccccc5-c5ccccc54)c3)n2)cc1]
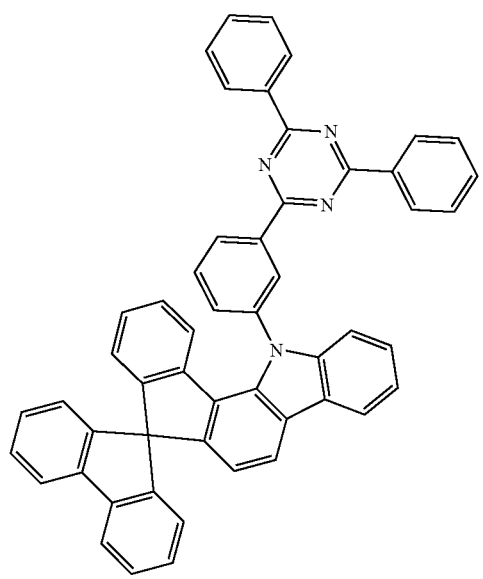 [SMILES: c1ccc(-c2nc(-c3ccccc3)nc(-c3cccc(-n4c5ccccc5c5ccc6c(c54)-c4ccccc4C64c5ccccc5-c5ccccc54)c3)n2)cc1]

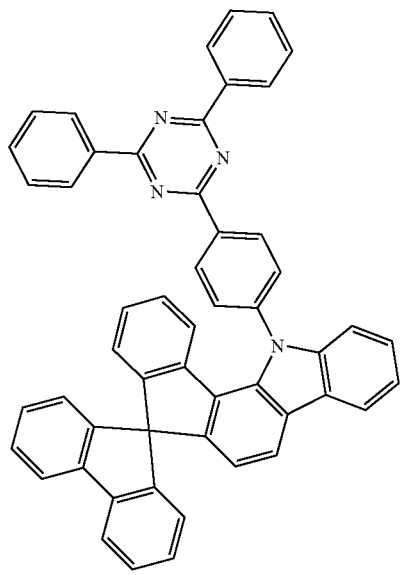 [SMILES: c1ccc(-c2nc(-c3ccccc3)nc(-c3ccc(-n4c5ccccc5c5ccc6c(c54)-c4ccccc4C64c5ccccc5-c5ccccc54)cc3)n2)cc1]
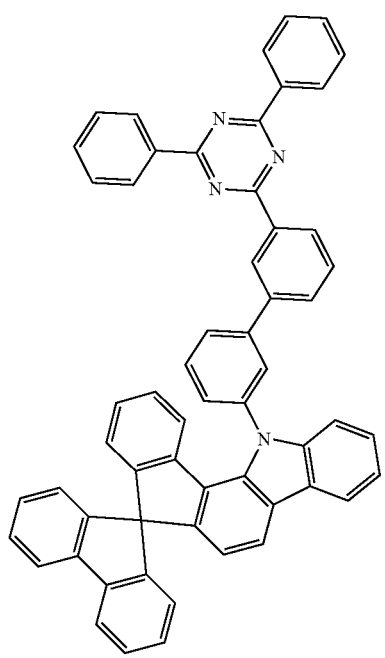 [SMILES: c1ccc(-c2nc(-c3ccccc3)nc(-c3cccc(-c4cccc(-n5c6ccccc6c6ccc7c(c65)-c5ccccc5C75c6ccccc6-c6ccccc65)c4)c3)n2)cc1]

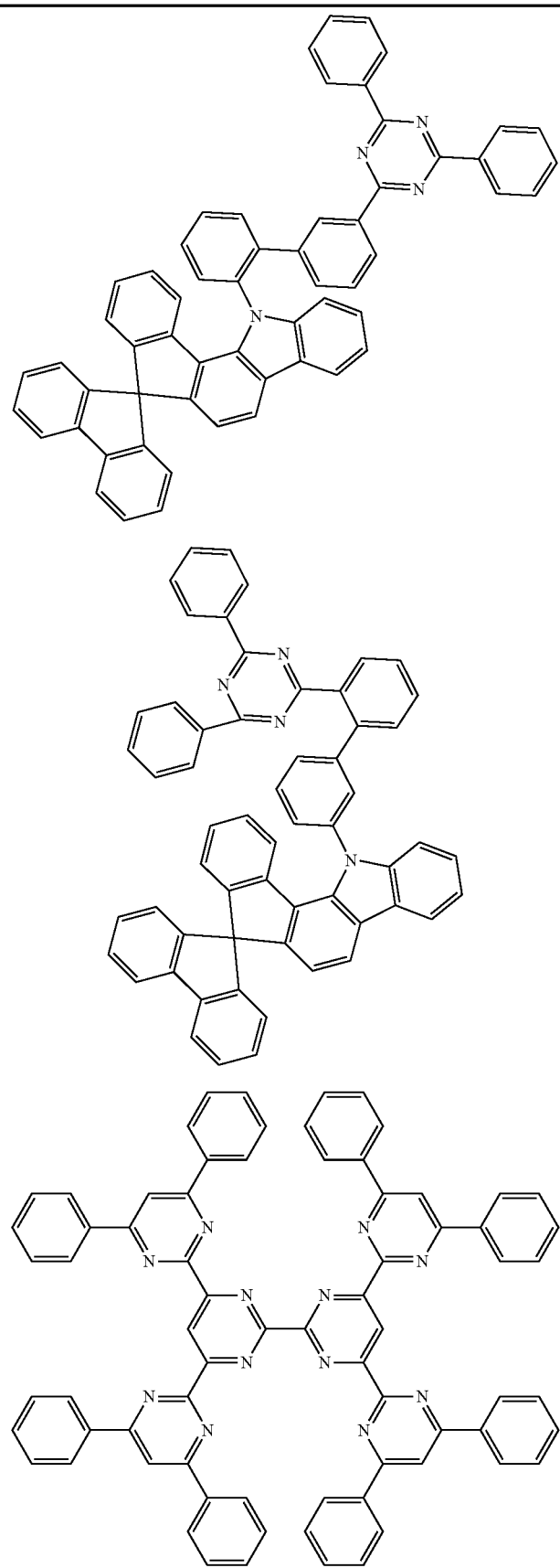

-continued
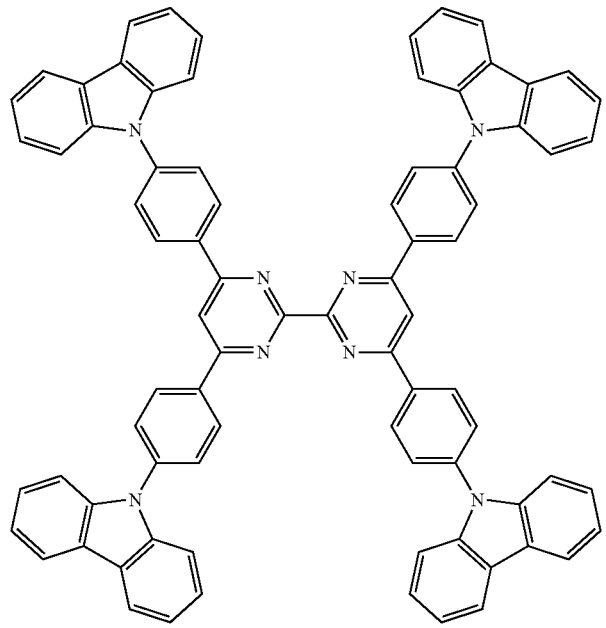 [SMILES: c1ccc2c(c1)c1ccccc1n2-c1ccc(-c2cc(-c3ccc(-n4c5ccccc5c5ccccc54)cc3)nc(-c3nc(-c4ccc(-n5c6ccccc6c6ccccc65)cc4)cc(-c4ccc(-n5c6ccccc6c6ccccc65)cc4)n3)n2)cc1]
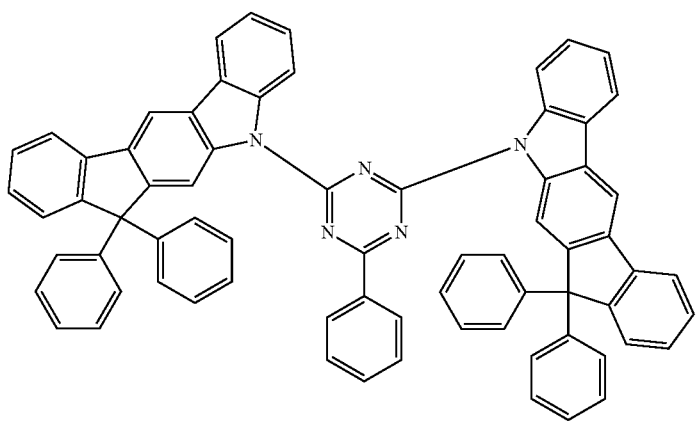 [SMILES: c1ccc(-c2nc(-n3c4ccccc4c4cc5c(cc43)C(c3ccccc3)(c3ccccc3)c3ccccc3-5)nc(-n3c4ccccc4c4cc5c(cc43)C(c3ccccc3)(c3ccccc3)c3ccccc3-5)n2)cc1]
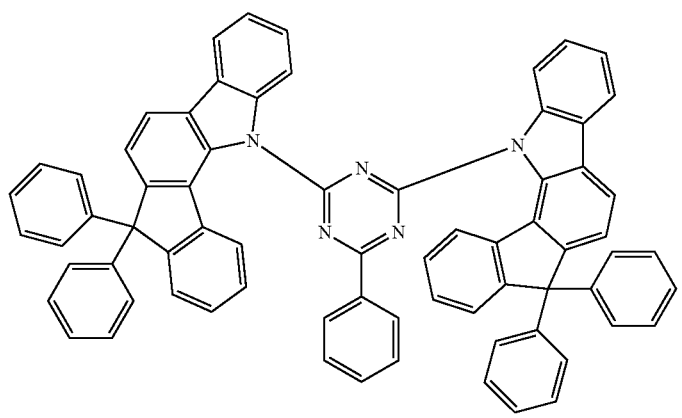 [SMILES: c1ccc(-c2nc(-n3c4ccccc4c4ccc5c(c43)-c3ccccc3C5(c3ccccc3)c3ccccc3)nc(-n3c4ccccc4c4ccc5c(c43)-c3ccccc3C5(c3ccccc3)c3ccccc3)n2)cc1]

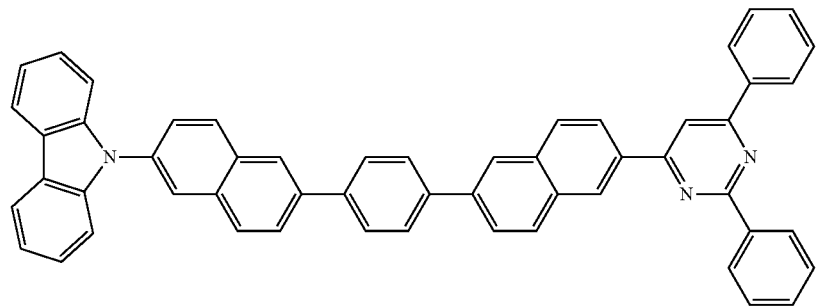 [SMILES: c1ccc(-c2cc(-c3ccc4cc(-c5ccc(-c6ccc7cc(-n8c9ccccc9c9ccccc98)ccc7c6)cc5)ccc4c3)nc(-c3ccccc3)n2)cc1]
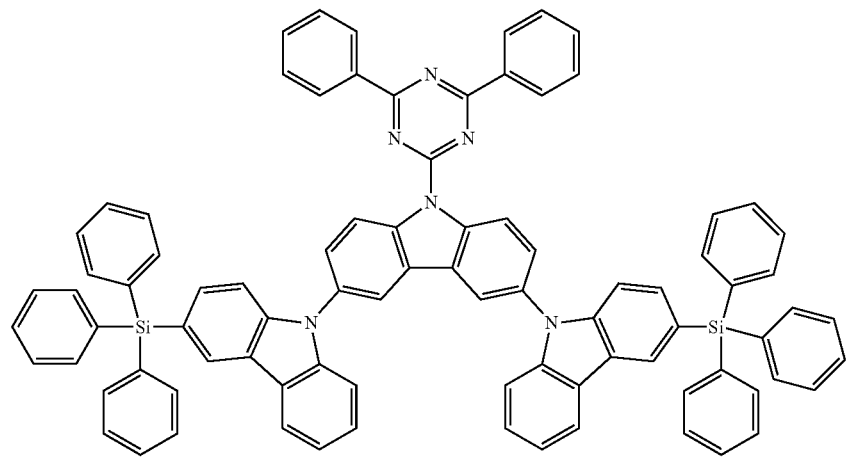 [SMILES: c1ccc(-c2nc(-c3ccccc3)nc(-n3c4ccc(-n5c6ccccc6c6cc([Si](c7ccccc7)(c7ccccc7)c7ccccc7)ccc65)cc4c4cc(-n5c6ccccc6c6cc([Si](c7ccccc7)(c7ccccc7)c7ccccc7)ccc65)ccc43)n2)cc1]
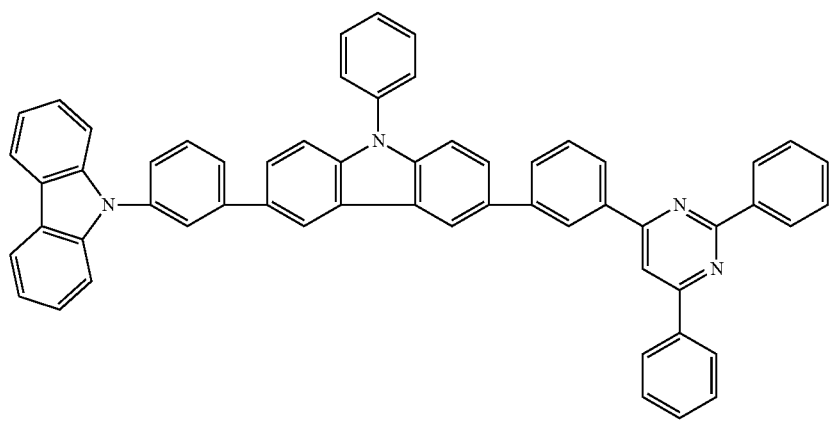 [SMILES: c1ccc(-c2cc(-c3cccc(-c4ccc5c(c4)c4cc(-c6cccc(-n7c8ccccc8c8ccccc87)c6)ccc4n5-c4ccccc4)c3)nc(-c3ccccc3)n2)cc1]

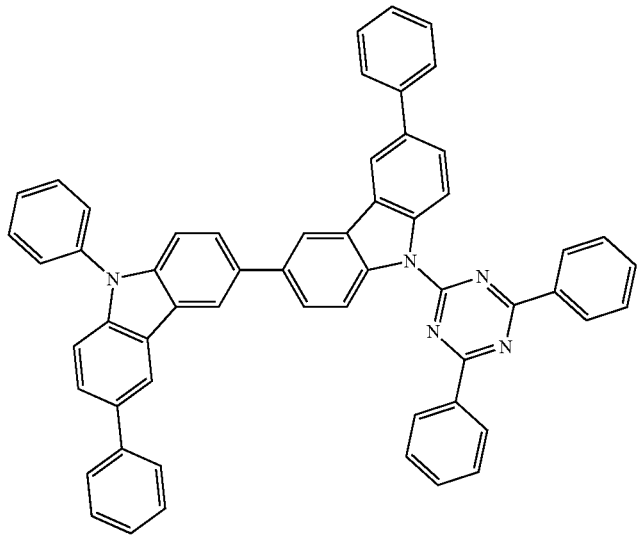 [SMILES: c1ccc(-c2ccc3c(c2)c2cc(-c4ccc5c(c4)c4cc(-c6ccccc6)ccc4n5-c4nc(-c5ccccc5)nc(-c5ccccc5)n4)ccc2n3-c2ccccc2)cc1]
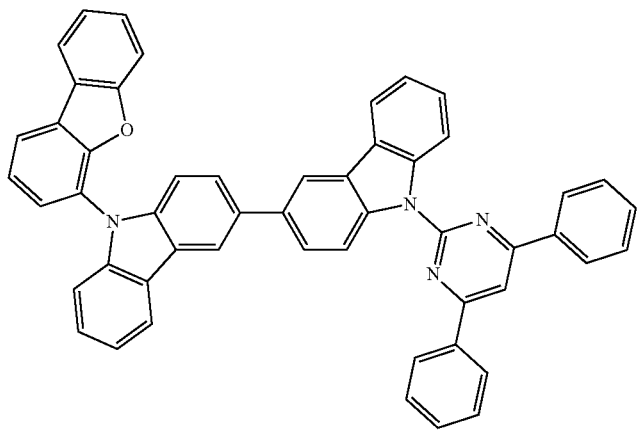 [SMILES: c1ccc(-c2cc(-c3ccccc3)nc(-n3c4ccccc4c4cc(-c5ccc6c(c5)c5ccccc5n6-c5cccc6c5oc5ccccc56)ccc43)n2)cc1]
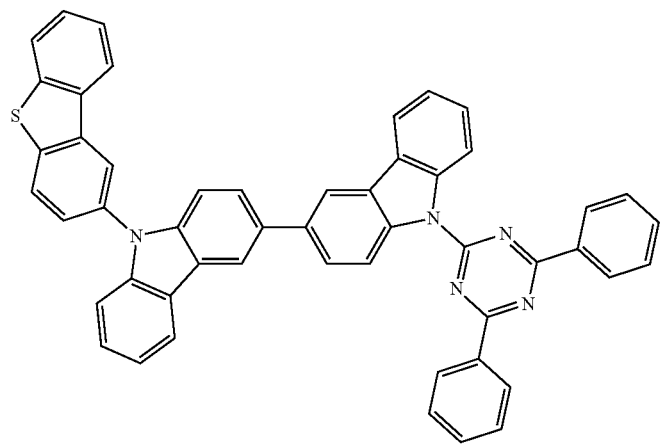 [SMILES: c1ccc(-c2nc(-c3ccccc3)nc(-n3c4ccccc4c4cc(-c5ccc6c(c5)c5ccccc5n6-c5ccc6sc7ccccc7c6c5)ccc43)n2)cc1]

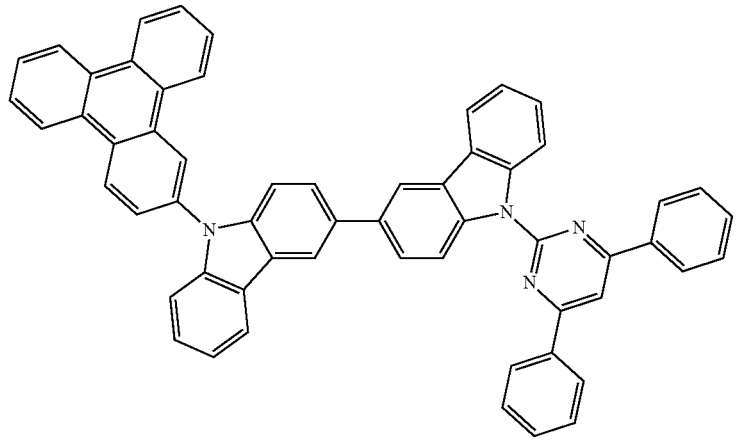 [SMILES: c1ccc(-c2cc(-c3ccccc3)nc(-n3c4ccccc4c4cc(-c5ccc6c(c5)c5ccccc5n6-c5ccc6c7ccccc7c7ccccc7c6c5)ccc43)n2)cc1]

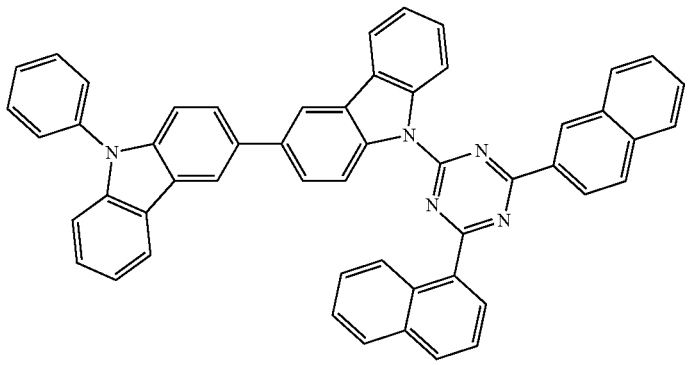 [SMILES: c1ccc(-n2c3ccccc3c3cc(-c4ccc5c(c4)c4ccccc4n5-c4nc(-c5ccc6ccccc6c5)nc(-c5cccc6ccccc56)n4)ccc32)cc1]

When the compound comprising at least one structure of formula (I) or as per the preferred embodiments is used as matrix material for an emitting compound in an emitting layer, it can be used in combination with one or more phosphorescent materials (triplet emitters). Phosphorescence in the context of this invention is understood to mean luminescence from an excited state having higher spin multiplicity, i.e. a spin state >1, especially from an excited triplet state. In the context of this invention, all iridium, platinum, osmium, gold and copper compounds, especially those that are luminescent, are referred to as phosphorescent materials. In that case, the mixture of the compound comprising at least one structure of formula (I) or as per the preferred embodiments and the emitting compound contains between 99% and 1% by weight, preferably between 98% and 10% by weight, more preferably between 97% and 60% by weight and especially between 95% and 70% by weight of the compound comprising at least one structure of formula (I) or as per the preferred embodiments, based on the overall mixture of emitter and matrix material. Correspondingly, the mixture contains between 1% and 99% by weight, preferably between 2% and 90% by weight, more preferably between 3% and 40% by weight and especially between 5% and 30% by weight of the emitter, based on the overall mixture of emitter and matrix material. In the case of use of a mixture of two or more emitters rather than just one emitter, these preferences apply correspondingly to the total proportion of emitters in the emitting layer.

Suitable phosphorescent compounds (=triplet emitters) are especially compounds which, when suitably excited, emit light, preferably in the visible region, and also contain at least one atom of atomic number greater than 20, preferably greater than 38, and less than 84, more preferably greater than 56 and less than 80. Preferred phosphorescence emitters used are compounds containing copper, molybdenum, tungsten, rhenium, ruthenium, osmium, rhodium, iridium, palladium, platinum, silver, gold or europium, especially compounds containing iridium or platinum.

Examples of the above-described emitters can be found in applications WO 00/70655, WO 01/41512, WO 2002/02714, WO 2002/15645, EP 1191613, EP 1191612, EP 1191614, WO 2005/033244, WO 2014/023377, WO 2015/104045, WO 2015/117718 or the as yet unpublished application EP 15000307.7. In addition, suitable emitters are the compounds of the invention detailed above. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Examples of suitable phosphorescent compounds are depicted in the following table:

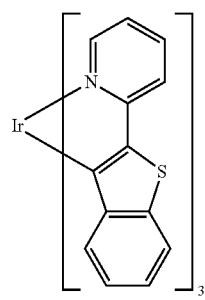
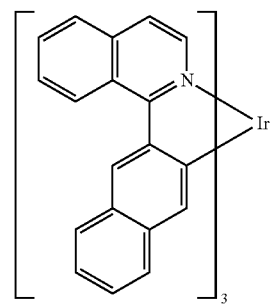
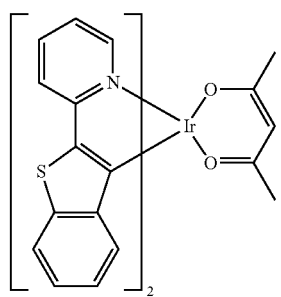
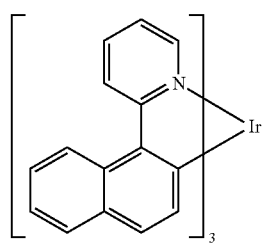
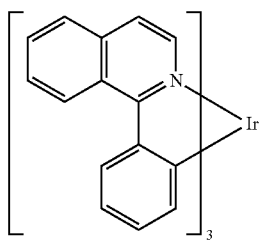
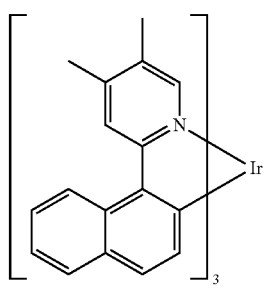
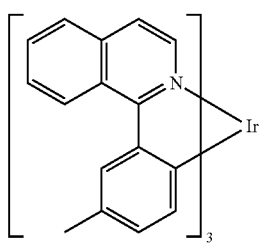
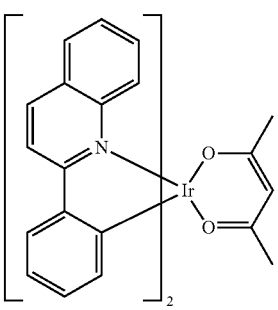
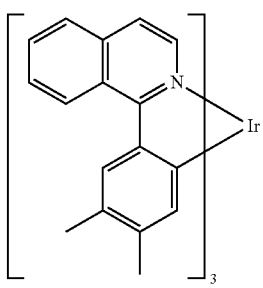
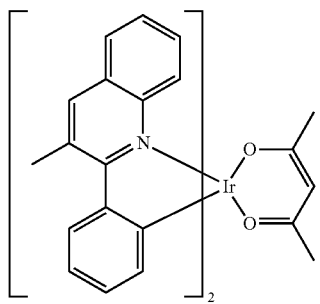

-continued
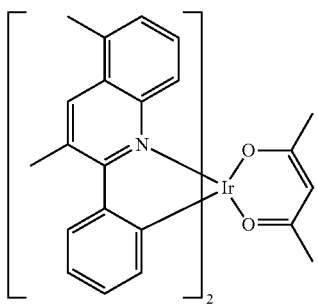
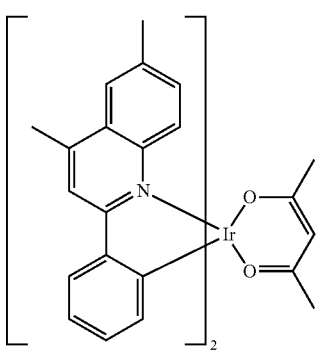
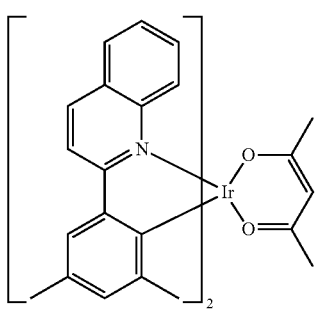
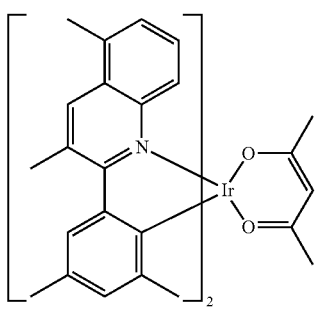
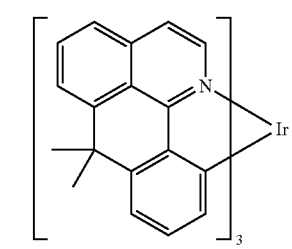
-continued
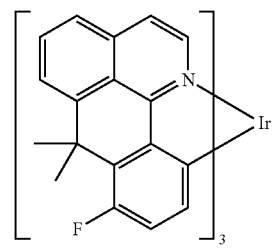
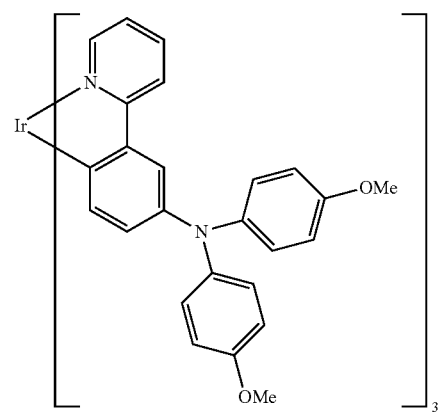
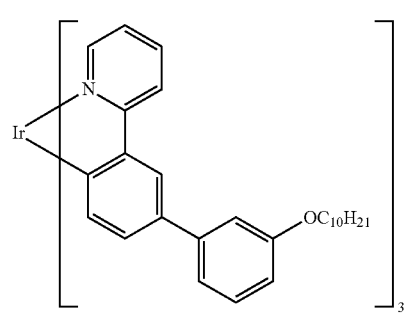
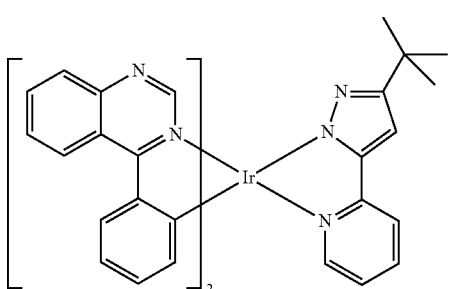
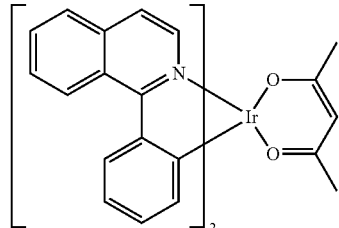

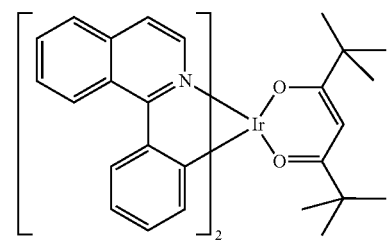
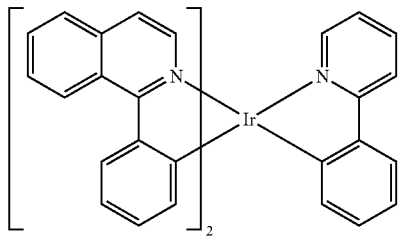
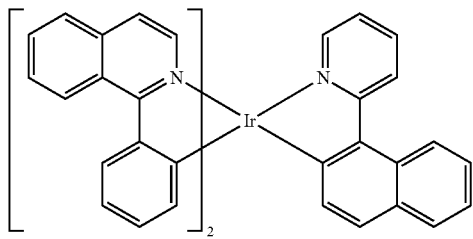
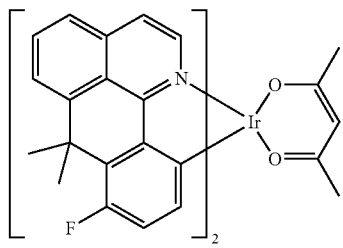
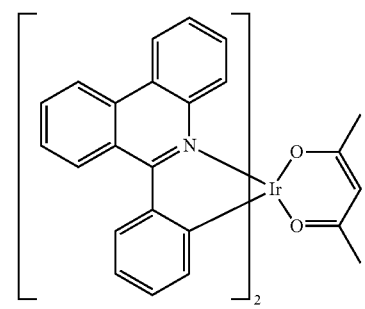
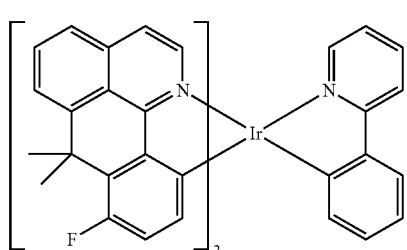
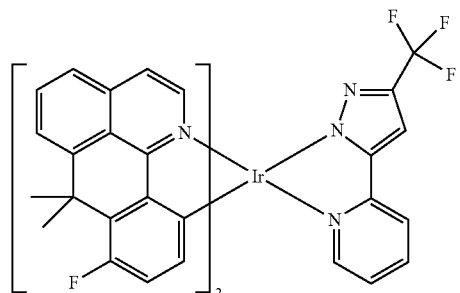
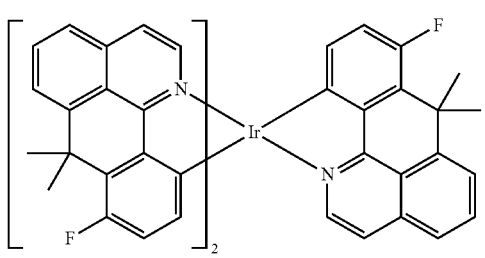
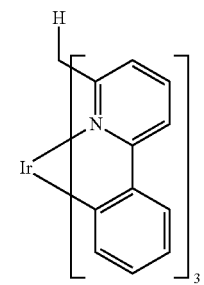
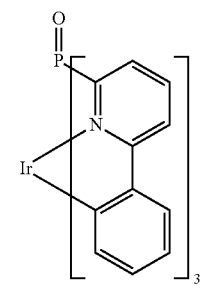
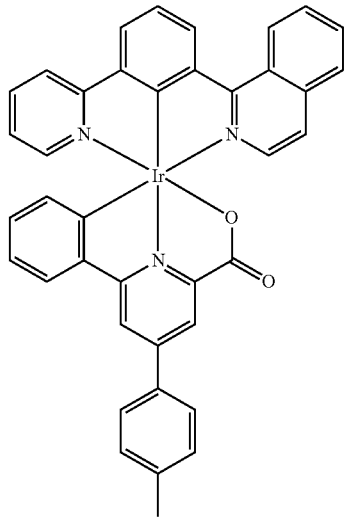

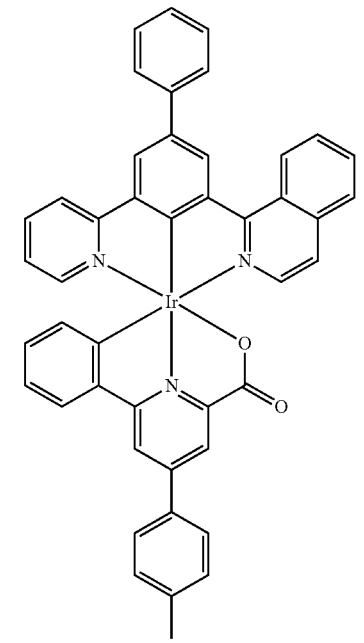
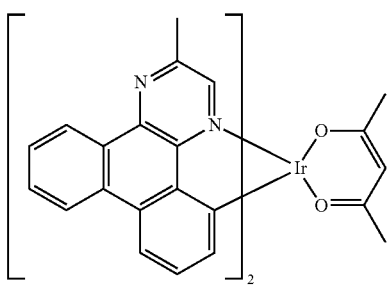
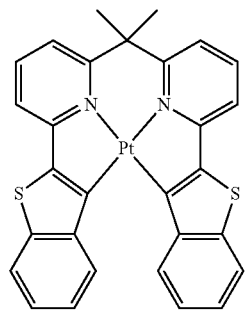
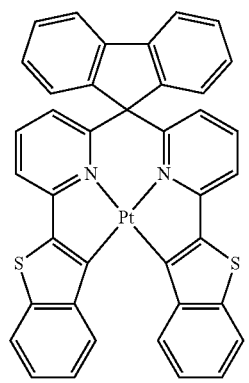
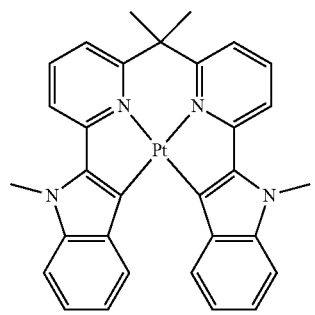
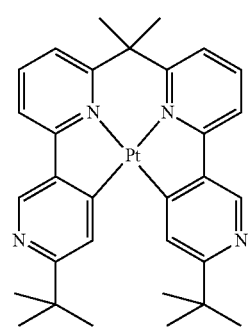
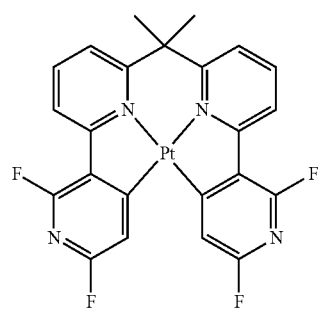
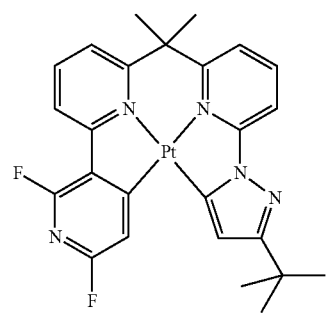

143
-continued
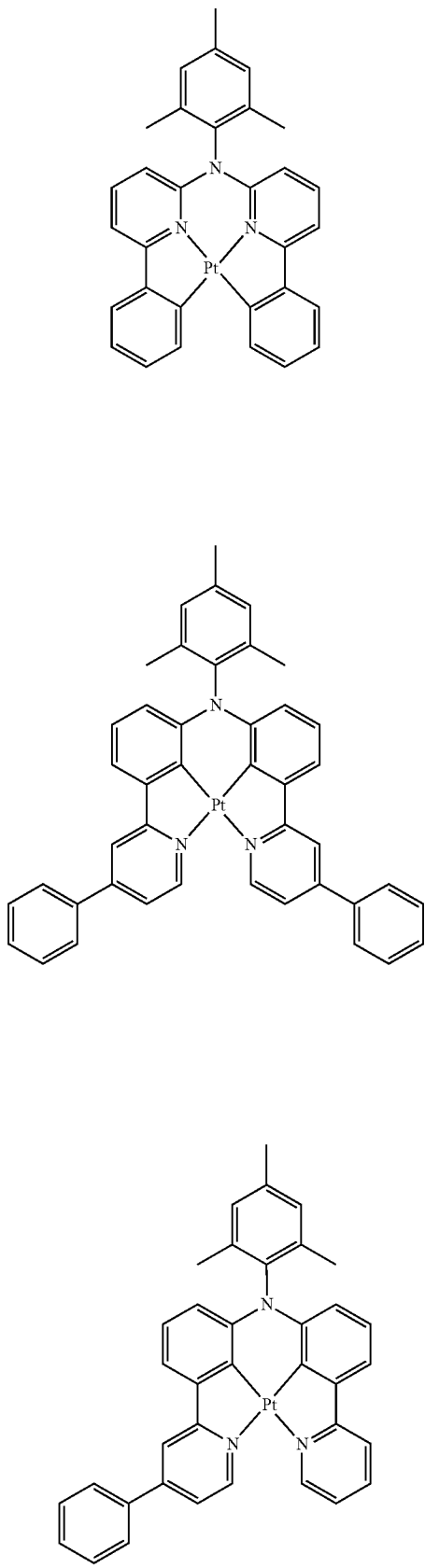
144
-continued
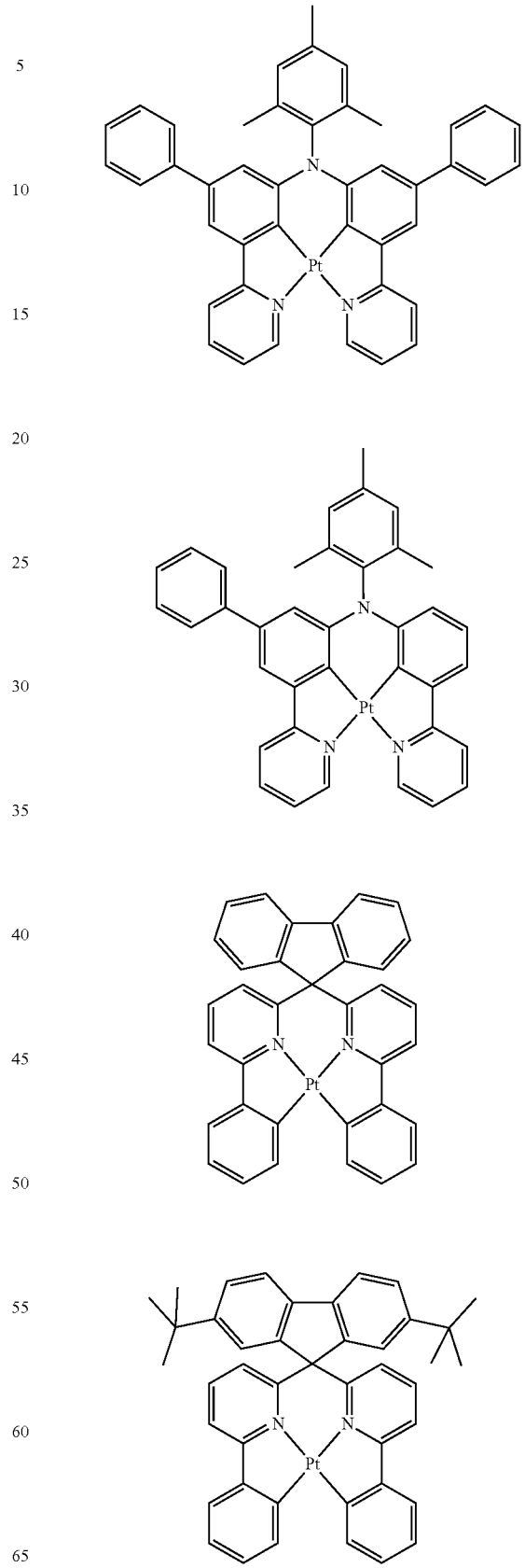

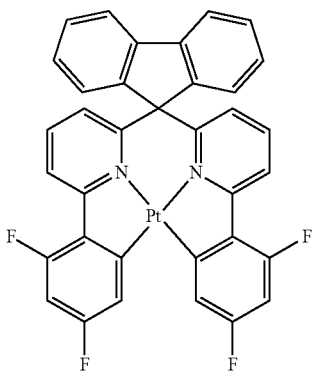
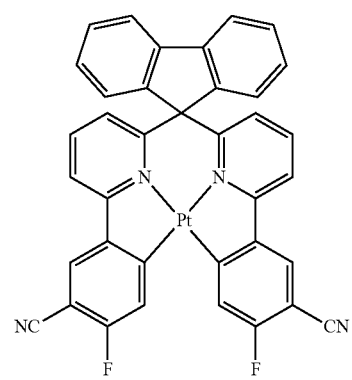
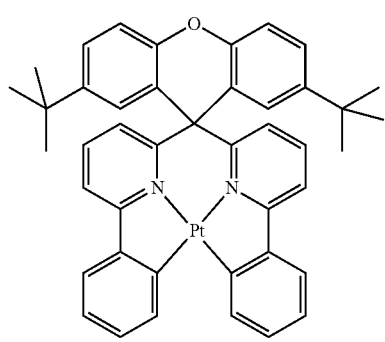
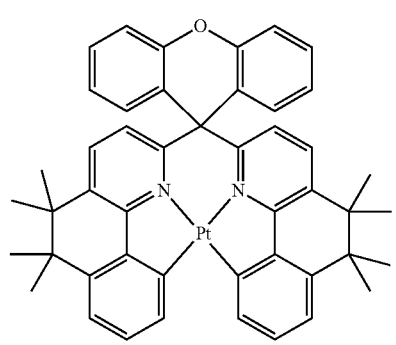
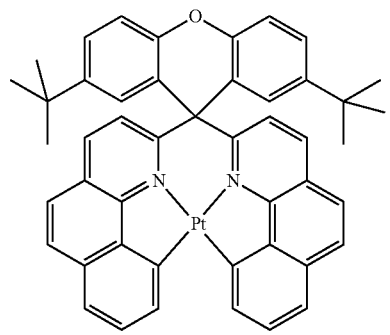
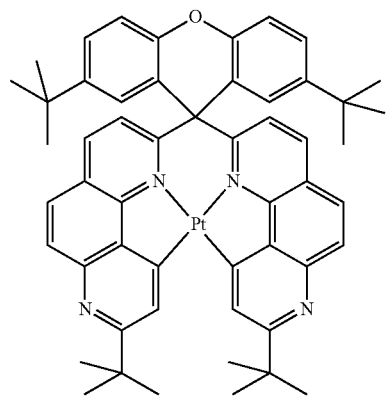
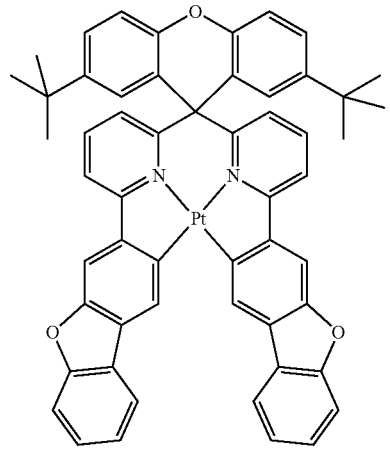
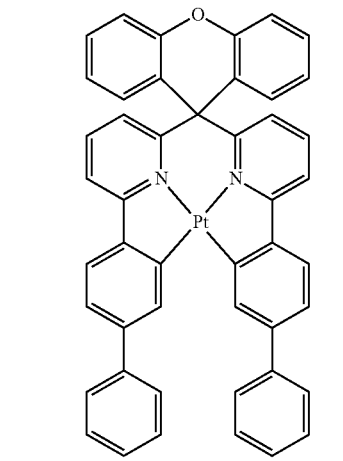

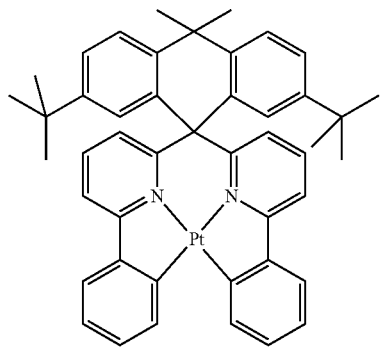
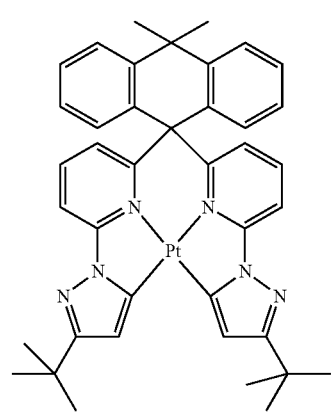
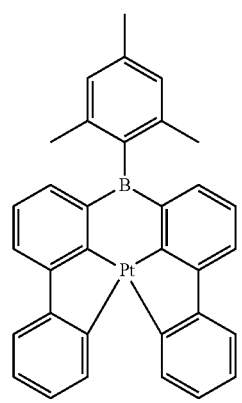
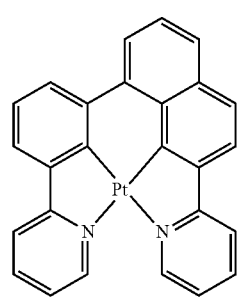
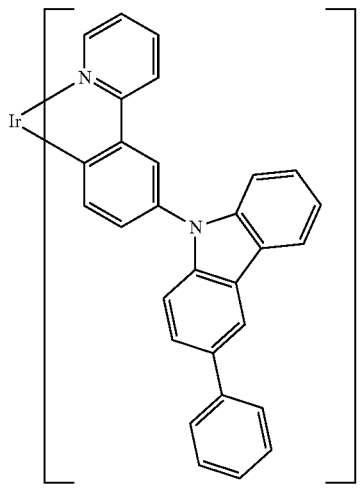
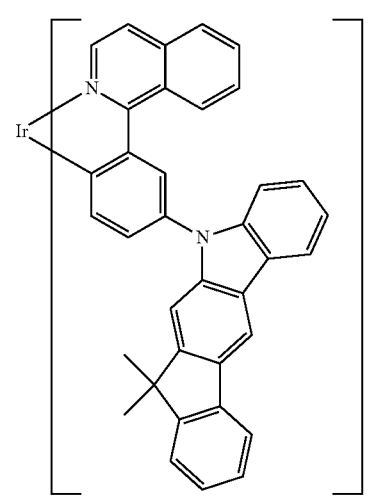
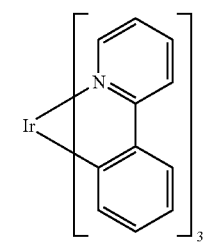
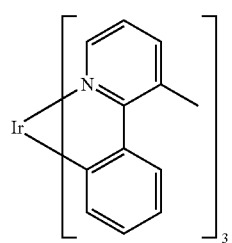

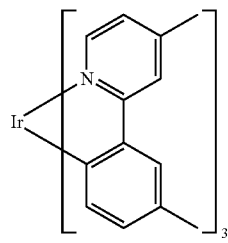
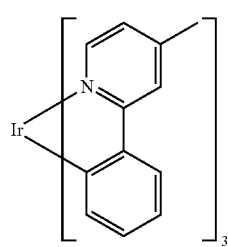
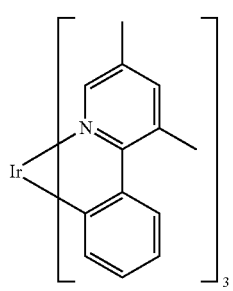
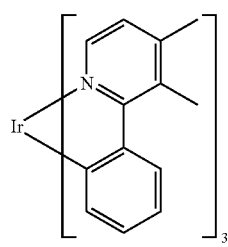
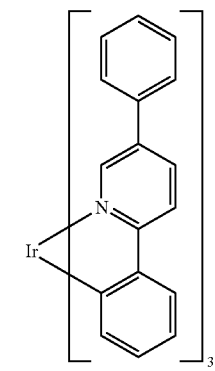
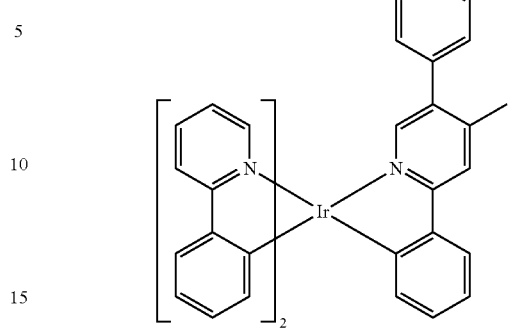
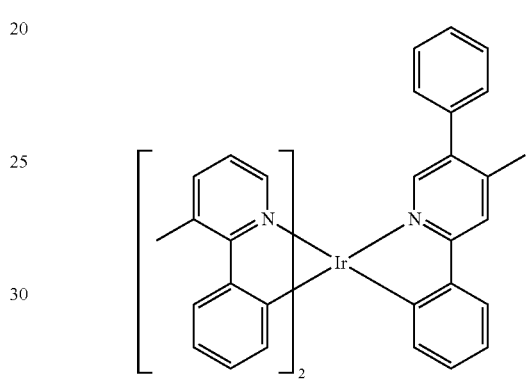
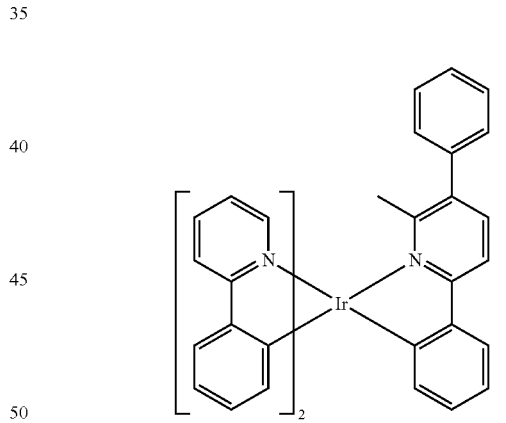
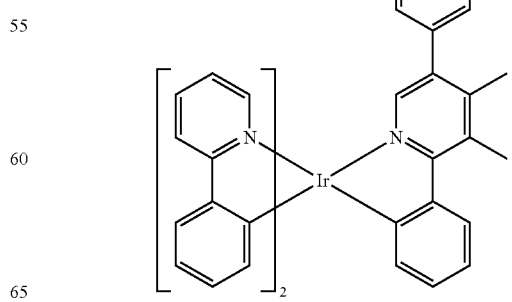

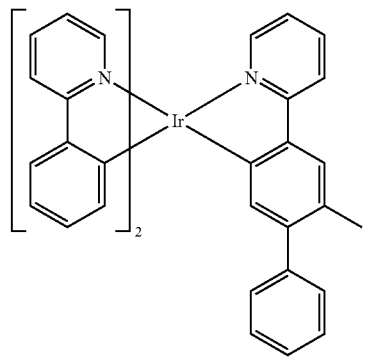
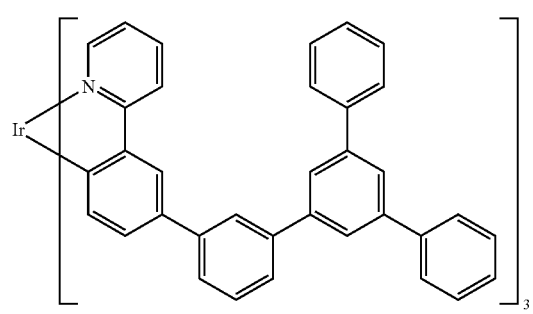
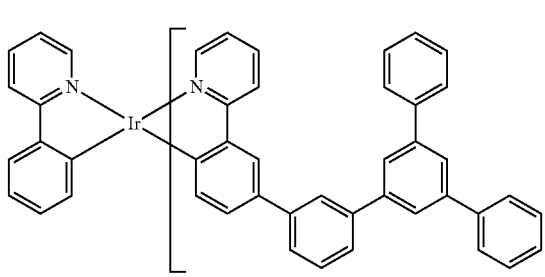
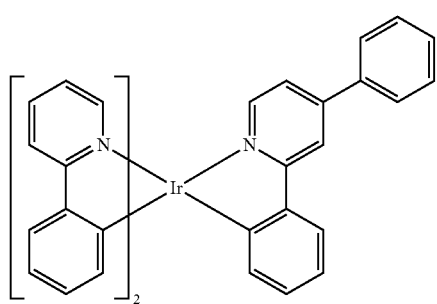
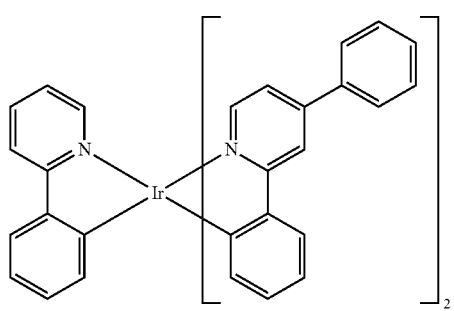
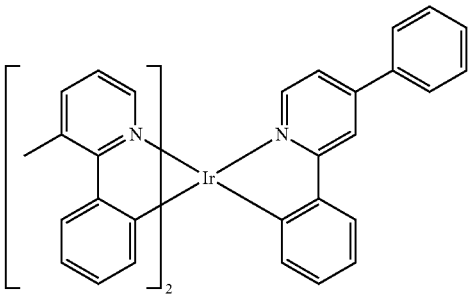
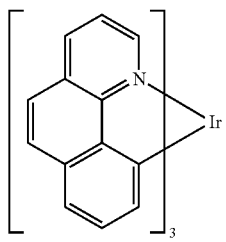
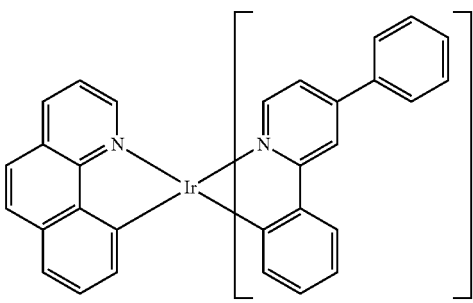
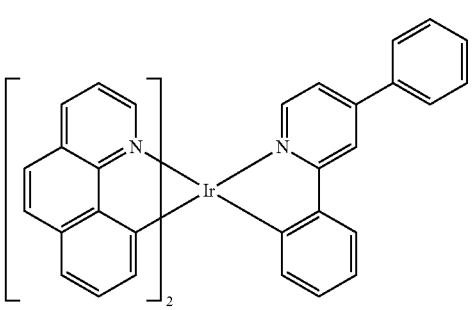
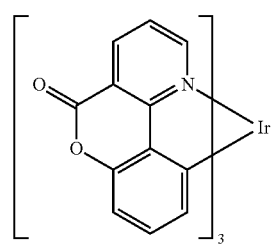

| 153 -continued | 154 -continued |
|---|---|
| 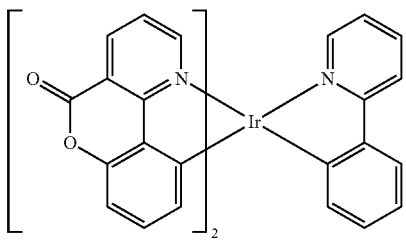 | 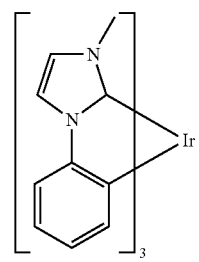 |
| 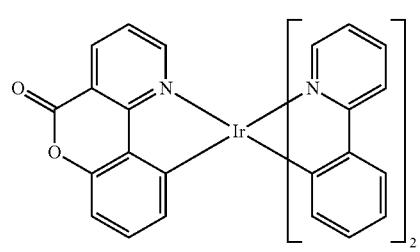 | 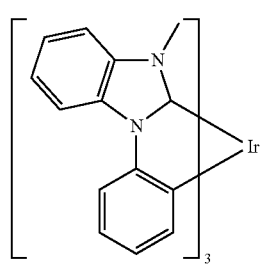 |
| 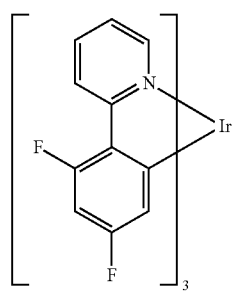 | 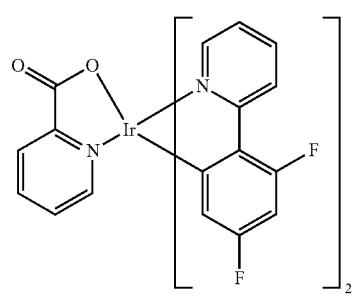 |
| 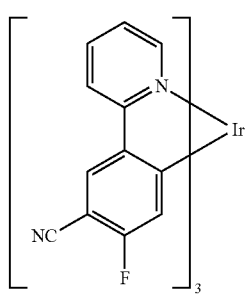 | 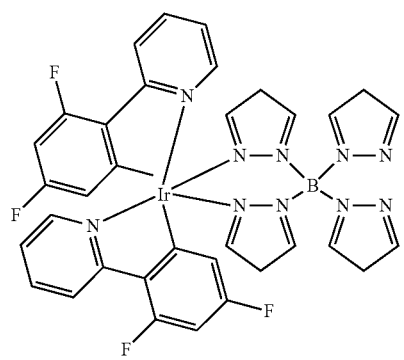 |
| 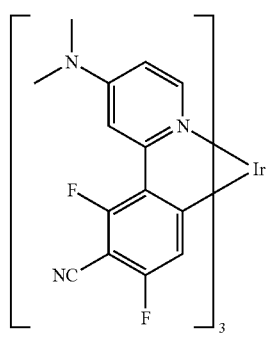 | 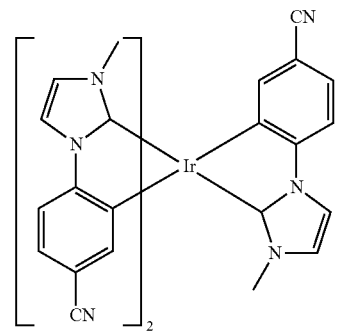 |

155
-continued
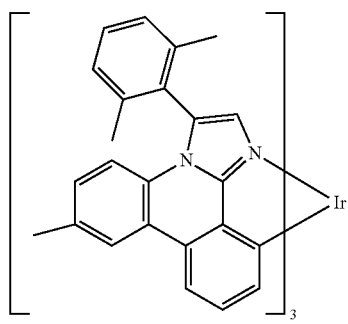
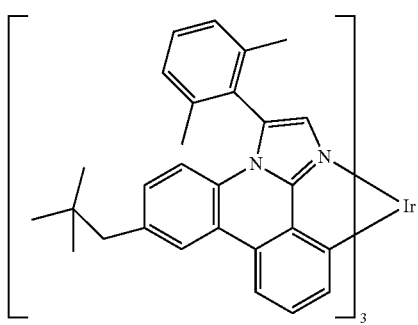
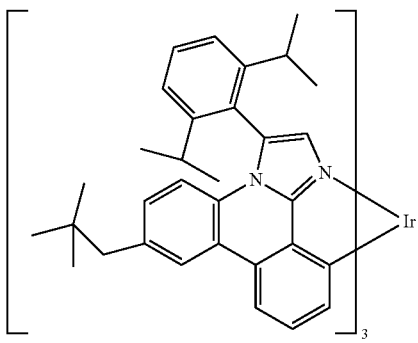
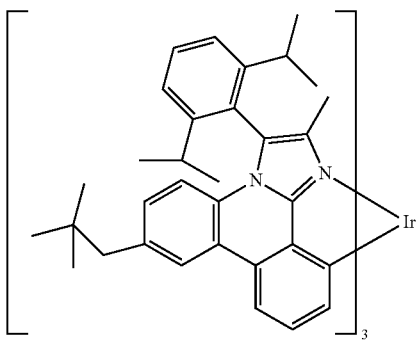
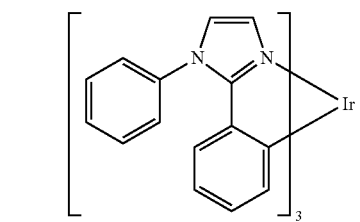
156
-continued
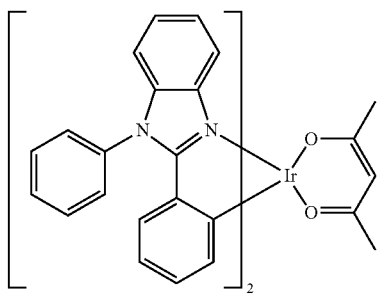
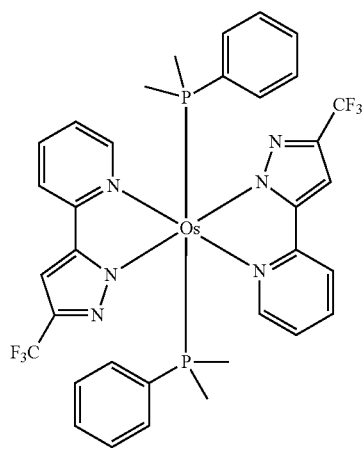
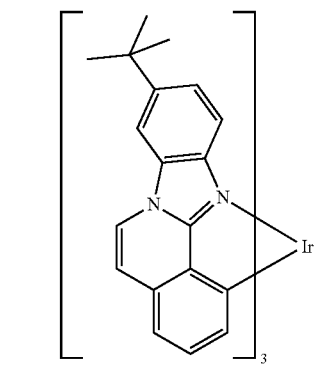
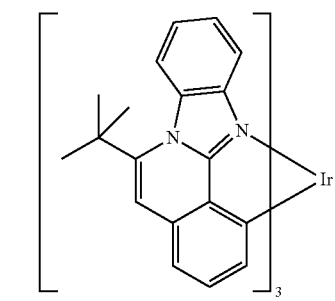

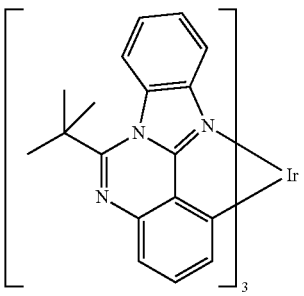
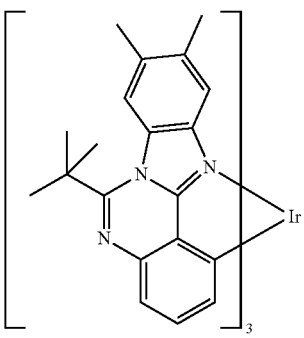
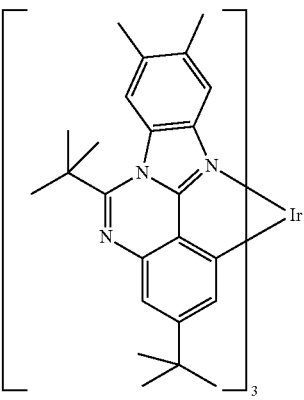
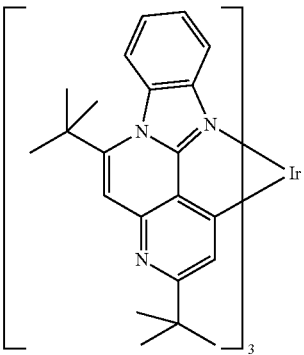

More preferably, the compound comprising at least one structure of formula (I) or as per the preferred embodiments may be used as matrix material in combination with a further matrix material, for example an electron- and/or hole-conducting matrix material, and a phosphorescent compound. In one embodiment of this combination, the compound of the invention is preferably effective as a wide band gap material, as described in detail above and hereinafter. The further matrix material here may be a compound comprising at least one structure of formula (I) or as per the preferred embodi- ments, or a compound which differs from compounds of the present invention. Preferably, the total proportion of the matrix material in the emitting layer is between 99% and 1% by weight, preferably between 98% and 10% by weight, more preferably between 97% and 60% by weight and especially between 95% and 70% by weight of the compound comprising at least one structure of formula (I) or as per the preferred embodiments, based on the overall mixture of emitter and matrix material. Correspondingly, the mixture contains between 1% and 99% by weight, preferably between 2% and 90% by weight, more preferably between 3% and 40% by weight and especially between 5% and 30% by weight of the emitter, based on the overall mixture of emitter and matrix material. In the case of use of a mixture of two or more emitters rather than just one emitter, these preference limits apply correspondingly to the total proportion of emitters in the emitting layer. The proportion of the matrix material of the invention is preferably in the range from 5% to 95% by weight, particularly from 20% to 85% by weight and especially preferably in the range from 50% to 75% by weight, based on the matrix material. Correspondingly, the proportion of the compound used as electron- and/or hole-conducting matrix material is from 95% to 5% by weight, particularly preferably in the range from 80% to 15% by weight and especially preferably in the range from 50% to 25% by weight, based on the matrix material.

When the compound comprising at least one structure of formula (I) or as per the preferred embodiments is used as matrix material for fluorescent compounds, the proportion of the matrix material in the emitting layer is between 50.0% and 99.9% by weight, preferably between 80.0% and 99.5% by weight, more preferably between 90.0% and 99.0% by weight. Correspondingly, the proportion of the dopant is between 0.1% and 50.0% by weight, preferably between 0.1% and 20.0% by weight, more preferably between 0.5% and 15% by weight, most preferably between 1.0% and 10.0% by weight.

Preferred dopants are selected from the class of the monostyrylamines, the distyrylamines, the tristyrylamines, the tetrastyrylamines, the styrylphosphines, the styryl ethers and the arylamines. A monostyrylamine is understood to mean a compound containing one substituted or unsubstituted styryl group and at least one preferably aromatic amine. A distyrylamine is understood to mean a compound containing two substituted or unsubstituted styryl groups and at least one preferably aromatic amine. A tristyrylamine is understood to mean a compound containing three substituted or unsubstituted styryl groups and at least one preferably aromatic amine. A tetrastyrylamine is understood to mean a compound containing four substituted or unsubstituted styryl groups and at least one preferably aromatic amine. The styryl groups are more preferably stilbenes which may also have still further substitution. Corresponding phosphines and ethers are defined in analogy to the amines. An arylamine or an aromatic amine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, preferably having at least 14 aromatic ring atoms. Preferred examples of these are aromatic anthracenamines, aromatic anthracenediamines, aromatic pyrenamines, aromatic pyrenediamines, aromatic chrysenamines or aromatic chrysenediamines. An aromatic anthracenamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyrenamines, pyrenediamines, chrysenamines and chrysenediamines are defined analogously, where the diarylamino groups are bonded to the pyrene preferably in the 1 position or 1,6 positions. Further preferred dopants are selected from indenofluorenamines and -fluorenediamines, for example according to WO 06/122630, benzoindenofluorenamines and -fluorenediamines, for example according to WO 08/006449, and dibenzoindenofluorenamines and -fluorenediamines, for example according to WO 07/140847. Examples of dopants from the class of the styrylamines are substituted or unsubstituted tristilbenamines or the dopants described in WO 06/000388, WO 06/058737, WO 06/000389, WO 07/065549 and WO 07/115610. Further suitable fluorescent dopants are the fused aromatic hydrocarbons disclosed in WO 2010/012328.

In a further embodiment of the invention, the compounds comprising at least one structure of formula (I) or as per the preferred embodiments are used as hole transport material or as hole injection material or as electron blocker material or as exciton blocker material. In that case, the compounds are preferably substituted by at least one $N(Ar)_2$ group, preferably by at least two $N(Ar)_2$ groups, and/or they contain further groups which improve hole transport. The compound is preferably used in a hole transport layer or in a hole injection layer or in an electron blocker layer or in an exciton blocker layer. A hole injection layer in the context of this invention is a layer directly adjoining the anode. A hole transport layer in the context of this invention is a layer between a hole injection layer and an emission layer. An electron blocker layer or exciton blocker layer in the context of this invention is a layer which directly adjoins an emitting layer on the anode side. When the compounds comprising at least one structure of formula (I) are used as hole transport material or as hole injection material, it may be preferable when they are doped with electron acceptor compounds, for example with $F_4$-TCNQ or with compounds as described in EP 1476881 or EP 1596445.

In yet a further embodiment of the invention, the compounds comprising at least one structure of formula (I) are used as electron transport material or as hole blocker material in an electron transport layer or a hole blocker layer. It is preferable here when at least one of the substituents is a heteroaryl group which is an electron-deficient heterocycle, for example imidazole, pyrazole, thiazole, benzimidazole, benzothiazole, oxadiazole, benzothiadiazole, phenanthroline, etc., or is C(=O)Ar, P(=O)$Ar_2$, S(=O)Ar or S(O)$_2$Ar. It may additionally be preferable when the compound is doped with electron donor compounds. A hole blocker layer in the context of this invention is a layer which is disposed between an emitting layer and an electron transport layer and directly adjoins the emitting layer. When the compound comprising at least one structure of formula (I) is used as electron transport material, it may be preferable to use it as a mixture with a further compound. Preferred mixture components are alkali metal compounds, preferably lithium compounds, more preferably Liq (lithium quinolinate) or Liq derivatives.

Additionally preferred is an organic electroluminescent device, characterized in that one or more layers are coated by a sublimation process. In this case, the materials are applied by vapour deposition in vacuum sublimation systems at a pressure of less than $10^{-5}$ mbar, preferably less than $10^{-6}$ mbar. However, it should be noted that the pressure may also be even lower, for example less than $10^{-7}$ mbar.

Preference is likewise given to an organic electroluminescent device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example, M. S. Arnold et al., *Appl. Phys. Lett.* 2008, 92, 053301).

Preference is additionally given to an organic electroluminescent device, characterized in that one or more layers are produced from solution, for example by spin-coating, or by any printing method, for example screen printing, flexographic printing or offset printing, but more preferably LITI (light-induced thermal imaging, thermal transfer printing) or inkjet printing. For this purpose, soluble compounds are needed. High solubility can be achieved by suitable substitution of the compounds. It is possible here to apply not just solutions of individual materials but also solutions containing a plurality of compounds, for example matrix material and dopant.

The organic electroluminescent device can also be produced as a hybrid system by applying one or more layers from solution and applying one or more other layers by vapour deposition. For example, it is possible to apply an emitting layer comprising a compound comprising at least one structure of formula (I) and a phosphorescent dopant from solution, and to apply a hole blocker layer and/or an electron transport layer thereto by vapour deposition under reduced pressure. It is likewise possible to apply the emitting layer comprising a compound comprising at least one structure of formula (I) and a phosphorescent dopant by vapour deposition under reduced pressure, and to apply one or more other layers from solution. Alternatively or additionally, it is also possible, for example, to apply an emitting layer from solution and to apply an electron transport layer comprising a compound comprising at least one structure of formula (I), optionally in combination with an organic alkali metal compound, thereto by vapour deposition under reduced pressure.

These methods are known in general terms to those skilled in the art and can be applied by those skilled in the art without difficulty to organic electroluminescent devices comprising compounds comprising at least one structure of formula (I) or the above-detailed preferred embodiments.

The compounds of the invention, when used in organic electroluminescent devices, have the following surprising advantages over the prior art:

1. The compounds of the invention have high thermal stability and can be sublimed without decomposition.
2. The compounds of the invention have high solubility in standard organic solvents, for example toluene, and very good film formation properties, and are therefore of particularly good suitability for processing from solution.
3. The compounds of the invention are especially suitable as wide band gap materials and lead to an improvement in efficiency.
4. The OLEDs produced with the compounds of the invention generally have a very long lifetime.
5. The OLEDs produced with the compounds of the invention generally have a very high quantum efficiency.

The present application text is aimed at the use of the compounds of the invention in relation to OLEDs and PLEDs and the corresponding displays. In spite of this restriction of the description, it is possible for the person skilled in the art, without further inventive activity, also to use the compounds of the invention in other electronic devices, for example in organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) or organic photoreceptors.

The use of the compounds of the invention in the corresponding devices, and likewise these devices themselves, likewise form part of the subject-matter of the present invention.

The invention is described in more detail by the examples which follow, without any intention of restricting it thereby. The person skilled in the art is able, without exercising inventive skill, to prepare further compounds of the invention and use them in organic electronic electroluminescent devices.

EXAMPLES

All syntheses are conducted in an argon atmosphere and in dry solvents, unless stated otherwise. The figures in brackets for the substances known from the literature are the corresponding CAS numbers.

Part A: Preparation of Compounds of the Invention

A.1 Preparation of 3,3'-dibromobenzophenone K1

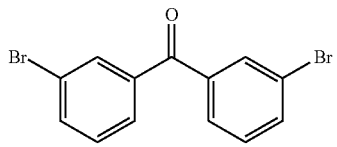 [SMILES: O=C(c1cccc(Br)c1)c1cccc(Br)c1]

3,3'-Dibromobenzophenone K1 can be prepared according to J. Mater. Chem. C 2014, 2, 2028-2036.

A.2 Preparation of 9,9-bis(3-bromophenyl)fluorene F(Br)$_2$

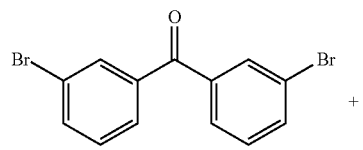

+

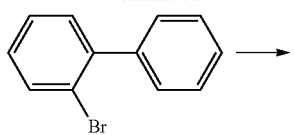

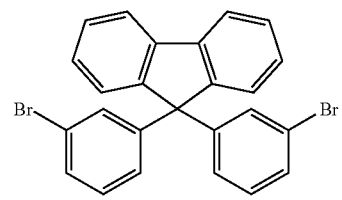

About 10 ml of a solution of 2-bromobiphenyl (80.0 g, 343 mmol) and 1,2-dibromoethane (3.6 ml, 43 mmol) in a mixture of 640 ml of toluene, 520 ml of tetrahydrofuran and 60 ml of ethylene glycol dimethyl ether are added to 8.8 g of magnesium (334 mmol) and heated. After onset of the reaction, the heating is removed and the remaining solution is added dropwise in such a way that reflux is maintained. On completion of addition, the mixture is heated to reflux for 1 h. Subsequently, under gentle reflux, a solution of the ketone K1 (80.0 g, 235 mmol) in 800 ml of tetrahydrofuran is added dropwise and the mixture is stirred under reflux for 5 h. The heating is removed and the mixture is stirred for 14 h. The solvents are removed completely on a rotary evapourator. The remaining residue is taken up in a mixture of 920 ml of glacial acetic acid and 13.2 ml of a 33% solution of hydrogen bromide in acetic acid, and heated to reflux for 6 h. After removing the heating, the mixture is stirred for 16 h. The solid material formed is filtered off with suction, washed with about 150 ml of glacial acetic acid and three times with 250 ml each time of ethanol and then dried in a vacuum drying cabinet. This leaves 101.6 g (213 mmol, 91% of theory) of the product as a light grey solid having a purity of about 99% by 1H NMR.

In an analogous manner, it is possible to prepare the following compound BuF(Br)$_2$ from the ketone K1 and the appropriate bromide:

| Ex. | Bromide | Product | Yield |
|---|---|---|---|
| BuF(Br)$_2$ | ![structure with Br and [70728-89-1]] | ![fluorene structure with Br substituents] | 82% |

A.3 Preparation of Substituted 9,9-Diphenylfluorene Derivatives
The boronic acids and boronic esters used in the syntheses described hereinafter are summarized in the following table:
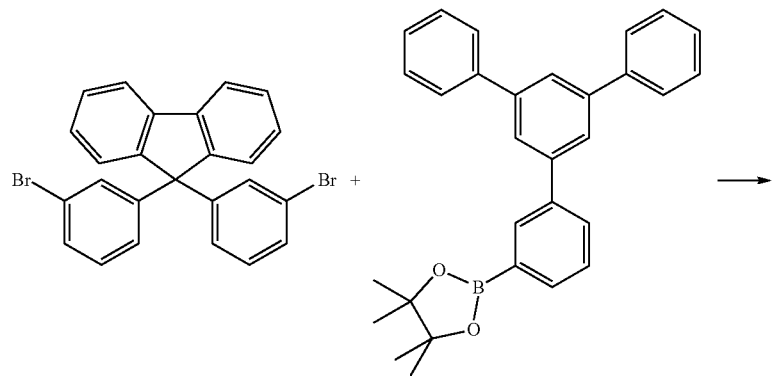
A.3.1 Preparation of F(BS1)$_2$
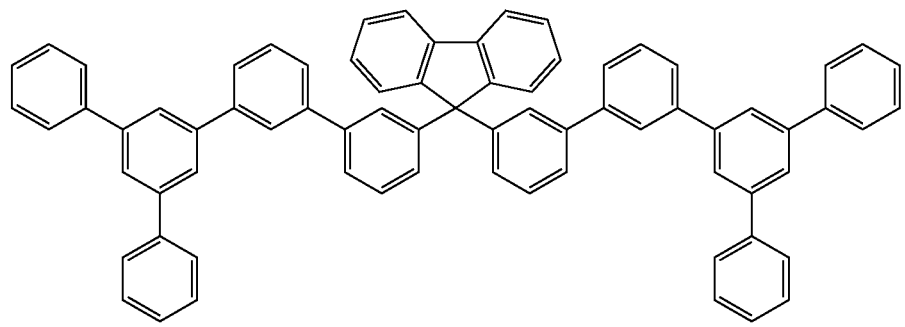 [SMILES: c1ccc(-c2cc(-c3ccccc3)cc(-c3cccc(-c4cccc(C5(c6cccc(-c7cccc(-c8cc(-c9ccccc9)cc(-c9ccccc9)c8)c7)c6)c6ccccc6-c6ccccc65)c4)c3)c2)cc1]

9,9-Bis-(3-bromophenyl)fluorene F(Br)$_2$ (15.4 g, 32.4 mmol), 2-[3-(3,5-diphenylphenyl)phenyl]-4,4,5,5-tetramethyl-1,3,2-dioxoborolane (28.7 g, 66.4 mmol), 1.87 g of tetrakis(triphenylphosphine)palladium(0) and 100 ml of a 20% solution of tetraethylammonium hydroxide in water are heated under reflux in 350 ml of tetrahydrofuran for 14 h. After cooling, the solvents are removed on a rotary evapourator. The remaining residue is hot-extracted with about 300 ml of ethyl acetate over a bed of alumina (basic, activity level 1). After removing the heating, the mixture is stirred at room temperature for a further 48 h. The solid material formed is filtered off with suction, recrystallized five times from toluene and finally fractionally sublimed twice (390° C., p about 10$^{-5}$ mbar). This leaves 10.2 g (11.0 mmol, 34% of theory) as a colourless solid having a purity of 99.9% by HPLC.

In an analogous manner, it is possible to prepare the following compounds:

| Ex. | Fluorene | Boronic acid/ester | Product | Yield |
|---|---|---|---|---|
| F(BS3)$_2$ | F(Br)$_2$ | | | 41% |
| F(BS4)$_2$ | F(Br)$_2$ | | | 28% |
| BuF(BS4)$_2$ | BuF(Br)$_2$ | | | 32% |

A.3.2 Preparation of Asymmetrically Substituted 9,9-diphenylfluorenes

Method A)

Compounds asymmetrically substituted with respect to the mirror plane of the 9,9-diphenylfluorene can be obtained in analogy to the preparation of F(BS1)$_2$ by simultaneous reaction of F(Br)$_2$ with 0.55 equivalent each of two different boronic acids and/or boronic esters (Boron A and Boron B in Table 1) as mixtures of three products, as shown by way of example by the following scheme:

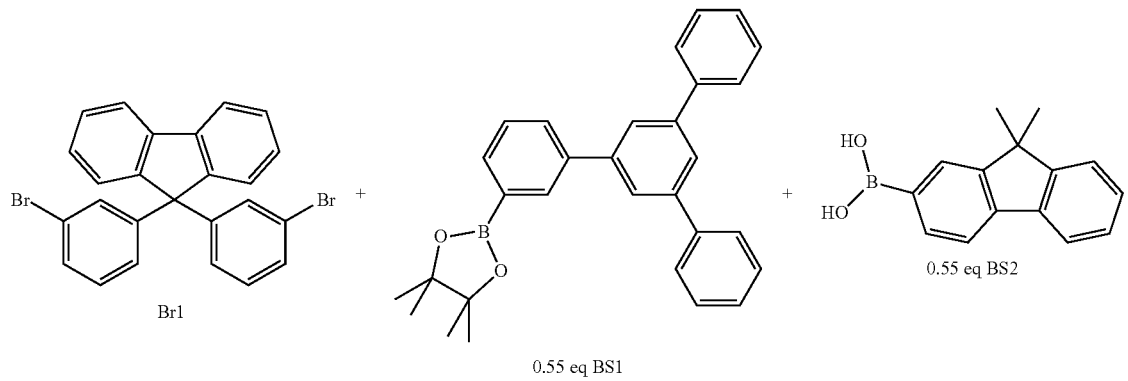
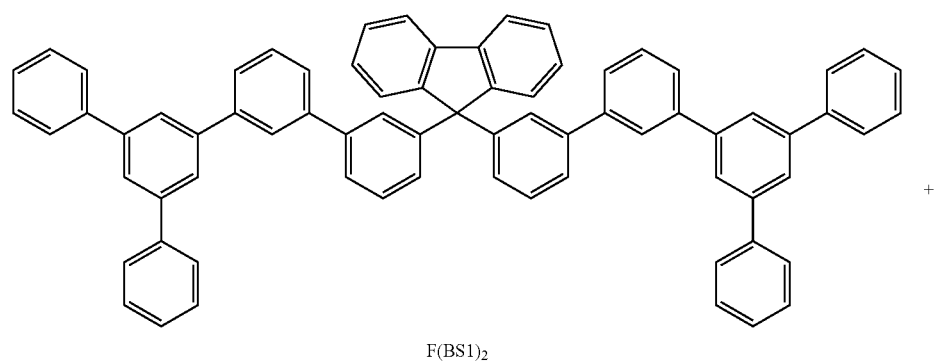
F(BS1)₂ +
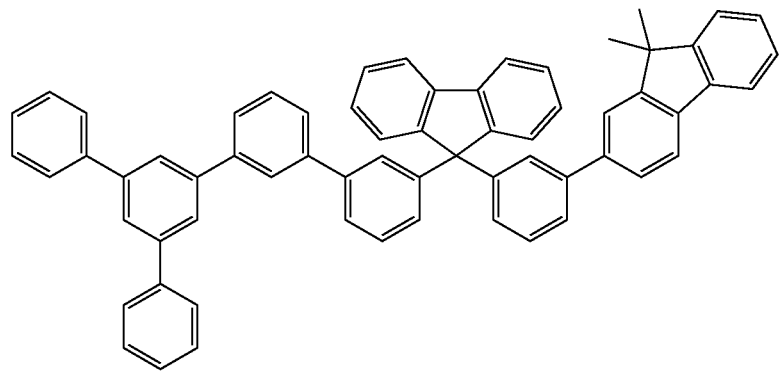
F(BS1)(BS2) +
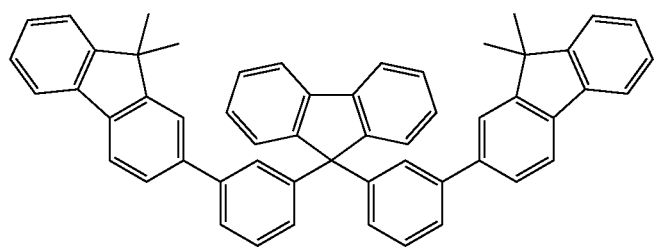
F(BS2)₂

The crude products of this mixed substitution can be separated by chromatography (e.g. CombiFlash Torrent from A. Semrau).

Chromatographic media and eluent mixtures suitable for this purpose are known to those skilled in the art. The products thus isolated can optionally finally be purified further by recrystallization and/or sublimation analogously to the preparation of F(BS1)$_2$ as per A.3.1.

TABLE 1

Products from the simultaneous reaction of F(Br)$_2$ with two boronic acids/boronic esters (Boron A and Boron B) by Method A

| Ex. | Boron A | Boron B | Product isolated | Yield |
|---|---|---|---|---|
| F(BS1)$_2$ | 0.55 eq BS1 | 0.55 eq BS2 | 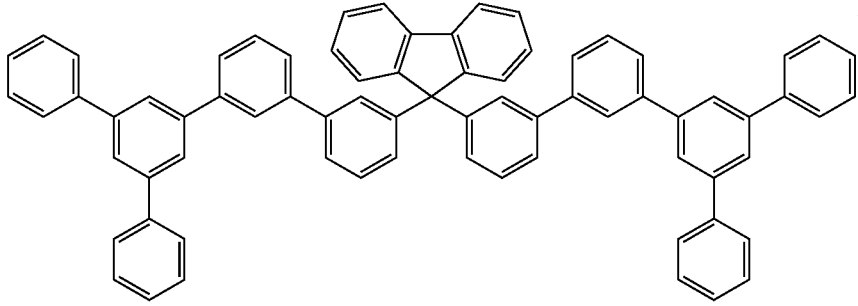 | 23% |
| B(BS1)(BS2) | | | 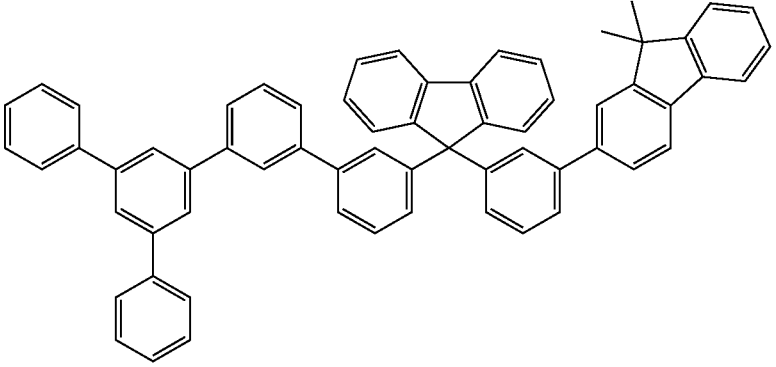 [SMILES: CC1(C)c2ccccc2-c2ccc(-c3cccc(C4(c5cccc(-c6cccc(-c7cc(-c8ccccc8)cc(-c8ccccc8)c7)c6)c5)c5ccccc5-c5ccccc54)c3)cc21] | 30% (22%) |
| F(BS2)$_2$ | | | 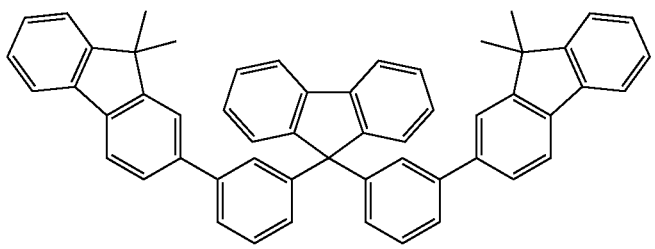 [SMILES: CC1(C)c2ccccc2-c2ccc(-c3cccc(C4(c5cccc(-c6ccc7c(c6)C(C)(C)c6ccccc6-7)c5)c5ccccc5-c5ccccc54)c3)cc21] | 32% |

The yield reported is based in each case on the products isolated after chromatographic separation and, in brackets, after sublimation thereof.

Method B)

Further compounds asymmetrically substituted with respect to the mirror plane of the 9,9-diphenylfluorene can be obtained in analogy to Method A by reaction of F(Br)$_2$ with just 0.5 equivalent of a boronic acid or boronic ester as a mixture of three products, as shown by way of example by the following scheme:

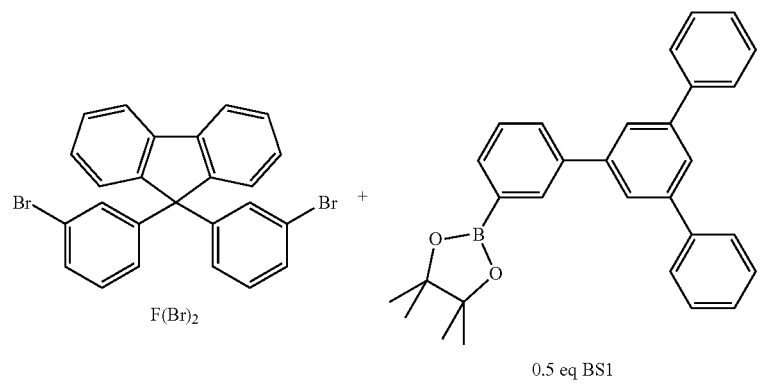
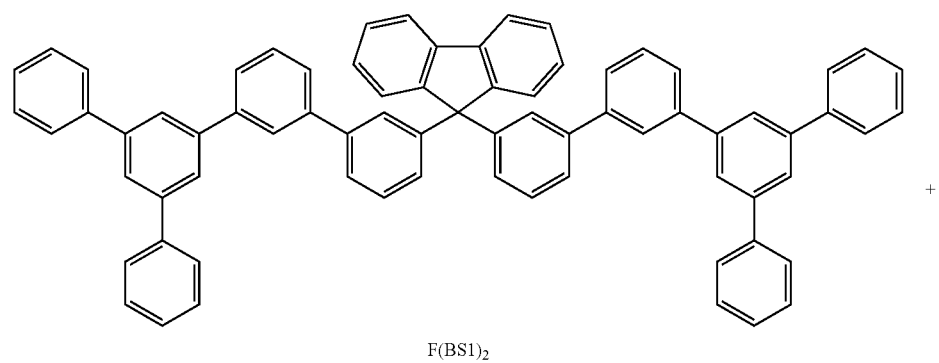
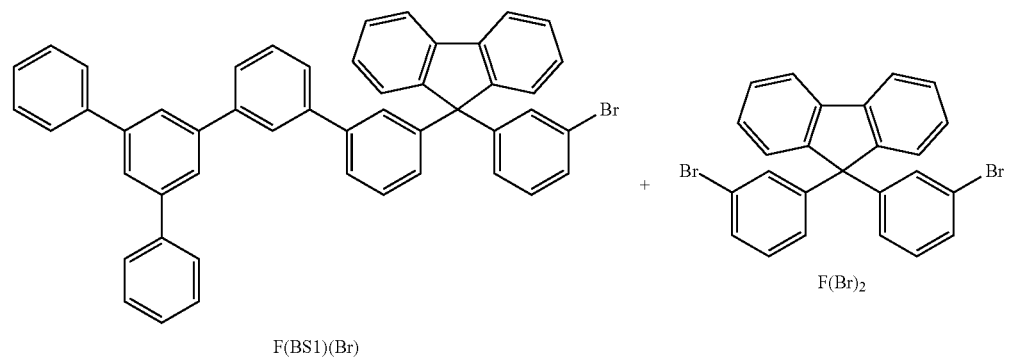
The crude products of this substoichiometric substitution can be separated by chromatography (e.g. CombiFlash Torrent from A. Semrau).
Chromatographic media and eluent mixtures suitable for this purpose are known to those skilled in the art.

| Ex. | Boron A | Product isolated | Yield |
|---|---|---|---|
| F(BS1)$_2$ | 0.5% BS1 | 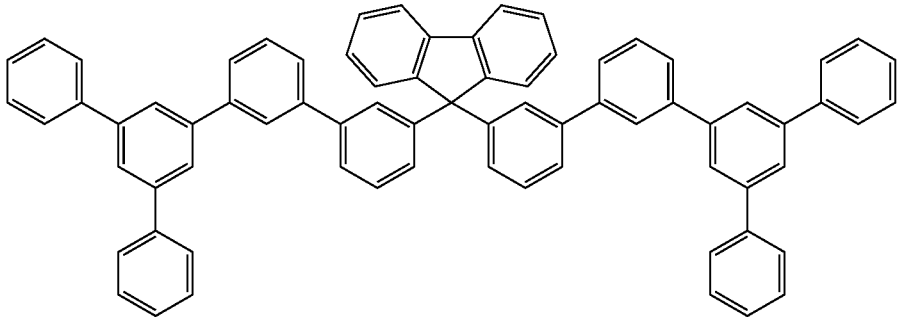 [SMILES: c1ccc(-c2cc(-c3ccccc3)cc(-c3cccc(-c4cccc(C5(c6cccc(-c7cccc(-c8cc(-c9ccccc9)cc(-c9ccccc9)c8)c7)c6)c6ccccc6-c6ccccc65)c4)c3)c2)cc1] | 21% |
| F(BS1)(Br) | | 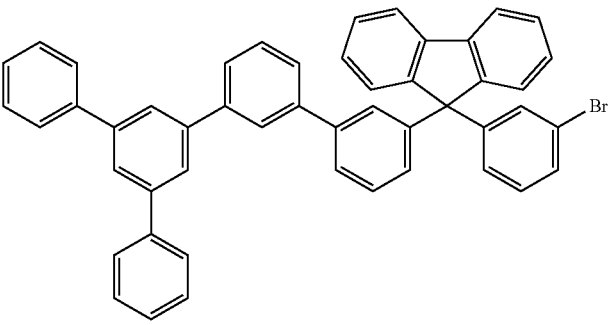 [SMILES: Brc1cccc(C2(c3cccc(-c4cccc(-c5cc(-c6ccccc6)cc(-c6ccccc6)c5)c4)c3)c3ccccc3-c3ccccc32)c1] | 33% |
| F(Br)$_2$ | | 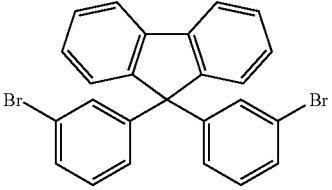 [SMILES: Brc1cccc(C2(c3cccc(Br)c3)c3ccccc3-c3ccccc32)c1] | 29% |
The F(BS1)(Br) thus obtained can be used, without further purification, to prepare F(BS1)(H) by reaction with n-butyllithium and subsequent quenching with water:
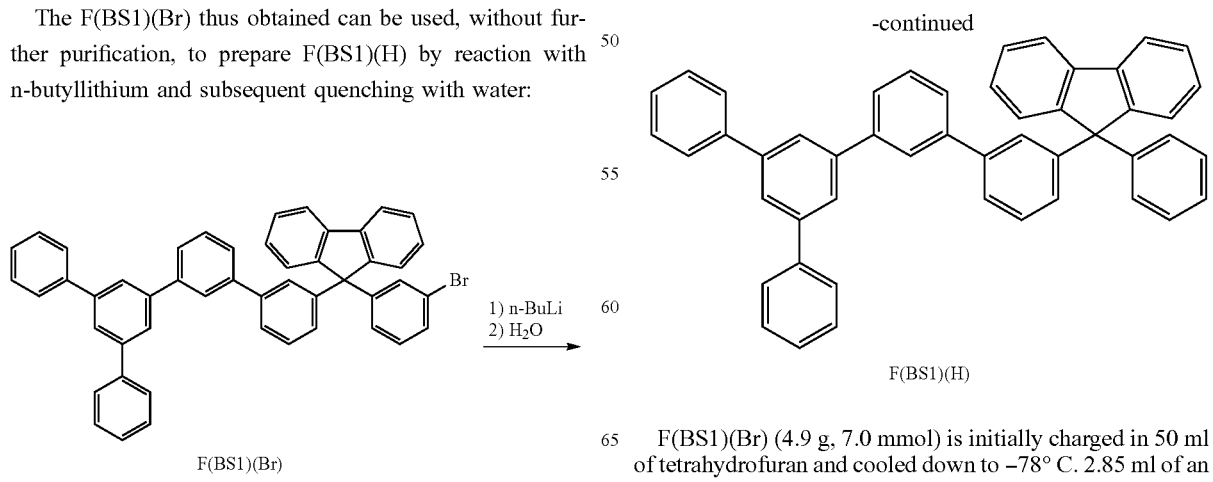
F(BS1)(Br) (4.9 g, 7.0 mmol) is initially charged in 50 ml of tetrahydrofuran and cooled down to −78° C. 2.85 ml of an n-butyllithium solution (2.5 M in n-hexane, 7.1 mmol) are slowly added dropwise and the mixture is stirred for 1 h, then the cooling is removed. At an internal temperature of about 0° C., 1 ml of water is added dropwise. The mixture is stirred for 1 h and then dried over sodium sulphate. The organic solvents are removed on a rotary evapourator. The residue is recrystallized once from a mixture of toluene and heptane (2:1 v/v). Final fractional sublimation (340° C., p about $10^{-5}$ mbar) leaves 2.5 g of F(BS1)(H) (4.0 mmol, 57% of theory) as a colourless solid having a purity of 99.9% by HPLC.

Part B: Device Examples

There are already many descriptions of the production of completely solution-based OLEDs in the literature, for example in WO 2004/037887. There have likewise been many previous descriptions of the production of vacuum-based OLEDs, including in WO 2004/058911. In the examples discussed hereinafter, layers applied in a solution-based and vacuum-based manner are combined within an OLED, and so the processing up to and including the emission layer was effected from solution and in the subsequent layers (hole blocker layer and electron transport layer) from vacuum. For this purpose, the previously described general methods are matched to the circumstances described here and combined as follows:

The structure of the components is as follows:
substrate
ITO (50 nm)
hole injection layer (HIL) (20 nm)
hole transport layer (HTL) (20 nm)
emission layer (EML) (60 nm)
hole blocker layer (HBL) (10 nm)
electron transport layer (ETL) (40 nm)
cathode Substrates used are glass plates coated with structured ITO (indium tin oxide) of thickness 50 nm. For better processing, they are coated with PEDOT: PSS (poly(3,4-ethylenedioxy-2,5-thiophene) polystyrenesulphonate, purchased from Heraeus Precious Metals GmbH & Co. KG, Germany). PEDOT:PSS is spun on from water under air and subsequently baked under air at 180° C. for 10 minutes in order to remove residual water. The hole transport layer and the emission layer are applied to these coated glass plates. The hole transport layer used is crosslinkable. A polymer of the structure shown below is used, which can be synthesized according to WO 2010/097155.

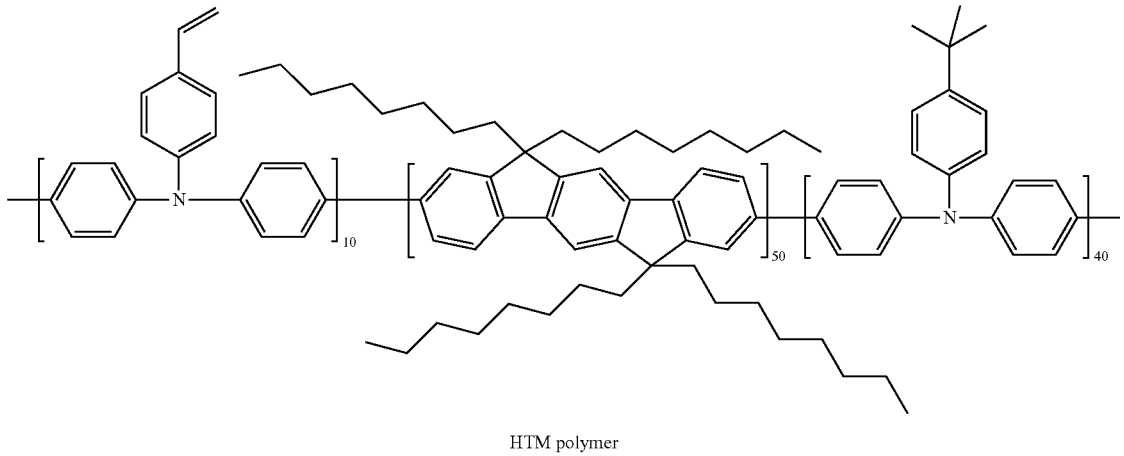

HTM polymer

The hole transport polymer is dissolved in toluene. The typical solids content of such solutions is about 5 g/l when, as here, the layer thickness of 20 nm which is typical of a device is to be achieved by means of spin-coating. The layers are spun on in an inert gas atmosphere, argon in the present case, and baked at 180° C. for 60 minutes.

The emission layer is always composed of at least one matrix material (host material) and an emitting dopant (emitter). In addition, mixtures of a plurality of matrix materials and co-dopants may occur. Details given in such a form as H1 (40%):H2 (40%):D (20%) mean here that the material H1 is present in the emission layer in a proportion by weight of 40%, the material H2 in a proportion by weight of likewise 40%, and the dopant D in a proportion by weight of 20%. The mixture for the emission layer is dissolved in toluene or optionally chlorobenzene. The typical solids content of such solutions is about 18 g/l when, as here, the layer thickness of 60 nm which is typical of a device is to be achieved by means of spin-coating. The layers are spun on in an inert gas atmosphere, argon in the present case, and baked at 160° C. for 10 minutes. Materials used are listed in Tables 2 and 3—these are both compounds of the invention and comparative examples.

The materials for the electron transport layer are applied by thermal vapour deposition in a vacuum chamber. The electron transport layer, for example, may consist of more than one material, the materials being added to one another by co-evapouration in a particular proportion by volume. Details given in such a form as ETM1:ETM2 (50%:50%) mean here that the ETM1 and ETM2 materials are present in the layer in a proportion by volume of 50% each. The materials used in the present case are shown in Table 2.

The cathode is formed by the thermal evapouration of an aluminium layer of thickness 100 nm.

The OLEDs are characterized in a standard manner. For this purpose, the electroluminescence spectra, current-voltage-luminance characteristics (IUL characteristics) assuming Lambertian radiation characteristics and the (operating) lifetime are determined. The IUL characteristics are used to determine parameters such as the operating voltage U (in V) and the external quantum efficiency (in %) at a particular brightness. LD80 @10 000 cd/m$^2$ is the lifetime until the OLED, given a starting brightness of 10 000 cd/m$^2$, has dropped to 80% of the starting intensity, i.e. to 8000 cd/m$^2$. The optoelectronic characteristics of the various OLEDs are collated in Table 5. The example Comp. is a comparative example according to the prior art; examples 11-19 show data of OLEDs comprising materials of the invention. The exact description of the materials used in the EML can be found in Table 4.

Some of the examples are elucidated in detail hereinafter, in order to illustrate the advantages of the inventive compounds.

TABLE 2

Structural formulae of the materials used in the OLEDs (without materials of the invention)

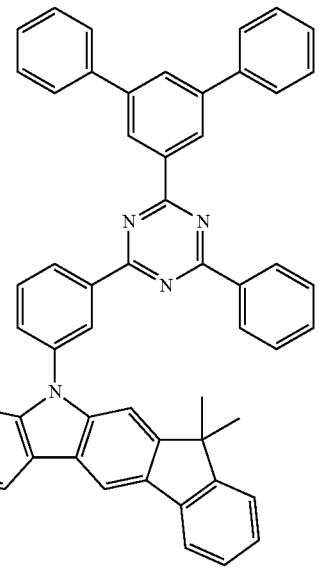

RefH1

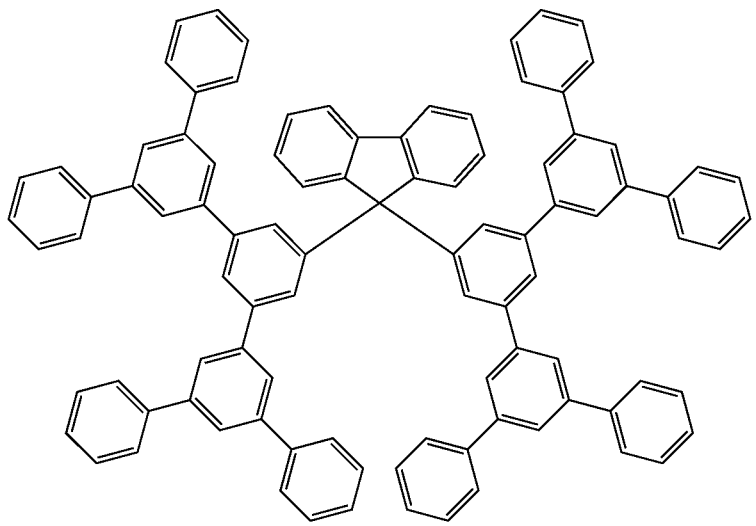

RefH2

TABLE 2-continued
Structural formulae of the materials used in the OLEDs (without materials of the invention)
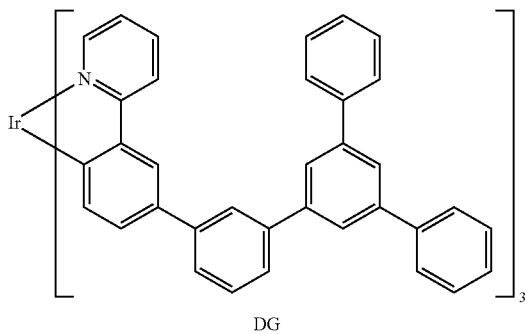
DG
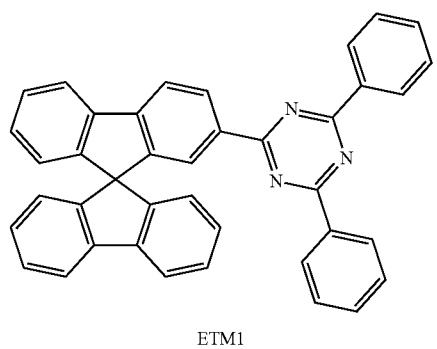 [SMILES: c1ccc(-c2nc(-c3ccccc3)nc(-c3ccc4c(c3)C3(c5ccccc5-c5ccccc53)c3ccccc3-4)n2)cc1]
ETM1
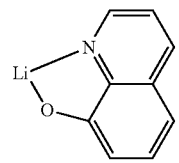
ETM2
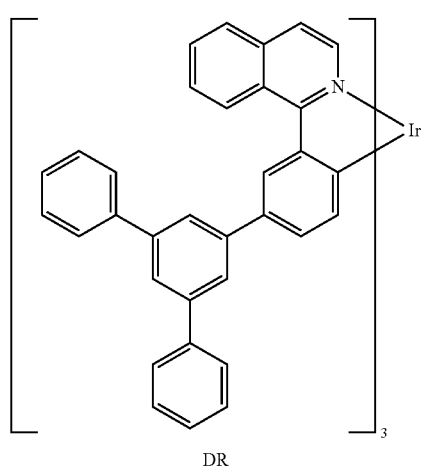
DR TABLE 3
Structural formulae of the materials of the invention used in the OLEDs
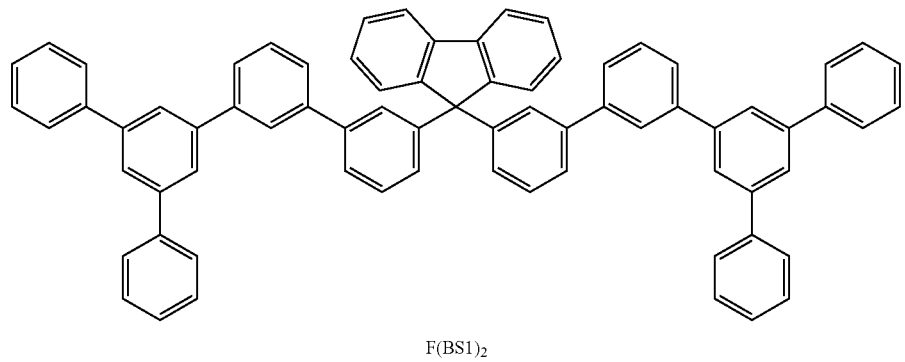 [SMILES: c1ccc(-c2cc(-c3ccccc3)cc(-c3cccc(-c4cccc(C5(c6cccc(-c7cccc(-c8cc(-c9ccccc9)cc(-c9ccccc9)c8)c7)c6)c6ccccc6-c6ccccc65)c4)c3)c2)cc1]
F(BS1)₂
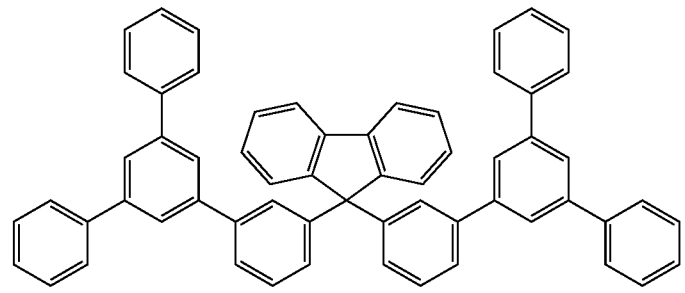
F(BS3)₂
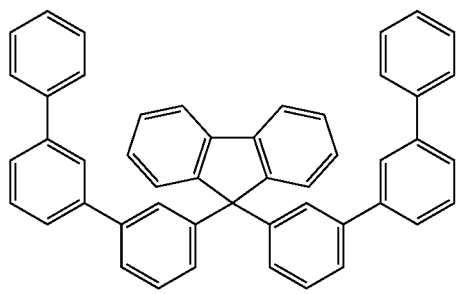
F(BS4)₂
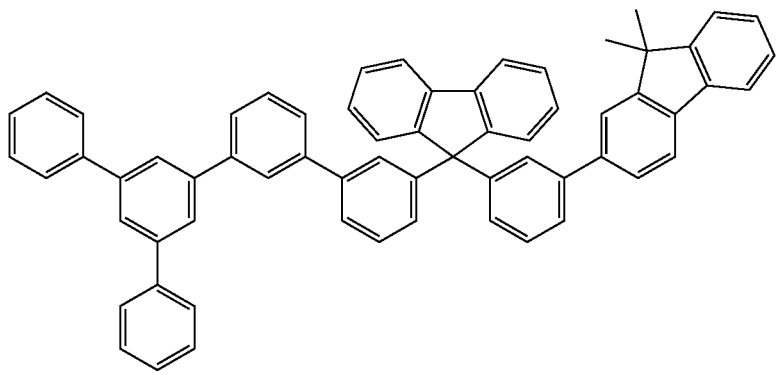
F(BS1)(BS2)

TABLE 3-continued

Structural formulae of the materials of the invention used in the OLEDs

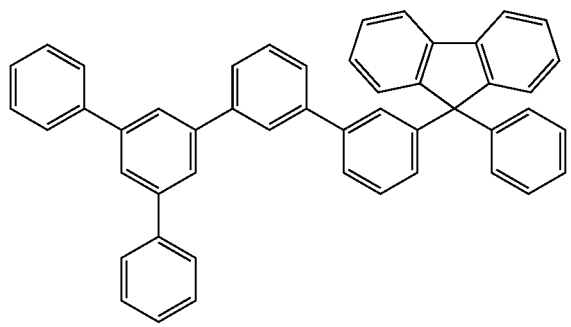

F(BS1)(H)

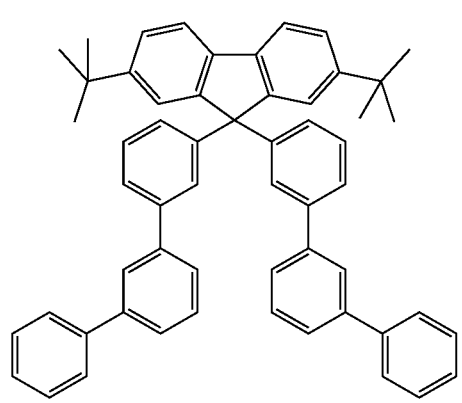

BuF(BS4)$_2$

TABLE 4

EML mixtures in the different device examples (in examples Comp1 and I1 to I6, RefH1, H2 and DG are mixed in a ratio of 40:40:20; in the examples Comp2 and I7 to I9, a mixture of RefH1, H2, DG and DR in a ratio of 20:54:20:6 is used).

| | EML composition |
|---|---|
| Comp1 | RefH1; RefH2; DG |
| I1 | RefH1; F(BS1)$_2$; DG |
| I2 | RefH1; F(BS3)$_2$; DG |
| I3 | RefH1; F(BS4)$_2$; DG |
| I4 | RefH1; F(BS1)(BS2); DG |
| I5 | RefH1; F(BS1)(H); DG |
| I6 | RefH1; BuF(BS4)$_2$; DG |
| Comp2 | RefH1; RefH2; DG; DR |
| I7 | RefH1; F(BS1)$_2$; DG; DR |
| I8 | RefH1; F(BS1)(BS2); DG; DR |
| I9 | RefH1; F(BS1)(H); DG; DR |

TABLE 5

Working examples comprising the materials of the invention

| Exp. | Voltage at 10 mA/cm$^2$ | Efficiency at 1000 cd/m$^2$ | LT80 at 10 000 cd/m$^2$ [h] |
|---|---|---|---|
| Comp1 | 7.4 | 15.0% | 220 |
| I1 | 7.5 | 16.1% | 300 |
| I2 | 7.3 | 15.4% | 210 |
| I3 | 7.0 | 15.5% | 200 |
| I4 | 7.5 | 16.0% | 250 |
| I5 | 7.0 | 15.1% | 190 |
| I6 | 6.9 | 16.3% | 230 |
| Comp2 | 7.9 | 13.6% | 245 |
| I7 | 8.0 | 13.6% | 305 |
| I8 | 7.8 | 13.9% | 290 |
| I9 | 7.5 | 13.5% | 270 |

As Table 5 shows, the materials of the invention, when used as wide bandgap material in the EML of the OLEDs, result in improvements over the prior art, particularly with regard to lifetime, but also efficiency and operating voltage.

The invention claimed is:
1. A compound comprising at least one structure of the formula (I)

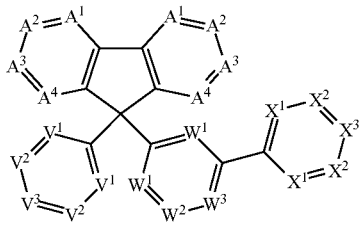

Formula (I)

where the symbols used are as follows:
$A^1, A^2, A^3, A^4$ is the same or different at each instance and is N or $CR^1$, with the proviso that not more than two of the $A^1, A^2, A^3, A^4$ groups in one cycle are N;
$V^1, V^2, V^3$ is the same or different at each instance and is N or $CR^2$, with the proviso that not more than two of the $V^1, V^2, V^3$ groups in one cycle are N;
$W^1, W^2, W^3$ is the same or different at each instance and is N or $CR^3$, with the proviso that not more than two of the $W^1, W^2, W^3$ groups in one cycle are N;
$X^1, X^2, X^3$ is the same or different at each instance and is N or $CR^4$, with the proviso that not more than two of the $X^1, X^2, X^3$ groups in one cycle are N;
$R^1, R^2, R^3, R^4$ is the same or different at each instance and is H, D, F, Cl, Br, I, $B(OR^5)_2$, CHO, $C(=O)R^5$, $CR^5=C(R^5)_2$, CN, $C(=O)OR^5$, $C(=O)N(R^5)_2$, $Si(R^5)_3$, $N(R^5)_2$, $NO_2$, $P(=O)(R^5)_2$, $OSO_2R^5$, $OR^5$, $S(=O)_5R^5$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^5$ radicals, where one or more nonadjacent $CH_2$ groups may be replaced by $-R^5C=CR^5-$, $-C\equiv C-$, $Si(R^5)_2$, $Ge(R^5)_2$, $Sn(R^5)_2$, $C=O$, $C=S$, $C=Se$, $C=NR^5$, $-C(=O)O-$, $-C(=O)NR^5-$, $NR^5$, $P(=O)(R^5)$, $-O-$, $-S-$, SO or $SO_2$ and where one or more hydrogen atoms may be replaced by D, F, Cl, Br, I, CN or $NO_2$, or an aromatic ring system which has 6 to 40 aromatic ring atoms and may be substituted in each case by one or more $R^5$ radicals, or an aryloxy or heteroaryloxy group which has 5 to 40 aromatic ring atoms and may be substituted in each case by one or more $R^5$ radicals, or a combination of these systems; at the same time, it is also possible for two or more adjacent $R^1$ substituents together to form a mono- or polycyclic, aliphatic or aromatic ring system; at the same time, it is also possible for two or more adjacent $R^2$ substituents together to form a mono- or polycyclic, aliphatic or aromatic ring system; at the same time, it is also possible for two or more adjacent $R^3$ substituents together to form a mono- or polycyclic, aliphatic or aromatic ring system; at the same time, it is also possible for two or more adjacent $R^4$ substituents together to form a mono- or polycyclic, aliphatic or aromatic ring system;
$R^5$ is the same or different at each instance and is H, D, F, Cl, Br, I, $B(OR^6)_2$, CHO, $C(=O)R^6$, $CR^6=C(R^6)_2$, CN, $C(=O)OR^6$, $C(=O)N(R^6)_2$, $Si(R^6)_3$, $N(R^6)_2$, $NO_2$, $P(=O)(R^6)_2$, $OSO_2R^6$, $OR^6$, $S(=O)R^6$, $S(=O)_2R^6$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^6$ radicals, where one or more nonadjacent $CH_2$ groups may be replaced by $-R^6C=CR^6-$, $-C\equiv C-$, $Si(R^6)_2$, $Ge(R^6)_2$, $Sn(R^6)_2$, $C=O$, $C=S$, $C=Se$, $C=NR^6$, $-C(=O)O-$, $-C(=O)NR^6-$, $NR^6$, $P(=O)(R^6)$, $-O-$, $-S-$, SO or $SO_2$ and where one or more hydrogen atoms may be replaced by D, F, Cl, Br, I, CN or $NO_2$, or an aromatic ring system which has 6 to 40 aromatic ring atoms and may be substituted in each case by one or more $R^6$ radicals, or an aryloxy or heteroaryloxy group which has 5 to 40 aromatic ring atoms and may be substituted by one or more $R^6$ radicals, or a combination of these systems; at the same time, it is also possible for two or more adjacent $R^5$ substituents together to form a mono- or polycyclic, aliphatic or aromatic ring system;
$R^6$ is the same or different at each instance and is H, D, F or an aliphatic, and/or aromatic hydrocarbyl radical having 1 to 20 carbon atoms, in which hydrogen atoms may also be replaced by F; at the same time, it is also possible for two or more adjacent $R^6$ substituents together to form a mono- or polycyclic, aliphatic or aromatic ring system;
with the proviso that
the $W^1$ and $V^1$ radicals are not bridged to one another;
the $R^2$ radicals in the $V^1, V^2, V^3$ groups and the $R^4$ radicals in the $X^1, X^2, X^3$ groups comprise a total of at least 12 aromatic carbon ring atoms;
the $R^1, R^2, R^3$ and $R^4$ radicals do not include a triazine structure and
the $V^1, V^2, V^3$ and $W^1, W^2, W^3$ groups comprise a total of not more than two $CR^2$ and $CR^3$ groups comprising an aromatic or heteroaromatic ring system.

2. The compound according to claim 1, wherein
$A^1, A^2, A^3, A^4$ is the same or different at each instance and is $CR^1$, with the proviso that not more than two of the $A^1, A^2, A^3, A^4$ groups in one cycle are N;
$V^1, V^2, V^3$ is the same or different at each instance and is $CR^2$, with the proviso that not more than two of the $V^1, V^2, V^3$ groups in one cycle are N;
$W^1, W^2, W^3$ is the same or different at each instance and is $CR^3$, with the proviso that not more than two of the $W^1, W^2, W^3$ groups in one cycle are N;
$X^1, X^2, X^3$ is the same or different at each instance and is $CR^4$, with the proviso that not more than two of the $X^1, X^2, X^3$ groups in one cycle are N.

3. The compound according to claim 1, comprising at least one structure of the formula (II)

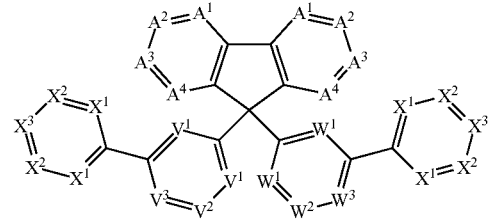

Formula (II)

where the symbols used are as defined in claim 1, where the $V^1, V^2, V^3$ and $W^1, W^2, W^3$ groups comprise not more than one $R^2$ or $R^3$ radical comprising an aromatic ring system.

4. The compound according to claim 1, wherein the compound has a molecular weight of not more than 5000 g/mol.

5. The compound according to claim 1, wherein the compound has a molecular weight of not more than 1000 g/mol.

6. The compound according to claim 1, wherein the compound has a total of not more than 5 nitrogen atoms.

7. The compound according to claim 1, wherein the compound has a total of not more than 3 nitrogen atoms.

8. The compound according to claim 1, wherein the compound has a total of not more than 5 heteroatoms apart from fluorine.

9. The compound according to claim 1, wherein the compound is a hydrocarbon or a fluorinated hydrocarbon.

10. The compound according to claim 1, wherein the compound is a hydrocarbon.

11. The compound according to claim 1, wherein the compound is a wide band gap material.

12. The compound according to claim 1, wherein the $R^1$ radicals in the $A^1, A^2, A^3, A^4$ groups do not form a fused ring system with the ring atoms of the fluorene structure.

13. The compound according to claim 1, wherein the $R^2$ radicals in the $V^1, V^2, V^3$ groups do not form a fused ring system with the ring atoms of the phenyl group to which the $R^2$ radicals are bonded.

14. The compound according to claim 1, wherein the $R^3$ radicals in the $W^1, W^2, W^3$ groups do not form a fused ring system with the ring atoms of the phenyl group to which the $R^3$ radicals are bonded.

15. The compound according to claim 1 which can be represented by a structure of the formula (III)

Formula (III)

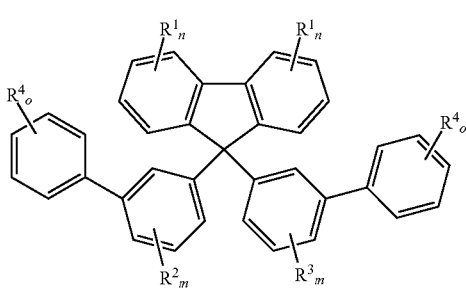

where the $R^1$, $R^2$, $R^3$, $R^4$ symbols used are as defined in claim 1 and each m is independently 0 or 1, where the sum total of the indices m is not more than 1, each n is independently 0, 1, 2, 3 or 4, and each o is independently 0, 1, 2, 3, 4 or 5.

16. The compound according to claim 1 which can be represented by a structure of the formula (IV)

Formula (IV)

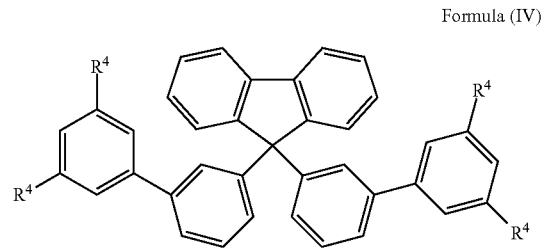

where the $R^4$ symbol used is as defined in claim 1.

17. A composition comprising at least one compound according to claim 1 and at least one further compound selected from the group consisting of fluorescent emitters, phosphorescent emitters, host materials, matrix materials, electron transport materials, electron injection materials, hole conductor materials, hole injection materials, electron blocker materials and hole blocker materials.

18. A formulation comprising at least one compound according to claim 1 and at least one solvent.

19. An electronic device comprising at least one compound according to claim 1.

20. The electronic device according to claim 19, wherein the electronic device is selected from the group consisting of organic electroluminescent devices (OLEDs, PLEDs), organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) and organic photoreceptors.

21. The compound according to claim 1, wherein the compound has a band gap of 3.0 eV or more.

* * * * *